United States Patent
Neil et al.

(10) Patent No.: US 11,684,617 B2
(45) Date of Patent: *Jun. 27, 2023

(54) METHODS OF DIAGNOSING AND TREATING ADHD IN BIOMARKER POSITIVE SUBJECTS

(71) Applicant: The Children's Hospital of Philadelphia, Philadelphia, PA (US)

(72) Inventors: Garry A. Neil, Haverford, PA (US); Liza Squires, Chester Springs, PA (US); Hakon Hakonarson, Malvern, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 81 days.

This patent is subject to a terminal disclaimer.

(21) Appl. No.: 16/606,049

(22) PCT Filed: Apr. 18, 2018

(86) PCT No.: PCT/US2018/028148
§ 371 (c)(1),
(2) Date: Oct. 17, 2019

(87) PCT Pub. No.: WO2018/195184
PCT Pub. Date: Oct. 25, 2018

(65) Prior Publication Data
US 2021/0137909 A1 May 13, 2021

Related U.S. Application Data

(60) Provisional application No. 62/487,439, filed on Apr. 19, 2017, provisional application No. 62/487,445, filed on Apr. 19, 2017, provisional application No. 62/544,441, filed on Aug. 11, 2017, provisional application No. 62/544,447, filed on Aug. 11, 2017.

(51) Int. Cl.
*A61K 31/454* (2006.01)
*A61P 25/00* (2006.01)
*A61K 45/06* (2006.01)

(52) U.S. Cl.
CPC ............ *A61K 31/454* (2013.01); *A61K 45/06* (2013.01); *A61P 25/00* (2018.01)

(58) Field of Classification Search
CPC ........ A61K 31/454; A61K 45/06; A61P 25/00
See application file for complete search history.

(56) References Cited

U.S. PATENT DOCUMENTS

| | | | |
|---|---|---|---|
| 7,396,326 B2 * | 7/2008 | Ghiron | A61N 2/006 600/13 |
| 2010/0216734 A1 * | 8/2010 | Barlow | A61K 31/506 514/43 |
| 2013/0203814 A1 | 8/2013 | Glessner et al. | |
| 2017/0105985 A1 | 4/2017 | Hakonarson et al. | |

FOREIGN PATENT DOCUMENTS

| | | | | |
|---|---|---|---|---|
| WO | WO-2012027491 A | * | 3/2012 | ............ A61P 25/20 |
| WO | 2016/205348 A1 | | 12/2016 | |
| WO | WO-2017044497 A1 | * | 3/2017 | ........... A61K 31/454 |

OTHER PUBLICATIONS

Manos, "Opinions on Drug Holidays in Pediatric ADHD", Medscape Psychiatry, Expert Column, publ. 2005, obtained from internet: https://www.medscape.org/viewarticle/519331, pp. 1-7 (Year: 2005).*
Fields, "When it's Not Just ADHD", WebMD, retrieved online at: ; https://www.webmd.com/add-adhd/childhood-adhd/features/not-just-adhd, publ 2015, pp. 1-12 (Year: 2015).*
Lo-Castro et al., Brain & Dev., vol. 33, pp. 456-461, publ. 2011 (Year: 2011).*
International Search Report and Written Opinion, dated Jun. 25, 2018 issued in International Application No. PCT/US2018/028148, filed Apr. 18, 2018.
Elia, Josephine et al. "Genome-wide copy number variation study associates metabotropic glutamate receptor gene networks with attention deficit hyperactivity disorder," Nature Genetics, vol. 44, No. 1, Jan. 2015, pp. 78-84.
Oguro-Ando, Asami et al., "A current view on contacting, -5, and -6: Implications in neurodevelopmental disorders," Molecular and Cellular Neuroscience, vol. 81, Jun. 2017, pp. 72-83.
Henrichsen, Charlotte N. et al., "Copy number variants, diseases and gene expression," Human Molecular Genetics, vol. 18, No. 1, Apr. 2009, pp. R1-R8.
Wang, Kai et al., "Copy Number Variation Detection via High-Density SNP Genotyping," Cold Spring Harbor Protocols, Jun. 2008, DOI: 10.1101/pdb.top46.
Wang, Kai et al., "PennCNV: An integrated hidden Markov model designed for high-resolution copy number variation detection in whole-genome SNP genotyping data," Genome Research, vol. 17, No. 11, Nov. 2007, pp. 1665-1674.
Hirouchi, M. et al., "Role of metabotropic glutamate receptor subclasses in modulation of adenylyl cyclase activity by a nootropic NS-105," European Journal of Pharmacology, vol. 387, No. 1, Jan. 2000, pp. 9-17.
Oka, M. et al., "Involvement of metabotropic glutamate receptors in Gi- and Gs-dependent modulation of adenylate cyclase activity induced by a novel cognition enhancer NS-105 in rat brain," Brain Research, vol. 754, Nos. 1-2, Apr. 1997, pp. 121-130.
Malykh, Andrei G. et al., "Piracetam and piracetam-like drugs: from basic science to novel clinical applications to CNS disorders," Drugs, vol. 70, No. 3, Feb. 2010, pp. 287-312.
Iafraie, A. et al., "Detection of large-scale variation in the human genome." Nat Genet, vol. 36, Sep. 2004, pp. 949-951.

(Continued)

*Primary Examiner* — Sarah Pihonak
(74) *Attorney, Agent, or Firm* — Kathleen D. Rigaut; Howson & Howson LLP

(57) ABSTRACT

This disclosure relates to the identification of a subset of mGluR network gene CNVs that are predictive of efficacy of treatment with fasoracetam, as well as the identification of an mGluR network gene CNV that is predictive of an increased likelihood of having ADHD as well as having certain symptoms associated with ADHD.

21 Claims, 6 Drawing Sheets

(56) References Cited

OTHER PUBLICATIONS

Sebat, J. et al., "Large-Scale Copy Number Polymorphisms in the Human Genome." Science, vol. 304, Jul. 2004, pp. 525-528.
Tuzun, E. et al., "Fine-scale Structural Variation of the Human Genome." Nat. Gene., vol. 37, No. 7, Jul. 2005, pp. 727-732.

* cited by examiner

METHODS OF DIAGNOSING AND TREATING ADHD IN BIOMARKER POSITIVE SUBJECTS

CROSS-REFERENCE TO RELATED APPLICATIONS

This application is a § 371 of International Application No. PCT/US2018/028148, filed Apr. 18, 2018, which claims benefit from U.S. Provisional Applications Nos. 62/487,439, filed April 19, 2017; 62/487,445, filed April 19, 2017; 62/544,441, filed Aug. 11, 2017 and 62/544,447, filed Aug. 11, 2017, respectively. The entire disclosure of each of the aforesaid applications is incorporated by reference in the present application.

This disclosure relates to the identification of a set of biomarkers for use in diagnosing and treating ADHD. This disclosure also relates to the identification of a subpopulation of ADHD characterized by certain phenotypes and predicted by the presence of a CNTN4 CNV.

BACKGROUND

Attention-deficit hyperactivity disorder (ADHD) is a neuropsychiatric disorder characterized by difficulties with attention, excessive activity, and difficulty in controlling behavior.

Studies have evaluated genetic polymorphisms or mutations that could be risk factors for developing ADHD. A large-scale, genome-wide study compared data on copy number variations (CNVs) in approximately 3,500 attention-deficit hyperactivity disorder (ADHD) cases to data from approximately 13,000 controls and found that CNVs in genes coding for metabotropic glutamate receptors (mGluR proteins or GRM genes) as well as CNVs in genes coding for proteins that interact with mGluRs occur significantly more frequently in ADHD cases compared to controls. (See WO 2012/027491 and US 2013/0203814; Elia et al., Nature Genetics, 44(1): 78-84 (2012).) The frequency of each individual genetic alteration appears to be quite rare.

There is no cure for ADHD, but the symptoms can be managed by combinations of behavior therapy and medications. Currently approved therapeutics for ADHD include several stimulant and non-stimulant drugs. Current medications are not ideal, especially stimulants, because they have several possibly harmful side effects and have short half-lives of activity. Moreover, stimulants are often misused and abused by qualifying and non-qualifying patients alike. Hence, additional ADHD medications are needed. In addition. given the genetic heterogeneity of ADHD patients, tailoring certain medication schemes to patients based on their underlying genetic profile may also improve ADHD treatment.

While a genome-wide study of copy number variation (CNVs) found an overrepresentation of rare, recurrent CNVs in genes involved in glutamatergic signaling and neural connectivity (i.e., mGluR network genes, see Elia J 2012), their frequency in an unselected clinical population of children and adolescents with ADHD has not been previously determined nor has the phenotype associated with these CNVs been evaluated. ADHD patients who are CNV-positive for CNVs affecting excitatory signaling, neurite outgrowth, and synaptic plasticity could conceivably have a different ADHD phenotype when compared with ADHD patients who are CNV-negative. Further, the optimal treatment for patients with ADHD may be different for CNV-positive versus CNV-negative patients.

We herein describe results from an interventional and non-interventional study to identify biomarkers that predict phenotypic differences associated with ADHD, to provided valuable insight into the most commonly occurring glutamatergic network CNVs, and to identify biomarkers that when present indicate likelihood of disease as well as likelihood of successful treatment with fasoracetam.

SUMMARY

As described herein and in the examples, we have found that CNVs in the gene CNTN4 encoding contactin-4, an axon-associated cell adhesion molecule, are associated with a phenotype of significantly higher incidence of disruptive behavior, difficulty completing work, anger control, risk taking, and inappropriate movements and sounds. Further, subjects with at least one CNV in CNTN4 have a more robust response to fasoractem. Thus, evaluation of the presence of CNV in CNTN4 is useful in the diagnosis and treatment of subjects with ADHD, as well as in diagnosing a subset of subjects having ADHD and disruptive behavior, difficulty completing work, anger control, risk taking, and inappropriate movements and sounds/noise making (e.g., shouting, hooting, howling, whistling, clearing throat, teeth grinding, nose sniffing, etc.). At least one CNV in CNTN4 may be used as a selective biomarker to identify such patients for treatment with fasoracetam.

Provided herein are methods of diagnosing and treating attention deficit hyperactivity disorder (ADHD) in a subject with a copy number variant (CNV) in CNTN4. Also provided are methods of diagnosing and treating a subset of subjects having ADHD and disruptive behavior, difficulty completing work, anger control, risk taking, and inappropriate movements and sounds/noise making (e.g., shouting, hooting, howling, whistling, clearing throat, teeth grinding, nose sniffing, etc.), wherein the subset of subject is identified by the presence of at least one CNV in CNTN4.

In some embodiments, the method comprises administering a therapeutically effective amount of a nonselective metabotropic glutamate receptor (mGluR) activator to a subject having a CNV in CNTN4, thereby treating ADHD. In some embodiments, the activator is fasoracetam.

Applicants have also identified a set of eight markers that predict likelihood of successful treatment with fasoracetam, wherein the markers consist of CNVs in CNTN4, GRM8, MC4R, CTNNA2, SNCA, ADRA2A, GRM5, and CA8. Reagents, kits, and compositions capable of detecting each of the CNVs in the subset of markers is provided. The following embodiments are non-limiting embodiments of the invention.

Embodiment 01 A method of treating attention deficit hyperactivity disorder(ADHD) in a subject having ADHD comprising assessing the subject for the presence or absence of a copy number variation (CNV) in a subset of mGluR network genes comprising or consisting of CNTN4, GRM8. MC4R, CTNNA2, SNC, ADRA2A, GRM5, and CA8, and administering a nonselective mGluR activator if a CNV is detected. In some embodiments, the activator is fasoracetam.

Embodiment 02 A method of treating ADHD in a subject comprising:

Embodiment 03 administering a nonselective metabotropic glutamate receptor (mGluR) activator to a subject diagnosed with or suspected of having ADHD who has a CNV in one or more of a subset of mGluR network genes comprising or consisting of CNTN4. GRM8, MC4R, CTNNA2, SNCA, ADRA2A, GRM5, and CA8. In some embodiments, the amount of activator is administered in an amount effective to result in a clinical general impression—improvement (CGI-I) score of 1 or 2 after at least four weeks of treatment and/or an improvement of at least 25%, such as at least 30%, at least 35%, or at least 40%, in an ADHD rating scale score after at least four weeks of treatment in a majority of subjects of at least one clinical trial.

Embodiment 04 The method of any one of embodiments 1-2, wherein the CNV is in CNTN4.

Embodiment 05 The method of any one of embodiments 1-3, wherein the subject is a pediatric or adolescent subject, such as a subject between the ages of 5 and 17, 8 and 17, 5 and 12,5 and 8, 8 and 12, or 12 and 17.

Embodiment 06 The method of any one of embodiments 1-4, wherein the subject is an adult.

Embodiment 07 The method of any one of embodiments 1-5, wherein the nonselective mGluR activator is fasoracetam, such as fasoracetam monohydrate.

Embodiment 08 The method of embodiment 6, wherein the fasoracetam is administered at a dose of 50-400 mg, such as 100-400 mg, or 100-200 mg, or 200-400 mg, or 100 mg, or 200 mg, or 300 mg, or 400 mg, and wherein the dose is administered once, twice, or three times daily.

Embodiment 09 The method of embodiment 7, wherein the fasoracetam is administered at a dose of 100 mg, 200 mg, 300 mg, or 400 mg twice daily, such as 100-200 mg twice daily or 200-400 mg twice daily.

Embodiment 10 The method of any one of embodiments 1-8, wherein the activator is administered in combination with a stimulant, such as methylphenidate, dexmethylphenidate, amphetamine, dextroamphetamine, or lisdexamphetamine; and/or in combination with anonstimulant, such as atomoxetine, clonidine, or guanfacine; and/or in combination with an antidepressant, such as fluoxetine, escitalopram, bupropion, mirtazapine, amitriptyline, imipramine, venlafaxine, sertraline, paroxetine, tricyclic antidepressants, selective serotonin reuptake inhibitors, serotonin and norepinephrine reuptake inhibitors, norepinephrine and dopamine reuptake inhibitors, or monoamine oxidase inhibitors; and/or in combination with an anxiolytic, such as barbiturates, pregabalin, or benzodiazepines, including chlordia/mpoxide, clorazepate, diazepan, flurazepam, halazepam, prazepam, lorazepam, lormetawepam, oxazepam, temazepam, clonazepam, flunitrazepam, nimetazepam, nitrazepam, adinazolam, alprazolam, estazolam, triazolam, climazolam, loprazolam, or midazolanm and/or in combination with an anti-psychotic, such as aripiprazole or risperidone; and/or in combination with a beta blocker, such as acebutolol, atenolol, betaxolol, bisoprolol, esmolol, nebivolol, metoprolol, cartelol, penbutolol, pindolol, carvedilol, labetalol, levobunolol, metipranolol, nadolol, propranolol, sotalol, or timolol.

Embodiment 11 The method of any one of embodiments 1-8, wherein the activator is administered in combination with non-pharmaceutical therapy, such as brain stimulation, for example vagus nerve stimulation, repetitive transcranial magnetic stimulation, magnetic seizure therapy, and/or deep brain stimulation.

Embodiment 12 The method of any one of embodiments 1-8, wherein the activator is administered as a monotherapy.

Embodiment 13 The method of embodiment I 1, wherein the activator is administered after washout of other ADHD medications.

Embodiment 14 The method of any one of embodiments 1-8, wherein a decrease in the dosage of other ADHD medications is made after the activator is administered.

Embodiment 15 The method of any one of embodiments 1-13, wherein the subject has not yet been diagnosed with ADHD when the subset of mGluR network genes are assessed.

Embodiment 16 The method of any one of embodiments 1-14, wherein the subject has symptoms of anger control issues.

Embodiment 17 The method of embodiment 15, wherein treatment with the activator increases anger control in the subject.

Embodiment 18 The method of any one of embodiments 1-14, wherein the subject has disruptive behavior.

Embodiment 19 The method of embodiment 17, wherein treatment with the activator reduces disruptive behavior in the subject.

Embodiment 20 The method of any one of embodiments 1-14, wherein the subject has risk taking behaviors.

Embodiment 21 The method of embodiment 19, wherein treatment with the activator reduces risk taking behaviors in the subject.

Embodiment 22 The method of any one of embodiments 1-14, wherein the subject has difficulty completing work.

Embodiment 23 The method of embodiment 21, wherein treatment with the activator improves the ability of the subject to complete work.

Embodiment 24 The method of any one of embodiments 1-14, wherein the subject has inappropriate movements or sounds/noise making.

Embodiment 25 The method of embodiment 23, wherein treatment with the activator reduces inappropriate movements or sounds/noise making in the subject.

Embodiment 26 The method of any one of embodiments 1-24, wherein the CNV is detected by a process comprising a genetic test comprising obtaining a sample from the subject, optionally isolating nucleic acid from the sample, optionally amplifying the nucleic acid, and analyzing the nucleic acid for a genetic alteration, and wherein the method comprises obtaining results of the genetic test prior to initial administration of the activator.

Embodiment 27 The method of any one of embodiments 1-25, wherein the CNV is a duplication.

Embodiment 25 The method of any one of embodiments 1-25, wherein the CNV is a deletion.

Embodiment 29 A method for diagnosing ADHD in a human subject comprising a) obtaining a nucleic acid sample from a subject suspected of having ADHD; b) detecting whether the sample contains at least one CNV in a subset of mGluR network genes consisting of CNTN4, GRM8, MC4R, CTNNA2, SNCA, ADRA2A, GRM5, and CA8 by contacting the nucleic acid sample with a set of probes or primers of sufficient length and composition to detect a duplication or deletion CNV in CNTN4. GRM8, MC4R, CTNNA2, SNCA, ADRA2A, GRM5, and CA8: and c) diagnosing the subject as having ADHD when the presence of at least one CNV in the nucleic acid sample is detected. In some embodiments, the subject had previously been diagnosed with ADHD and the method is for confirming the diagnosis.

Embodiment 30 A method for confirming a diagnosis of ADHD in a human subject previously diagnosed or suspected as having ADHD comprising a) obtaining a nucleic acid sample from a subject diagnosed with ADHD; b) detecting whether the sample contains at least one CNV in a subset of mGluR network genes consisting of CNTN4, GRM8, MC4R, CTNNA2, SNCA, ADRA2A. GRM5, and CA8 by contacting the nucleic acid sample with a set of probes or primers of sufficient length and composition to detect a duplication or deletion CNV in CNTN4, GRM8.

MC4R, CTNNA2, SNCA, ADRA2A, GRM5, and CA8; and c) confirming the diagnosis of ADDHD when the presence of at least one CNV in the nucleic acid sample is detected.

Embodiment 31 A method for detecting CNVs in a subset of mGluR network genes consisting of CNTN4, GRM8. MC4R, CTNNA2, SNCA, ADRA2A, GRM5, and CA8 in a human subject comprising a) obtaining a nucleic acid sample from said subject; contacting the nucleic acid sample with a set of probes or primers of sufficient length and composition to detect a duplication or deletion CNV in each of CNTN4, GRM8, MC4R CTNNA2, SNCA, ADRA2A, GRM5, and CA8. In some embodiments, contacting is annealing.

Embodiment 32 The method of any one of embodiments 28-30, wherein the mGluR network gene is CNTN4.

Embodiment 33 The method of any one of embodiments 28-30, wherein the subject has disruptive behavior.

Embodiment 34 The method of any one of embodiments 28-30, wherein the subject has difficulty completing work.

Embodiment 35 The method of any one of embodiments 28-30, wherein the subject has behaviors associated with risk taking.

Embodiment 36 The method of any one of embodiments 28-30, wherein the subject has inappropriate movements.

Embodiment 37 The method of any one of embodiments 28-30, wherein the subject has inappropriate sounds/noise making.

Embodiment 38 The method of any one of embodiments 28-30, wherein the subject has hyperactivity.

Embodiment 39 A method of treating attention deficit hyperactivity disorder(ADHD) symptoms in a subject, said symptoms including disruptive behavior, inability to complete work, failure to control anger, inappropriate risk taking, inappropriate movements, and inappropriate sounds/noise making, wherein the subject is assessed for the presence or absence of a copy number variation (CNV) in CNTN4, and treated with a nonselective mGluR activator if a CNV is detected, said activator reducing one or more of said ADHD symptoms.

Embodiment 40 The method of embodiment 38, wherein the symptom is disruptive behavior.

Embodiment 41 The method of embodiment 38, wherein the symptom is difficulty completing work.

Embodiment 42 The method of embodiment 38, wherein the symptom is having behaviors associated with risk taking.

Embodiment 43 The method of embodiments 38, wherein the symptom is inappropriate movements.

Embodiment 44 The method of embodiment 38, wherein the symptom is inappropriate sounds/noise making.

Embodiment 45 The method of embodiment 38, wherein the symptom is hyperactivity.

Embodiment 46 A kit comprising reagents capable of detecting a duplication or deletion CNV in each of CNTN4. GRM8, MC4R, CTNNA2, SNCA, ADRA2A, GRM8, and CA8. In some embodiments, the reagents comprise or consist of probes or primers of sufficient length and composition to detect a duplication or deletion CNV in each of CNTN4, GRM8, MC4R, CTNNA2, SNCA, ADRA2A, GRM5, and CA8.

Embodiment 47 A solid support comprising or consisting of nucleic acids of sufficient length and composition to detect a duplication or deletion CNV in each of CNiN4, GRM8, MC4R, CTNNA2, SNCA, ADRA2A, GRM5, and CA8.

FIGURE LEGENDS

Figure 5:
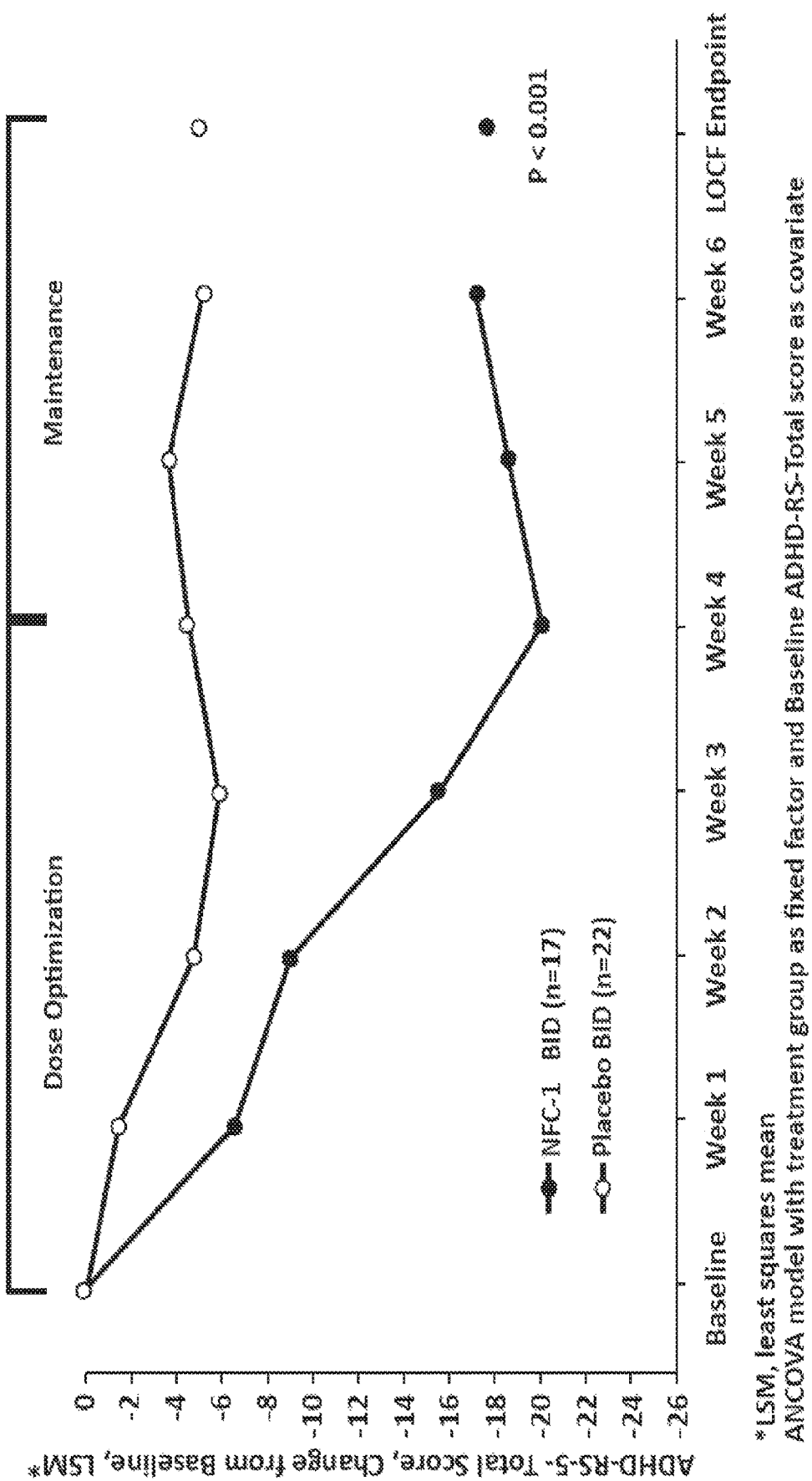

FIG. 5 shows ADHD-RS-5 total score change from baseline at endpoint (LOCF) and by visit for those subjects have a CNV in one of 8 genes: CNTN4, GRM8, MC4R. CTNNA2, SNCA, ADRA2A, GRM5, and CA8 and treated with NFC-1 (fasoracetam) or placebo. At weeks 4-6, subjects were on their optimized dose of NFC-1 or placebo.

Figure 6:
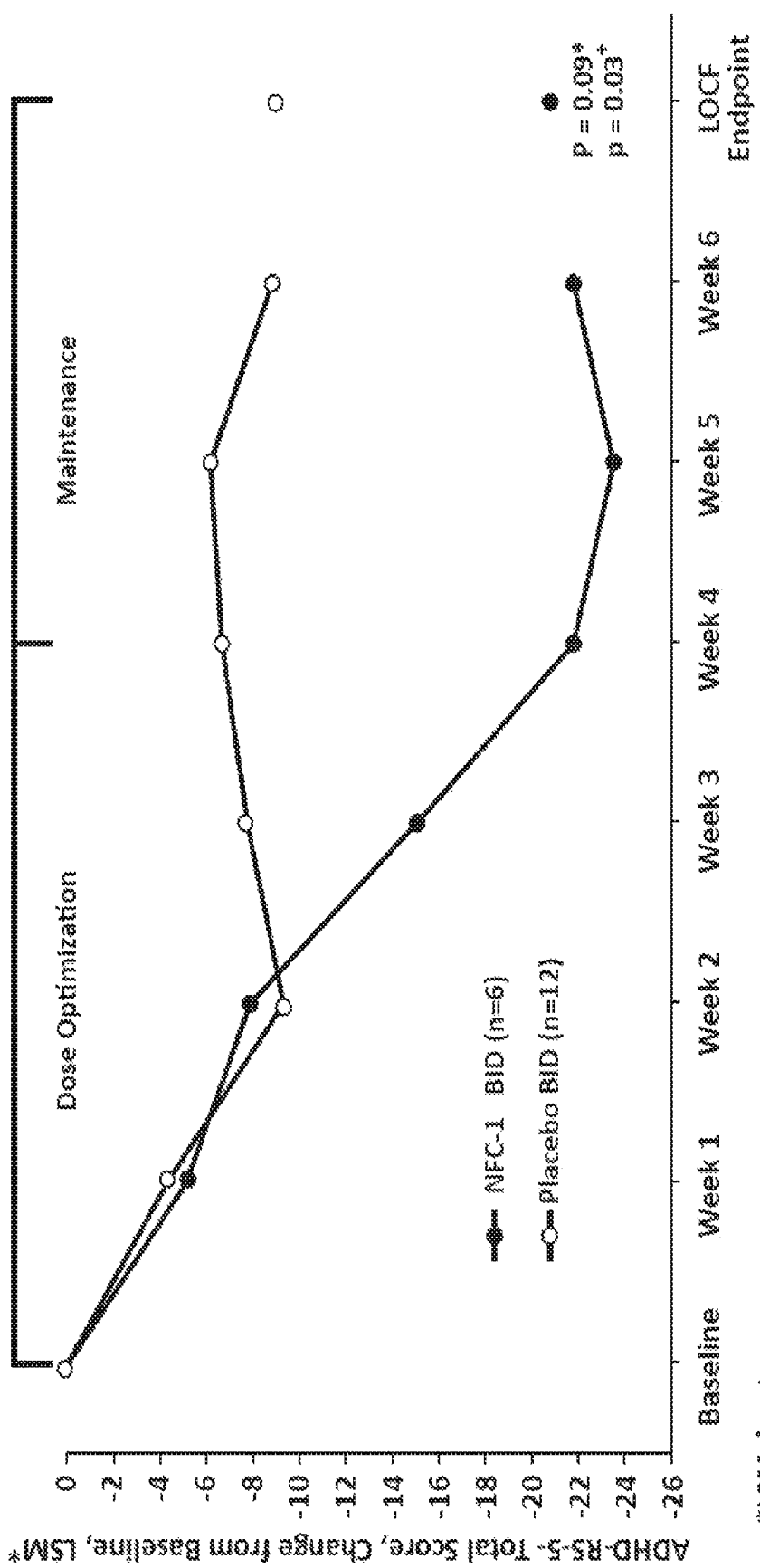

FIG. 6 shows ADHD-RS-5 total score change from baseline at endpoint (LOCF) and by visit for those subjects have a CNV in CNTN4 and treated with NFC-1 (fasoracetam) or placebo. At weeks 4-6, subjects were on their optimized dose of NFC-1 or placebo.

DETAILED DESCRIPTION

The present invention describes a phenotype of ADHD associated with the presence of a CNV in the CNTN4 gene. Individuals having ADHD and a CNV in the CNTN4 gene are more likely to also have disruptive behavior, difficulty completing work, issues with anger control, risk taking, inappropriate movements, sounds/noise making, and hyperactivity.

Further, described herein is a 8-gene subset of mGluR CNVs. The presence of a CNV in any one of the 8-gene subset is predictive of effectiveness of fasoracetam. As such, a method of treating attention deficit hyperactivity disorder (ADHD) in a subject who has a CNV in CNTN4, GRM8, MC4R, CTNNA2, SNCA, ADRA2A, GRM5, or CA8 comprising administering a nonselective metabotropic glutamate receptor (mGluR) activator to a subject is described, as are kits and compositions useful in detecting CNVs in each of the 8-gene subset.

I. Definitions

In addition to definitions included in this sub-section, further definitions of terms are interspersed throughout the text.

In this invention. "a" or "an" means "at least one" or "one or more," etc., unless clearly indicated otherwise by context. The term "or" means "and/or" unless stated otherwise. In the case of a multiple-dependent claim, however, use of the term "or" refers to more than one preceding claim in the alternative only.

An "mGluR" or metabotropic glutamate receptor refers to one of eight glutamate receptors expressed in neural tissue named mGluR1, mGluR2, mGluR3, mGluR4, mGluR5, mGluR6, mGluR7, and mGluR8. Their genes are abbreviated GRM1 to GRA8. The mGluR proteins are G-protein-coupled receptors. They are typically placed into three sub-groups, Group I receptors including mGluR1 and mGluR5 are classed as slow excitatory receptors. Group 11 includes mGluR2 and mGluR3. Group III includes mGluR4, mGluR6, mGluR7, and mGluR8. Groups II and III are classed as slow inhibitory receptors. The mGluRs are distinguished from the ionotropic GluRs or iGluRs, which are ion channel-associated glutamate receptors and are classed as fast excitatory receptors.

An "mGluR network gene," for purposes of this invention, comprises not only the mGluR genes GRM1, GRM2. GRM3. GRM4, GRM5. GRM6. GRM7, and GRM8, but also each of the other genes listed herein in Tables 1-2 as well as the regions of DNA that regulate the genes listed in Tables 1-2. In addition, "mGluR network proteins" are the proteins encoded by the mGluR network genes.

The mGluR network genes are grouped into three subsets: Tier 1, Tier 2, and Tier 3. (see US2017-0105985-AI). Tier 1 mGluR network genes, shown in Table 1, comprise 76 genes, including some GRM genes themselves as well as several other genes. The Tier 2 mGluR network genes, shown in Table 2, comprise 197 genes, and exclude the Tier 1 genes.

Tiers 1 and 2 together are included in the "primary mGluR network." The "primary network" of mGluR genes also includes the genes 4-Sep, LOC642393, and LOC653098, for a total of 276 genes. There are presently technical difficulties in assessing the 4-Sep, LOC642393, and LOC653098 genes. Thus, they are not included in Tiers 1 and 2, although they are included in the primary network of genes of the present invention. The genes of Tier 1 and Tier 2 differ in that alterations in Tier 1 genes had been documented in previous genotyping studies of subjects suffering from mental disorders. Tier 3 genes were not evaluated in the non-interventional trial described herein.

A "genetic alteration" as used herein means any alteration in the DNA of a gene, or in the DNA regulating a gene, that, for example, may result in a gene product that is functionally changed as compared to a gene product produced from a non-altered DNA. A function change may be differing expression levels (up-regulation or down-regulation) or loss or change in one or more biological activities, for example. A genetic alteration includes without limitation, copy number variations (CNVs), single nucleotide variations (SNVs) (also called single nucleotide polymorphisms (SNPs) herein), frame shift mutations, or any other base pair substitutions, insertions, and deletions.

A "copy number variation" or "CNV" is a duplication or deletion of a DNA segment encompassing a gene, genes, segment of a gene, or DNA region regulating a gene, as compared to a reference genome. In some embodiments, a CNV is determined based on variation from a normal diploid state. In some embodiments, a CNV represents a copy number change involving a DNA fragment that is 1 kilobase (kb) or larger. CNVs described herein do not include those variants that arise from the insertion/deletion of transposable elements (e.g., 6-kb KpnI repeats). The term CNV therefore encompasses terms such as large-scale copy number variants (LCVs; Iafrate et al. 2004), copy number polymorphisms (CNPs; Sebat et al. 2004), and intermediate-sized variants (ISVs; Tuzun et al. 2005), but not retrotransposon insertions.

A "CNV deletion" or "deletion CNV" or similar terms refer to a CNV in which a gene or gene segment (or region regulating a gene) is deleted. A "CNV duplication" or "duplication CNV" or similar terms refer to a CNV in which a gene or gene segment (or region regulating a gene) is present in at least two, and possibly more than two, copies in comparison with the single copy found in a normal reference genome.

A "sample" refers to a sample from a subject that may be tested, for example, for presence of a CNV in one or more mGluR network proteins, as described herein. The sample may comprise cells, and it may comprise body fluids, such as blood, serum, plasma, cerebral spinal fluid, urine, saliva, tears, pleural fluid, and the like.

The terms "pediatric subject" or "pediatric patient" are used interchangeably to refer to a human less than 18 years of age. An "adult patient" or "adult subject" refers to a human 18 years of age or older. An "adolescent patient" or "adolescent subject" is typically about 12 to 18, such as 12 to 17 or 13 to 18, years old.

"Treatment" as used herein covers any administration or application of a therapeutic for disease or disorder in a subject, and includes inhibiting the disease, arresting its development, relieving one or more symptoms of the disease, curing the disease, or preventing reoccurrence of one or more symptoms of the disease.

II. Attention Deficit Hyperactivity Disorder (ADHD)

The term "attention deficit hyperactivity disorder" or ADHD refers to a heterogeneous disorder that may be characterized at least in part by inattentiveness, hyperactivity, and impulsiveness. Per the Diagnostic and Statistical Manual of Mental Disorders, 5th Ed., (DSM-5), a physician may diagnose ADHD when a subject shows a persistent pattern of inattentiveness or hyperactivity-impulsiveness that interferes with the subject's functioning or development. ADHD may occur in at least 5% of the population and may be diagnosed in both adult and pediatric subjects.

There are three classes of ADHD: predominantly hyperactive-impulsive, predominantly inattentive, and combined hyperactive-impulsive and inattentive. Predominantly hyperactive-impulsive patients have more pronounced hyperactivity-impulsivity than inattention. Predominantly inattentive patients lack attention, but they have fewer symptoms of hyperactivity-impulsivity; these patients may be able to sit quietly in classroom setting but are not paying attention to the task that they are supposed to be performing. Combined hyperactive-impulsive and inattentive patients have significant symptoms of both inattention and hyperactivity-impulsivity. Combined ADHD is the most common type in children. Each of the diagnostic and interventional methods described herein encompass treatment of all classes of ADHD.

ADHD is a heterogeneous condition and may result from a combination of factors, such as genes, environmental factors, and/or brain injuries. In addition, ADHD patients are significantly more likely than normal individuals to have a genetic alteration such as a CNV in at least one mGluR network gene. (Se WO 20121027491 and US 2013/0203814; Elia et al., Nature Genetics, 44(1): 78-84 (2012).)

Currently approved therapeutics for ADHD include stimulant drugs, such as methylphenidate and amphetamines, as well as non-stimulant drugs, such as atomoxetine. Antidepressants may also be given in some cases, such as serotonin selective uptake inhibitors, e.g. fluoxetine, sertraline, and citalopram, as well as clonidine and guanfacine. These medications, however, may have several possible side effects and some also have short half-lives of activity.

Some subjects with ADHD may have one or more co-morbid disorders such as oppositional defiant disorder (ODD), anxiety disorder, a mood disorder, a phobia, obsessive compulsive disorder (OCD), depression, conduct disorder, Tourette's syndrome, autism, or a movement disorder.

In other cases, an ADHD subject does not have any of ODD, anxiety disorder, a mood disorder, a phobia, obsessive compulsive disorder (OCD), depression, conduct disorder, Tourette's syndrome, autism, or a movement disorder. Some subjects with ADHD may also show mood disorders or sleep disorders such as insomnia.

III. Methods of Treatment and Uses

Described herein is a 8-gene subset of mGluR network genes with predictive value for selecting treatment for subjects with ADHD. In some embodiments, gene sets or panels of eight mGluR network genes are used for analyzing samples from patients suspected of having ADHD and predicting likelihood of effectiveness of treatment with fasoracetam. In some embodiments, gene sets or panels of eight mGluR network genes are used for diagnosing patients with ADHD and treating ADHD by administering fasoracetam. In some embodiments, gene sets or panels of eight mGluR network genes are used for predicting increased likelihood of a patient having ADHD and treating ADHD by administering fasoracetam. In some embodiments, gene sets or panels of eight mGluR network genes are used for confirming diagnosis in a patient who has already received an initial diagnosis of ADHD or received an indication of likelihood of having ADHD, and treating ADHD by administering fasoracetam The gene sets or panels of eight mGluR network genes are: CNTN4, GRM8, MC4R, CTNNA2, SNCA, ADRA2A, GRM5 and CA8.

In some embodiments, the gene set or panel (e.g., 8-gene set) described herein is for use in preparing a medicament for treating or preventing ADHD in a subject.

In some embodiments, a subject suspected of, or previously diagnosed as, having ADHD is assessed for the presence or absence of a CNV in one or more, e.g., each, of a subset of mGluR network genes: CNTN4, GRM8, MC4R, CTNNA2, SNCA, ADRA2A, GRM5, and CA8, and treated with a nonselective mGluR activator if a CNV is detected.

In some embodiments, the subject has already been diagnosed with ADHD when the subset of mGluR network genes are assessed. In some embodiments, the subject has not yet been diagnosed with ADHD when the subset of mGluR network genes are assessed. In some embodiments, the subject has not yet been diagnosed with ADHD, but is suspected of having ADHD when the subset of mGluR network genes are assessed. If a CNV in one or more of the subset of genes is identified, the subject is treated with fasoracetam. In some embodiments, the subset of mGluR network genes is CNTN4, GRM8, MC4R. CTNNA2, SNCA, ADRA2A, GRM5, and CA8.

In some embodiments, the methods comprise analyzing whether a subject has a genetic alteration such as a copy number variation (CNV), which may result from a duplication or other multiplication of one or both copies of the gene or a deletion of one or both copies of the gene. A CNV deletion or duplication can alter the expression of a resulting gene product contained within or near the CNV because of the change in copy number of this gene, and may therefore contribute to a disease phenotype. However, a CNV deletion or duplication may also have no effect on relative expression of gene products in any tissue (see Henrichsen CN et al. (2009) *Human Molecular Genetics,* 2009, Vol. 18(1):R1-R8). A CNV deletion or duplication may also affect the expression of genes located near the CNV, such that expression of genes outside of the actual CNV nay also be affected. A CNV can also influence gene expression through perturbation of transcript structure; for example, a duplication CNV may lead to an increase in copy number but may lead to a decrease in gene product due to interference with normal transcription.

Table 21 provides data on CNVs that were previously described in CNTN4, GRM5, GRM8, and CTNNA2 in Elia 2012. While the Elia 2012 publication presented CNV coordinates from the hg18 build, we herein present the coordinates according to the current hg 19 build.

TABLE 21

CNVs in CNTN4, GRM5, GRM8, and CTNNA2 as presented in Elia 2012 in relation to both hg18 and hg19

| Gene | Coordinates hg18 | Coordinates hg19 | Type |
|---|---|---|---|
| CNTN4 | chr3: 1273990-1859889 | chr3: 1298990-1884889 | Del |
| CNTN4 | chr3: 1273990-1859889 | chr3: 1298990-1884889 | Del |
| CNTN4 | chr3: 1756625-1928413 | chr3: 1781625-1953413 | Del |
| CNTN4 | chr3: 1844168-1936623 | chr3: 1869168-1961623 | Del |
| CNTN4 | chr3: 1793056-1956567 | chr3: 1818056-1981567 | Del |
| CNTN4 | chr3: 1835561-1852134 | chr3: 1860561-1877134 | Del |
| CNTN4 | chr3: 1797102-1930071 | chr3: 1822102-1955071 | Del |
| GRM5 | chr11: 88269449-88351661 | chr11: 88629801-88712013 | Del |
| GRM5 | chr11: 88269449-88351661 | chr11: 88629801-88712013 | Del |
| GRM5 | chr11: 88269449-88351661 | chr11: 88629801-88712013 | Del |
| GRM5 | chr11: 83876556-91038751 | chr11: 84198908-91399103 | Del |
| GRM5 | chr11: 87996654-88837360 | chr11: 88357006-89197712 | Del |
| GRM5 | chr11: 88109331-88827923 | chr11: 88469683-89188275 | Del |
| GRM5 | chr11: 88115425-88481107 | chr11: 88475777-88841459 | Del |
| GRM5 | chr11: 88305340-88385387 | chr11: 88665692-88745739 | Del |
| GRM5 | chr11: 88305340-88385387 | chr11: 88665692-88745739 | Del |
| GRM5 | chr11: 88324615-88342595 | chr11: 88684967-88702947 | Del |
| GRM8 | chr7: 126532786-126536202 | chr7: 126745550-126748966 | Del |
| GRM8 | chr7: 126463602-126478050 | chr7: 126676366-126690814 | Del |
| GRM8 | chr7: 126532786-126536202 | chr7: 126745550-126748966 | Del |
| GRM8 | chr7: 125660695-126036276 | chr7: 125873459-126249040 | Del |
| GRM8 | chr7: 125660695-126036276 | chr7: 125873459-126249040 | Del |
| GRM8 | chr7: 125679479-125937528 | chr7: 125892243-126150292 | Del |
| GRM8 | chr7: 126503602-126563602 | chr7: 126716366-126776366 | Del |
| GRM8 | chr7: 126463602-126603602 | chr7: 126676366-126816366 | Del |
| CTNNA2 | chr2: 81035643-81654296 | chr2: 81182132-81800785 | Dup |
| CTNNA2 | chr2: 81035643-81654296 | chr2: 81182132-81800785 | Dup |
| CTNNA2 | chr2: 81419297-81446082 | chr2: 81565786-81592571 | Dup |
| CTNNA2 | chr2: 81352586-81386102 | chr2: 81499075-81532591 | Dup |

In some embodiments, ADHD patients are treated who have at least one CNV in a subset of the Tier1/2 mGluR network genes selected from CNTN4, GRM8, MC4R CTNNA2, SNCA, ADRA2A, GRM5, and CA8. In some embodiments, the patient has a genetic alteration, such as a CNV, such as a deletion or duplication that includes the gene CNTN4. In some embodiments, the CNV in CNTN4 is a deletion CNV. In some embodiments, the CNV in CNTN4 is a duplication CNV.

In some embodiments, the patient has a genetic alteration, such as a CNV, such as a deletion or duplication CNV that includes the gene GRM8. In some embodiments, the CNV in GRM8 is a deletion CNV. In some embodiments, the CNV in GRM8 is a duplication CNV.

In some embodiments, the patient has a genetic alteration, such as a CNV, such as a deletion or duplication CNV that includes the gene MC4R. In some embodiments, the CNV in MC4R is a deletion CNV. In some embodiments, the CNV in MC4R is a duplication CNV.

In some embodiments, the patient has a genetic alteration, such as a CNV, such as a deletion or duplication CNV that includes the gene CTNNA2 is a deletion CNV. In some embodiments, the CNV in CTNA2 is a duplication CNV.

In some embodiments, the patient has a genetic alteration, such as a CNV, such as a deletion or duplication CNV that includes the gene SNCA. In some embodiments, the CNV in SNCA is a deletion CNV. In some embodiments, the CNV in SNCA is a duplication CNV.

In some embodiments, the patient has a genetic alteration, such as a CNV, such as a deletion or duplication CNV that includes the gene ADRA2A. In some embodiments, the CNV in ADRA2A is a deletion CNV. In some embodiments, the CNV in ADRA24 is a duplication CNV.

In some embodiments, the patient has a genetic alteration, such as a CNV, such as a deletion or duplication CNV that includes the gene GRM8. In some embodiments, the CNV in GRM5 is a deletion CNV. In some embodiments, the CNV in GRM5 is a duplication CNV.

In some embodiments, the patient has a genetic alteration, such as a CNV, such as a deletion or duplication CNV that includes the gene CA8. In some embodiments, the CNV in CA8 is a deletion CNV. In some embodiments, the CNV in CA8 is a duplication CNV.

In some embodiments, the invention comprises a method for treating attention deficit hyperactivity disorder (ADHD) in a human subject, comprising administering an effective amount of (+)-5-oxo-D-prolinepiperidinamide,

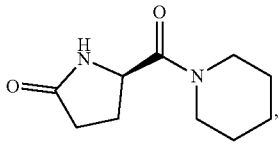 [SMILES: O=C1CC[C@H](C(=O)N2CCCCC2)N1]

and/or at least one pharmaceutically acceptable acid addition salt and/or solvate thereof, to a subject having at least one CNV in any one of CNTN4, GRM8, MC4R, CTNNA2, SNCA, ADRA2A, GRM5, and CA8, thereby treating ADHD.

In some embodiments, the invention comprises a method for treating attention deficit hyperactivity disorder (ADHD) in a human subject, comprising administering an effective amount of (+)-5-oxo-D-prolinepipendinamide,

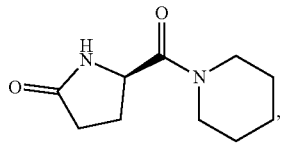 [SMILES: O=C1CC[C@H](C(=O)N2CCCCC2)N1]

and/or at least one pharmaceutically acceptable acid addition salt and/or solvate thereof, to a subject that has already been diagnosed with, or is suspected of having, ADHD and has at least one CNV in any one of CNTN4, GRM8. MC4R, CTNNA2. SNCA, ADRA2A. GRM5, and CA8, thereby treating ADHD.

In some embodiments, the invention comprises a method for treating attention deficit hyperactivity disorder (ADHD) in a human subject, comprising, a) obtaining genetic information relating to the subject; b) determining from the genetic information whether the subject has at least one copy number variation (CNV) in a subset of mGluR network genes comprising or consisting of CNTNV4, GRM8. MC4R, CTNNA2, SNCA, ADRA2A, GRM8, and CA8; and c) administering an effective amount of (+)-5-oxo-D-prolinepiperidinamide

and/or at least one pharmaceutically acceptable acid addition salt and/or solvate thereof, to the subject if it is determined that the subject has at least one CNV in any one of CNTN4, GRM8. MC4R. CTNNA2. SNCA, ADRA2A, GRM5, and CA8, thereby treating ADHD.

In some embodiments, the invention comprises a method for treating attention deficit hyperactivity disorder (ADHD) in a human subject, comprising, a) obtaining a biological sample from the human subject; b) applying the biological sample or nucleic acids isolated from the biological sample to a set of primers or probes comprising or consisting of probes of sufficient length and characteristics to detect a duplication or deletion CNV in a subset of mGluR network genes selected from CNTN4, GRM8, MC4R. CTNNA2, SNCA, ADRA2A, GRM5, and CA8?; and c) administering an effective amount of (+)-5-oxo-D-prolinepiperidinamide

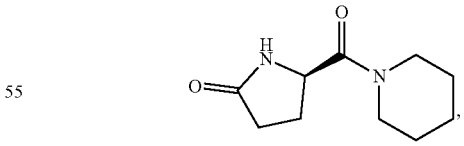

and/or at least one pharmaceutically acceptable acid addition salt and/or solvate thereof, to the subject if it is determined that the subject has at least one CNV in any one of CNTN4. GRM8, MC4R, CTNNA2, SNCA, ADRA2A, GRM5, and CA8, thereby treating ADHD.

Data described herein suggests that CNVs in CNTN4 define a subpopulation of ADHD subjects that have a phenotype that is different from the average ADHD population. Namely, CNVs in CNTN4 are predictive of an ADHD subject also having the phenotypes of disruptive behavior, difficulty completing work, difficulty controlling anger, behaviors associated with risk taking, inappropriate movements, inappropriate sounds/noise making, and hyperactivity. See FIG. 3. As such, in some embodiments, a CNV in CNTN4 in an ADHD subject indicates that the subject has an increased likelihood of also having disruptive behavior, difficulty completing work, difficulty controlling anger, behaviors associated with risk taking, inappropriate movements, inappropriate sounds/noise making, and hyperactivity. In some embodiments, methods of treating ADHD and disruptive behavior in a subject having a CNV in CNTN4 are provided comprising administering fasoracetam to a subject having a CNV in CNTN4, thereby treating ADHD and disruptive behavior.

In some embodiments, methods of treating ADHD and difficulty completing work in a subject are provided comprising administering fasoracetam to a subject having a CNV in CNTN4, thereby treating ADHD and improving the ability to complete work.

In some embodiments, methods of treating ADHD and difficulty controlling anger in a subject are provided comprising administering fasoracetam to a subject having a CNV in CNTN4, thereby treating ADHD and improving anger control.

In some embodiments, methods of treating ADHD and behaviors associated with risk taking are provided comprising administering fasoracetam to a subject having a CNV in CNTN4, thereby treating ADHD and behaviors associated with risk taking.

In some embodiments, methods of treating ADHD and inappropriate movements in a subject are provided comprising administering fasoracetam to a subject having a CNV in CNTN4, thereby treating ADHD and inappropriate movements.

In some embodiments, methods of treating ADHD and inappropriate sounds/noise making in a subject are provided comprising administering fasoracetam to a subject having a CNV in CNTN4, thereby treating ADHD and inappropriate noise making.

In some embodiments, methods of treating ADHD and hyperactivity in a subject are provided comprising administering fasoracetam to a subject having a CNV in CNTN4, thereby treating ADHD and hyperactivity.

In some embodiments, methods of treating ADHD and disruptive behavior, difficulty completing work, difficulty controlling anger, behaviors associated with risk taking, inappropriate movements, inappropriate sounds, and hyperactivity in a subject are provided comprising administering fasoracetam to a subject having a CNV in CNTN4, thereby treating ADHD and disruptive behavior, difficulty completing work, difficulty controlling anger, behaviors associated with risk taking, inappropriate movements, inappropriate sounds/noise making, and hyperactivity.

A. Methods of Diagnosis

In some embodiments, gene sets or panels of mGluR network genes are used for analyzing samples from patients suspected of having ADHD. In some embodiments, gene sets or panels of mGluR network genes are used for diagnosing patients with ADHD. In some embodiments, gene sets or panels of mGluR network genes are used for predicting increased likelihood of a patient having ADHD. In some embodiments, gene sets or panels of mGluR network genes are used for confirming diagnosis in a patient who has already received an initial diagnosis of ADHD or received an indication of likelihood of having ADHD. In some embodiments, the presence of genetic alterations such as CNV duplications or deletions within these gene sets or panels is determined. In some embodiments, the subset panel includes CNTN4, GRM8, MC4R, CTNNA2, SNCA, ADRA2A, GRM5, and CA8.

Any biological sample may be used to determine the presence or absence of the mGluR network gene subset including, but not limited to, blood, saliva, urine, serum, gastric lavage, CNS fluid, any type of cell (such as brain cells, white blood cells, mononuclear cells) or body tissue. Any biological source material whereby DNA can be extracted may be used to determine the presence or absence of the subset genes. Samples may be freshly collected, or samples may have been previously collected for any use/purpose and stored until the time of testing for genetic alterations. DNA that was previously purified for a different purpose may also be used.

In some embodiments, gene sets or panels of mGluR network genes are used for analyzing samples from patients suspected of having ADHD. In some embodiments, the presence of genetic alterations such as CNV duplications or deletions within these gene sets or panels is determined. In some embodiments, the subset panel includes CNTN4. GRM8 MC4R, CTNNA2, SNCA, ADRA2A, GRM5, and CA8.

In some embodiments, a method for diagnosing or confirming a diagnosis of attention deficit hyperactivity disorder (ADHD) in a human subject is encompassed comprising a) obtaining a nucleic acid sample from a subject suspected of having ADHD or already diagnosed with ADHD; b) detecting whether the sample contains at least one copy number variation (CNV) in a subset of mGluR network genes consisting of CNTN4. GRA8. MC4R, CTNNA2, SNCA, ADRA2A. GRM5, and CA8 by contacting the nucleic acid sample with a set of probes of sufficient length and composition to detect a duplication or deletion CNV in CNTN4. GRM8, MC4R. CTNNA2. SNCA. ADRA2A, GRM8, and CA8; and c) diagnosing the subject as having ADHD when the presence of at least one CNV in the nucleic acid sample is detected.

In some embodiments, a method for detecting CNVs in a subset of mGluR network genes consisting of CNTN4, GRM8, MC4R, CTNNA2, SNCA, ADRA2A, GRM8, and CA8 in a human subject is encompassed comprising a) obtaining a nucleic acid sample from said subject; detecting whether the sample contains at least one CNV in CNN4. GRM8, MC4R, CTNVA2, SNCA, ADRA2A, GRM5, and CA8 by contacting the nucleic acid sample with a probe of sufficient length and composition to detect a duplication or deletion CNV in the subset.

In some embodiments an ADHD phenotype in a subject with a CNV in CNTV4 can be different than an ADHD phenotype in a subject lacking this CNV. The ADHD phenotype in subjects with a CNV in CNTN4 is characterized by an ADHD and disruptive behavior, difficulty completing work, difficulty controlling anger, behaviors associated with risk taking, inappropriate movements, inappropriate sounds/noise making, and hyperactivity.

Thus, in some embodiments, methods of diagnosing ADHD and disruptive behavior in a subject are provided comprising a) obtaining a nucleic acid sample from a subject suspected of having ADHD; b) detecting whether the sample contains at least one CNV in CNTN4 by contacting the nucleic acid sample with a probe of sufficient length and composition to detect a duplication or deletion CNV in CNTN4, and c) diagnosing the subject as having ADHD and disruptive behavior when the presence of at least one CNV in the nucleic acid sample is detected. In some embodiments, the methods includes treatment comprising administering fasoracetam.

In some embodiments, methods of diagnosing ADHD and difficulty completing work in a subject are provided comprising a) obtaining a nucleic acid sample from a subject suspected of having ADHD; b) detecting whether the sample contains at least one CNV in CNTN4 by contacting the nucleic acid sample with a probe of sufficient length and composition to detect a duplication or deletion CNV in CNTN4; and c) diagnosing the subject as having ADHD and difficulty completing work when the presence of at least one CNV in the nucleic acid sample is detected. In some embodiments, the methods includes treatment comprising administering fasoracetam.

In some embodiments, methods of diagnosing ADHD and difficulty controlling anger in a subject are provided comprising a) obtaining a nucleic acid sample from a subject suspected of having ADHD; b) detecting whether the sample contains at least one CNV in CNTN4 by contacting the nucleic acid sample with a probe of sufficient length and composition to detect a duplication or deletion CNV in CNTN4: and c) diagnosing the subject as having ADHD and difficulty controlling anger when the presence of at least one CNV in the nucleic acid sample is detected. In some embodiments, the methods includes treatment comprising administering fasoracetam.

In some embodiments, methods of diagnosing ADHD and behaviors associated with risk taking in a subject are provided comprising a) obtaining a nucleic acid sample from a subject suspected of having ADHD; b) detecting whether the sample contains at least one CNV in CNTN4 by contacting the nucleic acid sample with a probe of sufficient length and composition to detect a duplication or deletion CNV in CNTN4; and c) diagnosing the subject as having ADHD and behaviors associated with risk taking vhen the presence of at least one CNV in the nucleic acid sample is detected. In some embodiments, the methods includes treatment comprising administering fasoracetam.

In some embodiments, methods of diagnosing ADHD and inappropriate sounds/noise making in a subject are provided comprising a) obtaining a nucleic acid sample from a subject suspected of having ADHD; b) detecting whether the sample contains at least one CNV in CNTN4 by contacting the nucleic acid sample with a probe of sufficient length and composition to detect a duplication or deletion CNV in CNTN4; and c) diagnosing the subject as having ADHD and inappropriate sounds/noise making when the presence of at least one CNV in the nucleic acid sample is detected. In some embodiments, the methods includes treatment comprising administering fasoracetam.

In some embodiments, methods of diagnosing ADHD and inappropriate movements in a subject are provided comprising a) obtaining a nucleic acid sample from a subject suspected of having ADHD; b) detecting whether the sample contains at least one CNV in CNTN4 by contacting the nucleic acid sample with a probe of sufficient length and composition to detect a duplication or deletion CNV in CNTN4; and c) diagnosing the subject as having ADHD and inappropriate movements when the presence of at least one CNV in the nucleic acid sample is detected. In some embodiments, the methods includes treatment comprising administering fasoracetam.

In some embodiments, methods of diagnosing ADHD and hyperactivity in a subject are provided comprising a) obtaining a nucleic acid sample from a subject suspected of having ADHD; b) detecting whether the sample contains at least one CNV in CNTN4 by contacting the nucleic acid sample with a probe of sufficient length and composition to detect a duplication or deletion CNV in CNTN4; and c) diagnosing the subject as having ADHD and hyperactivity when the presence of at least one CNV in the nucleic acid sample is detected. In some embodiments, the methods includes treatment comprising administering fasoracetam.

In some embodiments, methods of diagnosing a phenotype of ADHD characterized by disruptive behavior, difficulty completing work, difficulty controlling anger, behaviors associated with risk taking, inappropriate movements, inappropriate sounds/noise making, and hyperactivity in a subject are provided, wherein the presence of a CNV in CNTN4 is indicative of such a phenotype. In some embodiments, a method for identifying a phenotype of ADHD characterized by disruptive behavior, difficulty completing work, difficulty controlling anger, behaviors associated with risk taking, inappropriate movements, inappropriate sounds/noise making, and hyperactivity are provided comprising a) obtaining a nucleic acid sample from a subject suspected of having ADHD; b) detecting whether the sample contains at least one CNV in CNTN4 by contacting the nucleic acid sample with a probe of sufficient length and composition to detect a duplication or deletion CNV in CNTN4; and c) diagnosing the subject as having a phenotype of ADHD characterized by disruptive behavior, difficulty completing work, difficulty controlling anger, behaviors associated with risk taking, inappropriate movements, inappropriate sounds/noise making, and hyperactivity when the presence of at least one CNV in the nucleic acid sample is detected. In some embodiments, the methods includes treatment comprising administering fasoracetam.

In each of the diagnostic methods described herein, the diagnosis may be for ADHD or for an increased likelihood of ADHD.

In each of the diagnostic methods described herein, any method known to those of skill in the art may be used to assess CNV status, including those described below. Thus, in one instance probes are utilized. In other instances, instead of probes, primers are utilized flanking all or portions of the genomic regions identified herein as containing CNVs.

Various methods for determining genetic alterations are known, including the following:

A. Single Nudeotide Variadon (SNV)/Single Nucleotide Polymorphism (SNP) Genotyping Determining whether a patient has a genetic alteration, such as a CNV, in a mGluR network gene may be done by SNVISNP Genotyping, using a SNV/SNP genotyping array such as those commercially available from lilumina, Affymetrix, or Agilent. A "single nucleotide variation (SNV)," also interchangeably referred to as a "single nucleotide polymorphism (SNP)" herein, refers to a change in which a single base in the DNA differs from the usual base at that position. Millions of SNVs have been cataloged in the human genome. Some SNVs are normal variations in the genome, while others are associated with disease. While specific SNVs may be associated with disease states or susceptibility, high-density SNV genotyping can also be undertaken, whereby sequencing information on SNVs is used to determine the unique genetic makeup of an individual.

In SNV genotyping, SNVs can be determined by hybridizing complementary DNA probes to the SNV site A wide range of platforms can be used with SNV genotyping tools to accommodate varying sample throughputs, multiplexing capabilities, and chemistries. In high-density SNV arrays, hundreds of thousands of probes are arrayed on a small chip, such that many SNVs can be interrogated simultaneously when target DNA is processed on the chip. By determining the amount of hybridization of target DNA in a sample to a probe (or redundant probes) on the array, specific SNV alleles can be determined. Use of arrays for SNV genotyping allows the large-scale interrogation of SNVs.

When analyzing CNVs, after SNVs have been analyzed, a computer program can be used to manipulate the SNV data to arrive at CNV data. PennCNV or a similar program, can then be used to detect signal patterns across the genome and identify consecutive genetic markers with copy number changes. (See Wang K, et al. (June 2008) *Cold Spring Harb Protoc*). PennCNV allows for kilobase-resolution detection of CNVs. (See Wang K, et al. (Nov 2007) Genome Res. 17(11):1665-74).

In CNV analysis, the SNV genoty ping data is compared with the behavior of normal diploid DNA. The software uses SNV genotyping data to determine the signal intensity data and SNV allelic ratio distribution and to then use these data to determine when there is deviation from the normal diploid condition of DNA that indicates a CNV. This is done in part by using the log R Ratio (LRR), which is a normalized measure of the total signal intensity for the two alleles of the SNV (Wang 2008). If the software detects regions of contiguous SNVs with intensity (LRR) trending below 0, this indicates a CNV deletion. If the software instead detects regions of contiguous SNVs with intensity (LRR) trending above 0, this indicates a CNV duplication. If no change in LRR is observed compared to the behavior of diploid DNA, the sequence is in the normal diploid state with no CNV present. The software also uses B allele frequency (BAF), a normalized measure of the allelic intensity ratio of two alleles that changes when alleles are lost or gained as with a CNV deletion or duplication. For example, a CNV deletion is indicated by both adecrease in LRR values and a lack of heterozygotes in BAF values. In contrast, a CNV duplication is indicated by both an increase in LRR values and a splitting of the heterozygous genotype BAF clusters into two distinct clusters. The software automates the calculation of LRR and BAF to detect CNV deletions and duplications for whole-genome SNV data. The simultaneous analysis of intensity and genotype data accurately defines the normal diploid state and determines CNVs.

Array platforms such as those from Illumina, Affymetrix, and Agilent may be used in SNV Genotyping. Custom arrays may also be designed and used based on the data described herein.

B. Comparative Genomic Hybridization

Comparative genomic hybridization (CGH) is another method that may be used to evaluate genetic alterations such as CNVs. CGH is a molecular cytogenetic method for analyzing genetic alterations such as CNVs in comparison to a reference sample using competitive fluorescence in situ hybridization (FISH). DNA is isolated from a patient and a reference source and independently labeled with fluorescent molecules (i.e., fluorophores) after denaturation of the DNA. Hybridization of the fluorophores to the resultant samples are compared along the length of each chromosome to identify chromosomal differences between the two sources. A mismatch of colors indicates a gain or loss of material in the test sample in a specific region, while a match of the colors indicates no difference in genetic alterations such as copy number between the test and reference samples at a particular region. In certain embodiments, the fluorophores are not naturally occurring.

C. Whole Genome Sequencing, Whole Exome Sequencing, and Targeted Sequencing

Whole genome sequencing, whole exome sequencing, or targeted sequencing may also be used to analyze genetic alterations such as CNVs. Whole genome sequencing (also known as full genome sequencing, complete genome sequencing, or entire genome sequencing) involves sequencing of the full genome of a species, including genes that do or do not code for proteins. Whole exome sequencing, in contrast, is sequencing of only the protein-coding genes in the genome (approximately 1% of the genome). Targeted sequencing involves sequencing of only selected parts of the genome.

A wide range of techniques would be known to those skilled in the art to perform whole genome, whole exome, or targeted sequencing with DNA purified from a subject. Similar techniques could be used for different types of sequencing. Techniques used for whole genome sequencing include nanopore technology, fluorophore technology, DNA nanoball technology, and pyrosequencing (i.e., sequencing by synthesis). In particular, next-generation sequencing (NGS) involves sequencing of millions of small fragments of DNA in parallel followed by use of bioinformatics analyses to piece together sequencing data from the fragments.

As whole exome sequencing does not need to sequence as large an amount of DNA as whole genome sequencing, a wider range of techniques are may be used. Methods for whole exome sequencing include polymerase chain reaction methods, NGS methods, molecular inversion probes, hybrid capture using microarrays, in-solution capture, and classical Sanger sequencing. Targeted sequencing allows for providing sequence data for specific genes rather than whole genomes and can use any of the techniques used for other types of sequencing, including specialized microarrays containing materials for sequencing genes of interest.

D. Other Methods for Determining Genetic Alterations

Proprietary methodologies, such as those from BioNano or OpGen, using genome mapping technology can also be used to evaluate genetic alterations such as CNVs.

Standard molecular biology methodologies such as quantitative polymerase chain reaction (PCR), droplet PCR, and TaqMan probes (i.e., hydrolysis probes designed to increase the specificity of quantitative PCR) can be used to assess genetic alterations such as CNVs. Fluorescent in situ hybridization (FISH) probes may also be used to evaluate genetic alterations such as CNVs. The analysis of genetic alterations such as CNVs present in patients is not limited by the precise methods whereby the genetic alterations such as CNVs are determined.

B. Nonselective mGluR Activators

The mGluR proteins are typically placed into three subgroups. Group I receptors, including mGluR1 and mGluR5, are classed as slow excitatory receptors. Group II includes mGluR2 and mGluR3. Group III includes mGluR4, mGluR6, mGluR7, and mGluR8. Groups II and III are classed as slow inhibitory receptors. The mGluRs are distinguished from the ionotropic GluRs or iGluRs, which are ion channel-associated glutamate receptors and are classed as fast excitatory receptors.

A "nonselective activator of mGluRs" refers to a molecule that activates mGluRs from more than one of the group I, II, and III categories. Thus, a nonselective activator of mGluRs may provide for a general stimulation of the mGluR networks. This contrasts with specific mGluR activators that may only significantly activate a single mGluR, such as mGluR5, for example. Nonselective mGluR activators include, for example, nonselective mGluR agonists.

A "nonselective activator of mGluRs" refers to a molecule that activates mGluRs from more than one of the group I, II, and III categories. Thus, a nonselective activator of mGluRs may provide for a general stimulation of the mGluR networks. This contrasts with specific mGluR activators that may only significantly activate a single mGluR, such as mGluR5, for example. Nonselective mGluR activators include, for example, nonselective mGluR agonists.

In some embodiments, the nonselective mGluR activator is "fasoracetam." Fasoracetam is a nootropic (i.e., cognitive-enhancing) drug that can stimulate both group I and group II/III mGluRs in in vitro studies (see Hirouchi M, et al. (2000) European Journal of Pharmacology 387:9-17.). Fasoracetam may stimulate adenylate cyclase activity through activation of group I mGluRs, while it may also inhibit adenylate cyclase activity by stimulating group II and III mGluRs (see Oka M, et al (1997) Brain Research 754:121-130). Fasoracetam has been observed to be highly bioavailable (79%-97%) with a half-life of 5-6.5 hours in prior human studies (see Malykh AG, et al. (2010) Drugs 70(3):287-312). Fasoracetam is a member of the racetam family of chemicals that share a five-carbon oxopyrrolidone ring.

The structure of fasoracetam is:

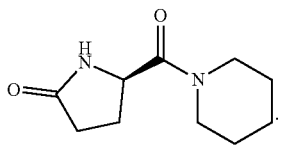 [SMILES: O=C1CC[C@H](C(=O)N2CCCCC2)N1]

The term "fasoracetam" as used herein encompasses pharmaceutically acceptable hydrates and any solid state, amorphous, or crystalline forms of the fasoracetam molecule. For example, the term fasoracetam herein includes forms such as NFC-1: fasoracetam monohydrate. In addition to NFC-1, fasoracetam is also known as C-NS-105. NS105, NS-105, and LAM-105.

NFC-1 (fasoracetam monohydrate) has been previously studied in Phase I-III clinical trials in dementia-related cognitive impairment but did not show sufficient efficacy in dementia in Phase III trials. These trials demonstrated that NFC-1 was generally safe and well tolerated for those indications. Phase III data indicated that NFC-1 showed beneficial effects on psychiatric symptoms in cerebral infarct patients and adult dementia patients with cerebrovascular diseases.

Fasoracetam is a member of the racetam family of compounds. Another racetam compound, piracetam, has been tested in pediatric ADHD subjects and found to increase ADHD symptoms in those subjects compared to a placebo control (see Akhundian, J., Iranian J. Pediatrics 2001, 11(2): 32-36).

In each of the method of treatment embodiments, a metabotropic glutamate receptor positive allosteric modulator, a metabotropic glutamate receptor negative allosteric modulator, or a tachykinin-3/neurokinin-3 receptor (TACR-3/NK3R) antagonist may be administered alone or in combination with a nonselective activator of mGluRs, for example, to subjects having an alteration in a mGluR network gene. In some embodiments, the treatment agent comprises ADX63365. ADX50938, ADX71149, AMN082, a 1-(hetero)aryl-3-amino-pyrrolidine derivative, LY341495, ADX48621, GSK1144814, or SB223412.

C. CNVs in CNTN4

CNTN4 encodes the contactin-4 gene. Contactin-4 is a member of the immunoglobulin superfamily. It is a glycosylphosphatidylinositol (GPI)-anchored neuronal membrane protein that functions as a cell adhesion molecule that may play a role in the formation of axon connections in the developing nervous system. A representative human sequence of CNTN4 is Gene ID 152330.

The terms "CNV in CNTN4" or "CNTN4 CNV" refer to a variation in CNTN4 from a normal diploid state. In some embodiments, this CNV is a deletion. In some embodiments, this CNV is a duplication. In some embodiments, a CNV represents a copy number change involving a DNA fragment that is 1 kilobase (kb) or larger.

Further, the terms "CNV in CNTN4" or "CNTN4 CNV" refer to a copy number change in a sequence in or in close proximity to the CNTN4 gene. Exemplary CNTN4 CNVs are shown in Tables 21, 4, 14, 15, and 16. Some of these CNVs are within the CNTNN4 gene, while others are in close proximity to the CNTN4 gene.

In some embodiments, subjects with ADHD and a CNV in CNTN4 have a phenotype characterized by a higher or lower presence of specific behaviors compared to subjects who have ADHD but do not have a CNV in CNTN4. In some embodiments, subjects with ADHD and a CNV in CNTN4 have a phenotype characterized by a higher or lower presence of specific behaviors compared to subjects who have ADHD and a CNV in a different mGluR network gene than CNTN4.

In some embodiments, a subject with ADHD and a CNV in CNTN4 has a higher frequency of disruptive behavior compared to a subject with ADHD without a CNV in CNTN4. In some embodiments, methods for treating ADHD with disruptive behavior in a subject with a CNV in CNTN4 are encompassed. In some embodiments, treatment of ADHD in a subject with a CNV in CNTN4 reduces symptoms of disruptive behavior. Any scale or rating instrument may be used to measure disruptive behavior, such as the Child and Adolescent Disruptive Behavior Inventory (CADBI).

In some embodiments, a subject with ADHD and a CNV in CNTN4 has a higher frequency of difficulty completing work compared to a subject with ADHD without a CNV in CNTN4. In some embodiments, methods for treating ADHD with difficulty completing work in a subject with a CNV in CNTN4 are encompassed. In some embodiments, treatment of ADHD in a subject with a CNV in CNTN4 reduces symptoms of difficulty completing work. In some embodiments, treatment of ADHD in a subject with a CNV in CNTN4 improves the subject's ability to complete work. Any scale or rating instrument may be used to measure the ability to complete work, such as the PERMP; by measurement of accuracy or speed in completing tasks; or by subject- or parent-reported measures of homework completion.

In some embodiments, a subject with ADHD and a CNV in CNTN4 exhibits anger control issues at a higher frequency of anger control compared to a subject with ADHD without a CNV in CNTN4. In some embodiments, methods for treating ADHD with difficulty controlling anger in a subject with a CNV in CN7IN4 are encompassed. In some embodiments, treatment of ADHD in a subject with a CNV in CNTN4 improves anger control. Any scale or rating instrument may be used to measure anger control, such as the Anger Regulation and Expression Scale.

In some embodiments, a subject with ADHD and a CNV in CNTN4 has a higher frequency of risk taking compared to a subject with ADHD without a CNV in CNTN4. In some embodiments, methods for treating ADHD with risk taking in a subject with a CNV in CNTN4 are encompassed. In some embodiments, treatment of ADHD in a subject with a CNV in CNTN4 reduces symptoms of risk taking. Any scale or rating instrument may be used to measure risk taking, such as the Balloon Analogue Risk Task (BART).

In some embodiments, a subject with ADHD and a CNV in CNTN4 has a higher frequency of inappropriate movements or sounds/noise making compared to a subject with ADHD without a CNV in CNTN4. In some embodiments, methods for treating ADHD with inappropriate movements or sounds/noise making in a subject with a CNV in CNTN4 are encompassed. In some embodiments, treatment of ADHD in a subject with a CNV in CNTN4 reduces inappropriate movements or sounds/noise making. Any scale or rating instrument or telemetric measuring may be used to measure inappropriate sounds/noise making or movements.

In some embodiments, a subject with ADHD and a CNV in CNTN4 has a higher frequency of hyperactivity compared to a subject with ADHD without a CNV in CNTN4. In some embodiments, methods for treating ADHD with excess hyperactivity with a CNV in CNTN4 are encompassed. In some embodiments, treatment of ADHD in a subject with a CNV in CNTN4 reduces hyperactivity. Actigraphy or any scale or rating instrument may be used to measure hyperactivity, such as the ADHD-RS-5.

D. Methods of Administration and Dosage

In some embodiments, fasoracetam may be administered as fasoracetam monohydrate (NFC-1). In some embodiments, other forms of fasoracetam may be administered. When discussing dosing, the dose provided is for the fasoracetam component of any administration. In some embodiments, fasoracetam may be administered by mouth (i.e., per os). In some embodiments, fasoracetam may be administered as capsules, tablets, caplets, oral solutions, and oral suspensions. In some embodiments, fasoracetam capsules or tablets or the like may contain 50 mg, 100 mg, 150 mg, 200 mg, 250 mg, 300 mg, 350 mg, 400 mg, 600 mg, or 800 mg of fasoracetam, or any range bounded by two of the above numbers.

In some embodiments, fasoracetan at any of the 50 mg, 100 mg, 150 mg, 200 mg, 250 mg, 300 mg, 350 mg, or 400 mg dosages above may be administered once daily, twice, or three times daily. In some embodiments, the total daily dose of fasoracetam may be 50 mg, 100 mg, 150 mg, 200 mg, 250 mg, 300 mg, 350 mg, or 400 mg given once-daily or 50 mg, 100 mg, 150 mg, 200 mg, 250 mg, 300 mg, 350 mg, or 400 mg given twice-daily. In some embodiments, fasoracetam dosing may be adjusted using a series of dose escalations. In some embodiments, pharmacokinetic data on drug level or clinical response are used to determine changes in dosing. In some embodiments, dose escalation of fasoracetam is not used. In some embodiments, subjects are treated at a dose of fasoracetam expected to be clinically efficacious without a dose-escalation protocol.

E. Therapeutic Combinations

In some embodiments, the nonselective activator of mGluR network proteins, such as fasoracetam, is used in combination with other agents for the treatment of ADHD in a subject with a CNV in CNTN4, GRM8, MC4R, CTNNA2, SNCA, ADRA2A, GRM5, and CA8. In some embodiments, fasoracetam is used in combination with current ADHD medications such as stimulant and/or nonstimulant drugs. "Stimulant" drugs used for treatment of ADHD are drugs that increase the levels of dopamine or other neurotransmitters in the brain. They are available in a variety of release forms from short to extended-release. Stimulants tend to improve attention span and focus and to regulate impulsive behaviors. Currently used stimulants include methylphenidates (e.g. Concerta®; Ritalin®; Daytrana® patch; Methylin®; Metadate®), dexmethylphenidates (e.g., Focalin®), and amphetamines such as Adderall XR® (amphetamine mixed salts), Dexedrine® (dextroamphetamine), and Vyvanset® (lisdexamphetamine dimesylate)

"Nonstimulant" (also referred to herein as "non-stimulant") drugs for ADHD are drugs that may affect neurotransmitters but do not raise dopamine levels in the brain. Nonstimulants encompass a variety of drug classes. Currently used nonstimulant drugs include atomoxetine (Strattera), which may prolong the action of norepinephrine in the brain, as well as the blood-pressure medications clonidine (Kapvay®) and guanfacine (Intuniv®), which may also improve mental functioning in ADHD patients.

In some embodiments, the activator may be used in combination with an anxiolytic (such as barbiturates, pregabalin, or benzodia,epines, including chlordiazepoxide, clorazepate, diazepam, flurazepam, halazepam, prazepam, lorazepam, lonnetazepam, oxazepam, temazepam, clonazepam, flunitrazepam, nimetazepam, nitrazepam, adinazolam, alprazolam, estazolam, triazolam, climazolam, loprazolam, or midazolam). It may also be used in combination with antidepressants such as serotonin selective uptake inhibitors, e.g. fluoxetine, sertraline, and citalopram. Antidepressants include, for example, fluoxetine, escitalopran, bupropion, mirtazapine, amitriptyline, imipramine, venlafaxine, sertraline, paroxetine, or other compounds in the classes of tricyclic antidepressants, selective serotonin reuptake inhibitors, serotonin and norepinephrine reuptake inhibitors, norepinephrine and dopamine reuptake inhibitors, monoamine oxidase inhibitors, or other drugs approved for the use of depression). In some embodiments, the other agent may be a beta-blocker (such as acebutolol, atenolol, betaxolol, bisoprolol, esmolol, nebivolol, metoprolol, cartelol, penbutolol, pindolol, carvedilol, labetalol, levobunolol, metipranolol, nadolol, propranolol, sotalol, timolol, or other selective or nonselective blockers of beta-adrenergic receptors). In some embodiments, the other agent may be an anti-psychotic drug such as aripiprazole or risperidone.

In some embodiments, fasoracetam may be used in combination with a non-pharmacologic treatment, such as psychotherapy or brain stimulation therapies. For example, in some embodiments the patient is further treated with brain stimulation, which may be vagus nerve stimulation, repetitive transcranial magnetic stimulation, magnetic seizure therapy, deep brain stimulation, or any other therapies involving modulation of brain function by electricity, magnets, or implants.

In some embodiments, the activator is administered as a monotherapy. In some embodiments, the activator is administered after washout of other ADHD medications.

In some embodiments, administering the activator allows a decrease in the dosage of other ADHD medications.

F. Efficacy Measures for Determining Responsiveness to Treatment

Several different outcome measures or rating scales are validated for determining the efficacy of a treatment for ADHD, for example, in clinical trials. These can include measures of attention, tasks, and global measures of the severity or improvement of patients. Rating scales currently used in ADHD clinical trials in pediatric patients include the ADHD Rating Scale IV, Vanderbilt scale, actigraphy, Quotient ADHD test scale, and the PERMP-Math test scale. A Clinical global impressions severity/improvement (CGI-S and CGI-I) score is also frequently used as a secondary efficacy measurement as it may correspond well to the judgments of global well-being that clinicians make in their normal clinical practice of treating ADHD patients.

The ADHD Rating Scale (ADHD-RS) IV or V is based on 18 inattentive and hyperactive/impulsive diagnostic criteria for ADHD provided in the Fourth Edition of the Diagnostic and Statistical Manual of Mental Disorders, 1994, (DSM-4) or the Fifth Edition, 2016, (DSM-V), published by the American Psychiatric Association. Each of the 18 items is scored on a 4-point scale of 0, 1, 2, or 3, with 0 indicating no symptoms to 3 indicating severe symptoms. Accordingly, the Scale results in possible scores ranging from 0 to 54 with a higher score reflecting a more severe disease condition. There are a few versions of the ADHD Rating Scale IV or V depending upon who is recording the information, a parent/teacher or a clinician, and depending upon whether the patient is a pediatric or adult patient. But all versions are designed to assess the same set of 18 items.

The Vanderbilt Rating Scale is a measure that can be completed by parents or teachers (separate forms, see "Vanderbilt Rating Scale-Parents" and "Vanderbilt Rating Scale-Teachers"). The Vanderbilt scale rates the child's behavior on items such as attention, finishing tasks, hyperactivity, difficulty waiting, and measures of conduct or oppositional defiant disorders—as well as measures of overall school performance and interactions with others. The first 18 items on the Vanderbilt scale correspond to those of the ADHD Rating Scale IV above while the Vanderbilt scale also includes items 19-47 related to other mental disorders including ODD (items 19-26), conduct disorder (items 27-40), anxiety (items 41, 42, and 47), and depression (items 43-46). Each of the behavioral assessment items on the Vanderbilt Scale are rated 0, 1, 2, or 3, with 0=never occurring; 1 —occasionally, 2 —often, and 3 —very often. Thus, the ADHD Rating Scale IV, ADHD Rating Scale V, and items 1-18 of the Vanderbilt Rating Scale are equivalent scales, while additional items on the Vanderbilt Scale assess co-morbid phenotypes and disorders.

The first 18 items of the "Vanderbilt Rating Scale-Parents" are in the form of a questionnaire and include items such as: (3) does not seem to listen when spoken to directly; (4) does not follow through when given directions and fails to finish activities (not due to refusal or failure to understand); (9) is forgetful in daily activities; (10) fidgets with hands or feet or squirms in seat; (16) blurts out answers before questions have been completed; (17) has difficulty waiting his or her turn. Each of the items are rated on a scale of 0, 1, 2, or 3, with 0=never; 1=occasionally, 2=often, and 3 —very often. A total score of 0 to 54 is computed based on the answers to the 18 questions.

As used herein an "ADHD rating scale score," "ADHD-RS," "ADHD-RS-5," "ADHD score" or "Vanderbilt ADHD score" are used interchangeably to refer to the computed score of the 18 items of the ADHD Rating Scale TV or V or the first 18 items of the Vanderbilt Rating Scale in any of their associated versions, e.g., for parent, teacher, or clinician to complete, and for a pediatric subject or adult subject. Clinical trials may assess the impact of drug or placebo on the ADHD score or Vanderbilt ADHD score (i.e. the score of 0 to 54 based on the first 18 items in the ADHD or Vanderbilt rating scale). In some cases, results of a clinical trial population may be analyzed by comparing the average score or a percentage change in score over time of administration of drug. Patients may be considered "improved," for example, if their Vanderbilt ADHD score is reduced by at least 25% compared to a placebo or pre-study baseline, and "robustly improved," for example, if their score is reduced by at least 40% compared to a pre-study or placebo baseline.

Some embodiments of methods of treatment herein refer to administering to a subject an amount of a nonselective mGluR network activator effective to reduce an ADHD rating scale score or Vanderbilt ADHD score by at least 25%, such as at least 30% or at least 35% or at least 40%, after a certain period of treatment, such as 1, 2, 3, 4 or 5 weeks, in most clinical trial subjects. In such embodiments, the amount for administration may, for example, be selected based on clinical results showing that the amount led to such a result in most previously assessed clinical patients. For example, if a subject to be treated is a pediatric subject, the treatment amount may be selected based on achieving such results in most patients in a clinical trial of pediatric subjects.

The Clinical Global Impression Scale (CGI) is a widely-used assessment instrument in psychiatry and is a common secondary efficacy measure for ADHD clinical trials. The CGI scale generally asks the clinician to provide a global assessment of the patient's function, symptoms, and adverse events based on the clinician's experience with ADHD patients. The CGI scale has two component measurements, CGI-S(clinical global impression—severity; a measure of disease severity) and CGI-1 (clinical global impression —improvement; a measure of improvement in symptoms). Both scales range from 1 to 7. The CGI-S scale ranges from 1 (normal) to 3 (mildly ill), 4 (moderately ill), 5 (markedly ill), 6 (severely ill) and 7 (among the most extremely impaired). The CGI-I scale ranges from 1 (very much improved), 2 (much improved), 3 (minimally improved), 4 (no change), 5 (minimally worse), 6 (much worse), to 7 (very much worse). In general, subjects with a CGI-I score of 1 or 2 compared to a base-line or placebo level are considered responders to a treatment regimen. For example, in some cases a responder to a drug regimen may show a reduction in ADHD score or Vanderbilt ADHD score of at least 25%, such as at least 30%, at least 35%, or at least 40%, as well as a CGI-I score of either 1 or 2 after a certain period of treatment, such as 1, 2, 3, 4, or 5 weeks In some cases, a responder may show a change in CGI-1 score after 1, 2, 3, 4, or 5 weeks, for example, of 1 to 2 points. In some cases, a responder may show a CGI-S score of 1 or 2 or 3 after 1, 2, 3, 4, or 5 weeks.

In some embodiments of the methods herein, the amount of nonselective mGluR activator administered to a subject is chosen based on that amount's ability to give a CGI-I score of 1 or 2 in a majority of subjects in a clinical trial, for example a clinical trial of similar subjects. Thus, for example, if a pediatric clinical trial shows that a particular amount of activator gives a CGI-I score of 1 or 2 in a majority of patients in the trial after a particular period of time, that amount may be chosen to give to another pediatric subject as a treatment dose. Similarly, in some embodiments, the amount of nonselective mGluR activator administered to a subject is chosen based on an amount that gave a reduction of at least $^{25}$%, such as at least 35%, at least 35%, or at least 40% in Vanderbilt ADHD score in a clinical trial of similar subjects. In some embodiments, an amount is chosen for administration based on the amount that achieved a CGI-S score of 1-3, such as 1-2 in subjects after a period of treatment. In some cases, an amount is chosen for administration that gave a combination of these effects in most clinical trial subjects.

The Permanent Product Measure of Performance (PERMP)-Math is an individualized mathematics test that can be performed by a patient periodically when on and off medication for ADHD. It is used, for example, to monitor classroom performance in an experimental laboratory setting.

In general, the PERMP test comprises 5 pages of 400 problems that subjects are directed to attempt over a 10-minute period. Subjects may be given a pre-test first to determine their mathematical skill level. Subjects are directed to answer as many questions as they can in the 10-minute period and the test is generally scored on a 0-800-point scale based on the number of questions attempted and the number of questions answered correctly within the time limit. Subjects receive a different version of the test at each setting.

Quotient ADHD scores use a medical device to measure hyperactivity, attention, and impulsivity in patients with ADHD. The Quotient ADHD tool uses motion tracking technology to track a patient's micro-movements while they complete a 15-20-minute computerized test. Following the patient's completion of the test, patterns of motions, the accuracy of responses, and fluctuations in attention state can be analyzed.

Actigraphy is non-invasive monitoring of human rest/activity cycles, using an actigraph worn by the patient to document body movements. Actigraphs can be worn during school, for example, to measure activity levels. Actigraphy analysis can measure changes in sleep and hyperactivity that may be seen with treatment for ADHD.

Additional questionnaires may also be used by clinicians to assess co-morbid symptoms such as anger control and disruptive behaviors as well as to assess co-morbid disease conditions.

G. Articles of Manufacture

In some embodiments, the invention comprises articles of manufacture that may be used in the methods and treatments described herein. In some embodiments, the manufacture is a solid support or microarray for use in detecting genetic alterations in the mGluR network gene subset as described herein: CNTN4, GRM8, MC4R, CTNNA2, SNCA. ADRA2A, GRM5, and CA8. In some embodiments, the article of manufacture comprises nucleic acid primers or probes for detecting CNVs in CNTN4, GRM8, MC4R, CTNNA2, SNCA, ADRA2A, GRM5, and CA8.

Thus, for example, in some embodiments, the mGluR network gene subset of CNTN4, GRM8, MC4R, CTNNA2, SNCA, ADRA2A, GRM5 and CA8 are assayed to determine if there is a genetic alteration in one or more of the genes, such as a CNV. A solid support or microarray, such as on a chip, that contains appropriate probes or primers for determining the presence of genetic alterations in CNTN74, GRM8, MC4A CTNNA2, SNCA, ADRA2A, GRM8, and CA8 is provided.

In some embodiments, the manufacture is a set of probes for CNTN4, GRM8, MC4R, CTNNA2, SNCA, ADRA2A, GRM8, and CA8. In some embodiments, the probes are labelled. In certain embodiments, the labels are non-naturally occurring. In some embodiments, the probes comprise non-natural nucleotides. Sets of probes may be manufactured for determining the presence of genetic alterations in CNTN4, GRM8, MC4R, CTNNA2, SNCA, ADRA2A, GRM8, and CA8. These various probe sets may be used in methods of determining the presence of genetic alterations, such as CNVs and SNVs in CNTN4, GRM8, MC4R, CTNNA2, SNCA, ADRA2A, GRM5, and CA8 as part of a method of treating ADHD. The probes or primers may be immobilized or affixed to the solid support such that they do not diffuse off of the support when in solution. In certain embodiments, the probes or primers are chemically or covalently attached to the solid support.

Also provided are kits comprising reagents capable of detecting CNVs in the eight-gene subset of CNTN4, GRM8, MC4R, CTNNA2, SNCA, ADRA2A, GRM5, and CA8 described herein. In some embodiments, a kit further comprises one or more of a solvent, solution, buffer instructions, or desiccant. In some embodiments, the kit further comprises fasoracetam. Kits comprising reagents capable of detecting the eight-gene set/panel are provided, wherein the genes are CNTN4, GRM8, MC4R, CTNNA2, SNCA, ADRA2A, GRM5, and CA8. In some embodiments, kit is for use in preparing a medicament for treating or preventing a disease or disorder in a subject.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed considering the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent As used herein, the term "include" and its grammatical variants are intended to be non-limiting, such that recitation of items in a list is not to the exclusion of other like items that can be substituted or added to the listed items.

EXAMPLES

The following examples are provided to illustrate certain disclosed embodiments and are not to be construed as limiting the scope of this disclosure in any way.

Example 1—Noninterventional Study of Glutamatergic Network Gene CNVs in Children and Adolescents with ADHD A study was undertaken to determine the frequency of CNVs in glutamatergic network genes in a large clinical population of children and adolescents with ADHD and to compare ADHD-related phenotypes to CNV status.

This was a multicenter, noninterventional study conducted at 32 geographically dispersed study sites. The study enrolled children/adolescents of ≥6 and ≤17 years of age who either had a documented ADHD history or who met DSM-V criteria for ADHD at the screening visit.

Phenotype assessment was made of ADHD symptoms and history, treatment, and comorbidity data collected with questionnaire-directed interview. The questionnaire included questions to parents regarding behaviors that were current areas of concern.

Genotype assessment was done via saliva DNA samples. The sequences of 273 genes of interest (i.e. mGluR network genes) based on previously identified CNVs associated with ADHD and association with glutamatergic signaling and neuronal connectivity (i.e., mGluR network genes) were assessed. Genotyping was done using Illumina Omni 2.5 chip.

Tier 1 mGluR network genes, shown in Table 1, comprise 76 genes, including some GRM genes themselves as well as several other genes. The Tier 2 mGluR network genes, shown in Table 2, comprise 197 genes, and exclude the Tier 1 genes.

The 273 genes listed in Tables 1 and 2 comprise the genes referred to in these Examples as "mGluR network genes," "glutamatergic signaling genes," or "genes of interest."

TABLE 1

Tier 1 mGluR network genes

| Tier 1 Gene | GeneRange (hg19) | GeneRange +500 kb(hg19) | GeneRange (hg18) | StartSNP (GeneRange +500 kb) | EndSNP (GeneRange +500 kb) |
|---|---|---|---|---|---|
| ACAT1 | chr11: 107992257-108018891 | chr11: 107492257-108518891 | chr11: 107497467-107523485 | rs7925970 | kgp3957860 |
| ACCN1 | chr17: 31340105-32483825 | chr17: 30840105-32983825 | chr17: 28364218-29507938 | rs2519865 | kgp10854156 |
| ACTR2 | chr2: 65454828-65498390 | chr2: 64954828-65998390 | chr2: 65308405-65351891 | rs1477043 | kgp4266233 |
| ADCY1 | chr7: 45614124-45762714 | chr7: 45114124-46262714 | chr7: 45580649-45729239 | rs2289367 | kgp13398740 |
| ADRBK1 | chr11: 67033904-67054029 | chr11: 66533904-67554029 | chr11: 66790480-66810605 | kgp7862175 | kgp2126040 |
| ALDOA | chr16: 30064410-30081741 | chr16: 29564410-30581741 | chr16: 29971972-29989236 | kgp733881 | kgp6386467, rs33997546 |
| APP | chr21: 27252860-27543446 | chr21: 26752860-28043446 | chr21: 26174731-26465003 | rs7281883 | kgp2004872 |
| ARL15 | chr5: 53180613-53606403 | chr5: 52680613-54106403 | chr5: 53216370-53642160 | kgp10474479 | rs10058571 |
| ATXN7L3 | chr17: 42269172-42275529 | chr17: 41769172-42775529 | chr17: 39624698-39631055 | rs11650560 | rs6503398 |
| BDKRB2 | chr14: 96671134-96710666 | chr14: 96171134-97210666 | chr14: 95740887-95780419 | kgp19731302 | kgp1905230 |
| CA8 | chr8: 61101422-61193954 | chr8: 60601422-61693954 | chr8: 61263976-61356508 | kgp9568230 | kgp1623935 |
| CACNA1B | chr9: 140772240-141019076 | chr9: 140272240-141519076 | chr9: 139892061-140136452 | kgp18327422 | kgp12374930 |
| CACYBP | chr1: 174968570-174981163 | chr1: 174468570-175481163 | chr1: 173235193-173247786 | rs1013769 | kgp15391194 |
| CALM1 | chr14: 90863326-90874619 | chr14: 90363326-91374619 | chr14: 89933125-89944363 | kgp828819 | kgp22766175 |
| CHRM3 | chr1: 239549864-240049896 | chr1: 239049864-240549896 | chr1: 237616487-238116519 | kgp1999037 | rs1537850 |
| CIC | chr19: 42788816-42799949 | chr19: 42288816-43299949 | chr19: 47480656-47491789 | kgp21495548 | kgp22794755 |
| CNP | chr17: 40118758-40129754 | chr17: 39618758-40629754 | chr17: 37372284-37383280 | kgp4988562 | kgp1573374 |
| CNTN4 | chr3: 2140549-3099645 | chr3: 1640549-3599645 | chr3: 2117246-3074645 | kgp7465125 | kgp11488181, rs9811783 |
| CRHR1 | chr17: 954314-1170453 | chr17: 454314-1670453 | chr17: 41217448-41268973 | kgp12243700 | kgp2967880 |
| CTNNA2 | chr2: 79412356-80875988 | chr2: 78912356-81375988 | chr2: 79265864-80729416 | kgp2692843 | kgp6161954 |
| DISC1 | chr1: 231664398-232177019 | chr1: 231164398-232677019 | chr1: 229829183-230343641 | kgp15830047 | kgp10247084 |
| DPP6 | chr7: 153584418-154685995 | chr7: 153084418-155185995 | chr7: 153215351-154316928 | rs1822707 | rs7781545 |
| DYNLL1 | chr12: 120907659-120936298 | chr12: 120407659-121436298 | chr12: 119392042-119420681 | rs2393569 | rs1169303 |
| FPR1 | chr19: 52249022-52255150 | chr19: 51749022-52755150 | chr19: 56940837-56946962 | rs11084062 | kgp21351572 |
| GAPDH | chr12: 6643656-6647536 | chr12: 6143656-7147536 | chr12: 6513917-6517797 | kgp12277967 | kgp3951989 |
| GNA15 | chr19: 3136190-3163766 | chr19: 2636190-3663766 | chr19: 3087190-3114766 | kgp9441497 | kgp8109485 |
| GNAI2 | chr3: 50263723-50296786 | chr3: 49763723-50796786 | chr3: 50238727-50271790 | rs1049256 | kgp1163947 |
| GNAO1 | chr16: 56225250-56391356 | chr16: 55725250-56891356 | chr16: 54782751-54948857 | rs36013 | kgp16402238 |
| GNAQ | chr9: 80335190-80646219 | chr9: 79835190-81146219 | chr9: 79525010-79836012 | rs3802497 | kgp478959 |
| GRIK1 | chr21: 30909253-31312282 | chr21: 30409253-31812282 | chr21: 29831124-30234153 | kgp6759057 | kgp13183414 |
| GRIK3 | chr1: 37121127-37499844 | chr1: 36761127-37999844 | chr1: 37033714-37272431 | kgp15160339 | kgp6185747 |
| GRM1 | chr6: 146348781-146758731 | chr6: 145848781-147258731 | chr6: 146390474-146800424 | kgp17333275 | rs17076442 |
| GRM3 | chr7: 86273229-86494192 | chr7: 85773229-86994192 | chr7: 86111165-86332128 | rs7809507 | rs6950721 |
| GRM5 | chr11: 88237743-88796816 | chr11: 87737743-89296816 | chr11: 87881005-88443664 | kgp11022062 | rs7123374 |
| GRM7 | chr3: 6902801-7783218 | chr3: 6402801-8283218 | chr3: 6877926-7758217 | rs17288121 | kgp10770379 |
| GRM8 | chr7: 126078651-126893147 | chr7: 125578651-127393147 | chr7: 125865887-126680383 | rs11767202 | kgp13721602 |
| GSN | chr9: 123963760-124095120 | chr9: 123463760-124595120 | chr9: 123003581-123134941 | rs10984984 | kgp10246924 |
| HOMER1 | chr5: 78669785-78809700 | chr5: 78169785-79309700 | chr5: 78705541-78845456 | kgp22480767 | rs2438612 |
| HTR2A | chr13: 47407512-47471169 | chr13: 46907512-47971169 | chr13: 46305513-46368995 | rs4942513 | rs2185411 |
| LARP7 | chr4: 113558119-113578742 | chr4: 113058119-114078742 | chr4: 113777568-113798191 | kgp20778198 | rs10516593 |
| MAPK1 | chr22: 22113946-22221970 | chr22: 21613946-22721970 | chr22: 20443946-20551970 | rs2019503 | rs5758017 |
| MTHFD1 | chr14: 64854758-64926725 | chr14: 64354758-65426725 | chr14: 63924845-63996812 | kgp8236539 | kgp19721535 |
| MX1 | chr21: 42792519-42831141 | chr21: 42292519-43331141 | chr21: 41714311-41753008 | rs7280789 | kgp9356591 |
| NARG1 | chr4: 140222675-140311935 | chr4: 139722675-140811935 | chr4: 140442125-140531385 | kgp951257 | kgp22761518 |
| NEGR1 | chr1: 71868624-72748405 | chr1: 71368624-73248405 | chr1: 71641212-72520993 | kgp15840593 | kgp15187386 |
| NLN | chr5: 65018022-65125111 | chr5: 64518022-65625111 | chr5: 65053840-65155115 | kgp8540617 | kgp6780911 |
| NMI | chr2: 152126981-152146430 | chr2: 151626981-152646430 | chr2: 151835227-151854676 | rs9789673 | rs4303715 |
| PCBP3 | chr21: 47063682-47355618 | chr21: 46563682-47855618 | chr21: 45888110-46180046 | rs13047590 | rs17371795 |
| PDE1C | chr7: 31792631-32338383 | chr7: 31292631-32838383 | chr7: 31759156-32305466 | rs960434 | rs10264489 |
| PPP2R1A | chr19: 52693054-52729678 | chr19: 52193054-53229678 | chr19: 57385045-57421483 | kgp3827878 | kgp21490256 |
| PRPSAP1 | chr17: 74306867-74350279 | chr17: 73806867-74850279 | chr17: 71818609-71861526 | kgp13936725 | kgp5222426 |
| PSMD11 | chr17: 30771501-30808042 | chr17: 30271501-31308042 | chr17: 27795614-27832155 | kgp12010810 | rs8065019 |
| PSMD13 | chr11: 236807-252984 | chr11: 1-752984 | chr11: 226807-242984 | kgp9815230 | kgp7252222 |
| PXN | chr12: 120648241-120703574 | chr12: 120148241-121203574 | chr12: 119132632-119187946 | kgp9790305 | kgp10851563 |
| QRICH2 | chr17: 74270129-74303761 | chr17: 73770129-74803761 | chr17: 71781724-71815356 | kgp9494493 | kgp13978344 |
| RANBP1 | chr22: 20105023-20114706 | chr22: 19605023-20614706 | chr22: 18485023-18494704 | kgp15081773 | kgp240898 |
| RAP2A | chr13: 98086474-98120252 | chr13: 97586474-98620252 | chr13: 96884476-96918245 | kgp1964422 | kgp12456635 |
| RCC1 | chr1: 28832454-28865708 | chr1: 28332454-29365708 | chr1: 28717331-28738194 | kgp4972332 | kgp10549261 |
| RGS12 | chr4: 3315873-3441640 | chr4: 2815873-3941640 | chr4: 3285671-3411438 | kgp1964422 | kgp12100218 |
| RIF1 | chr2: 152266396-152333860 | chr2: 151766396-152833860 | chr2: 151974645-152040665 | rs13010870 | kgp14366130 |
| RUVBL2 | chr19: 49497155-49519182 | chr19: 48997155-50019182 | chr19: 54188967-54210994 | kgp2866116 | rs6509434 |
| RYR1 | chr19: 38924339-39078204 | chr19: 38424339-39578204 | chr19: 43616179-43770044 | kgp21463042 | kgp10827233 |
| RYR2 | chr1: 237205701-237997288 | chr1: 236705701-238497288 | chr1: 235272678-236064265 | kgp15265824 | kgp855991 |
| SDC3 | chr1: 31342312-31381480 | chr1: 30842312-31881480 | chr1: 31114899-31154067 | kgp3545961 | rs1039630 |
| SELE | chr1: 169691780-169703220 | chr1: 169191780-170203220 | chr1: 167958404-167969844 | kgp11738441 | kgp5736867 |
| SERPINB9 | chr6: 2887503-2903545 | chr6: 2387503-3403545 | chr6: 2832502-2848506 | rs4959652 | kgp9198993 |
| SETD4 | chr21: 37415981-37451687 | chr21: 36915981-37951687 | chr21: 36337851-36373557 | rs8131794 | kgp10193814 |
| SGTB | chr5: 64961754-65017941 | chr5: 64461754-65517941 | chr5: 64997510-65053697 | rs2367239 | rs253229 |
| SHANK1 | chr19: 51165083-51220195 | chr19: 50665083-51720195 | chr19: 55856895-55912007 | kgp8880890 | kgp5265049 |
| SLC7A10 | chr19: 33699569-33716756 | chr19: 33199569-34216756 | chr19: 38391410-38408548 | kgp3880561 | kgp21532613 |
| SORD | chr15: 45315301-45367287 | chr15: 44815301-45867287 | chr15: 43102632-43154331 | rs3752691 | rs17627219 |
| STRAP | chr12: 16035287-16056410 | chr12: 15535287-16556410 | chr12: 15926554-15947677 | kgp9763258 | kgp18858589 |

TABLE 1-continued

Tier 1 mGluR network genes

| Tier 1 Gene | GeneRange (hg19) | GeneRange +500 kb(hg19) | GeneRange (hg18) | StartSNP (GeneRange +500 kb) | EndSNP (GeneRange +500 kb) |
|---|---|---|---|---|---|
| TK1 | chr17: 76170159-76183285 | chr17: 75670159-76683285 | chr17: 73681754-73694880 | kgp13960604 | kgp4569268 |
| TNIK | chr3: 170780291-171178197 | chr3: 170280291-171678197 | chr3: 172264363-172660546 | kgp17660929 | kgp3100328 |
| USP24 | chr1: 55532031-55681039 | chr1: 55032031-56181039 | chr1: 55304619-55453350 | kgp3052862 | kgp5594096 |
| VHL | chr3: 10183318-10195354 | chr3: 9683318-10695354 | chr3: 10158318-10168746 | kgp6652387 | rs9942062 |

TABLE 2

Tier 2 mGluR network genes

| Tier 2 | GeneRange(hg19) | GeneRange +500 kb(hg19) | GeneRange(hg18) | StartSNP | EndSNP |
|---|---|---|---|---|---|
| ACAT2 | chr6: 160182988-160200087 | chr6: 159682988-160700087 | chr12: 51783540-51804590 | kgp17016252 | rs3119312 |
| ACCN2 | chr12: 50451486-50477394 | chr12: 49951486-50977394 | chr12: 48737753-48763661 | kgp6083801 | kgp2326833 |
| ACP1 | chr2: 264868-278282 | chr2: 1-778282 | chr2: 254871-268282 | kgp14878812 | kgp6217001 |
| ACTB | chr7: 5566778-5570232 | chr7: 5066778-6070232 | chr7: 5533304-5536758 | kgp10503219 | rs17136342 |
| ADA | chr20: 43248162-43280376 | chr20: 42748162-43780376 | chr20: 42681576-42713790 | kgp505723 | rs2207199 |
| ADD1 | chr4: 2845583-2931802 | chr4: 2345583-3431802 | chr4: 2815381-2901587 | kgp5601859 | kgp5383382 |
| ADD2 | chr2: 70834749-70995375 | chr2: 70334749-71495375 | chr2: 70688257-70848837 | kgp14188216 | kgp4077094 |
| ADORA1 | chr1: 203096835-203136533 | chr1: 202596835-203636533 | chr1: 201363458-201403156 | rs16850143 | rs12568960 |
| ADRA1B | chr5: 159343739-159400017 | chr5: 158843739-159900017 | chr5: 159276317-159332595 | kgp17056747 | kgp2774549 |
| ADRA2A | chr10: 112836789-112840662 | chr10: 112336789-113340662 | chr10: 112826910-112830560 | kgp3219023 | rs10787379 |
| ADRA2 | chr4: 3768295-3770253 | chr4: 3268295-4270253 | chr4: 3737872-3740016 | kgp21189210 | kgp2132065 |
| ADRB2 | chr5: 148206155-148208197 | chr5: 147706155-148708197 | chr5: 148186348-148188381 | kgp6738042 | rs352336 |
| ANXA2 | chr15: 60639349-60690185 | chr15: 60139349-61190185 | chr15: 58426641-58477477 | kgp19904124 | kgp1248561 |
| APTX | chr9: 32972603-33001639 | chr9: 32472603-33501639 | chr9: 32962607-33015110 | kgp8123814 | rs2277875 |
| AQP1 | chr7: 30893009-30965131 | chr7: 30393009-31465131 | chr7: 30917992-30931656 | kgp13347683 | rs11983505 |
| ARHGAP24 | chr4: 86396283-86923823 | chr4: 85896283-87423823 | chr4: 86615307-87142847 | kgp12192788 | kgp20991115 |
| ARRB1 | chr11: 74971165-75062875 | chr11: 74471165-75562875 | chr11: 74654129-74740521 | kgp13077708 | kgp12867051 |
| ARRB2 | chr17: 4613788-4624795 | chr17: 4113788-5124795 | chr17: 4560537-4571544 | kgp10630047 | rs2304905 |
| BDKRB1 | chr14: 96722546-96731100 | chr14: 96222546-97231100 | chr14: 95792311-95800853 | rs10146784 | kgp10194056 |
| BTBD2 | chr19: 1985446-2015702 | chr19: 1485446-2515702 | chr19: 1936446-1966702 | kgp9698924 | rs12985186 |
| BTG2 | chr1: 203274663-203278729 | chr1: 202774663-201545352 | chr1: 201541286-201545352 | kgp11073362 | kgp22834576 |
| C17orf4 | chr17: 8123966-8127361 | chr17: 7623966-8627361 | chr17: 8064691-8068086 | kgp14083005 | kgp8066962 |
| C1orf116 | chr1: 207191865-207206101 | chr1: 206691865-207706101 | chr1: 205258488-205272724 | kgp15208593 | rs12094477 |
| C7orf25 | chr7: 42948871-42971805 | chr7: 42448871-43471805 | chr7: 42915396-42938330 | kgp13766903 | kgp8523923 |
| CALB2 | chr16: 71392615-71424342 | chr16: 70892615-71924342 | chr16: 69950126-69981843 | rs1774414 | kgp16319275 |
| CALM2 | chr2: 47387220-47403740 | chr2: 46887220-47903740 | chr2: 47146583-47257154 | kgp12094177 | kgp4237241 |
| CALM3 | chr14: 90863326-90874619 | chr14: 90363326-91374619 | chr19: 51796351-51805879 | kgp828819 | kgp22766175 |
| CAMK1 | chr3: 9799028-9811668 | chr3: 9299028-10311668 | chr3: 9774030-9786661 | kgp4340327 | kgp1318661 |
| CAMK2 | chr7: 44256748-44365230 | chr7: 43756748-44865230 | chr7: 44223273-44331749 | kgp10245456 | kgp1033822 |
| CAMK4 | chr5: 110559946-110820748 | chr5: 110059946-111320748 | chr5: 110587980-110848647 | kgp11981357 | kgp22673631 |
| CCNB1 | chr5: 68462836-68474070 | chr5: 67962836-68974070 | chr5: 68498668-68509826 | kgp5100830 | rs28529133 |
| CDC42 | chr1: 22379119-22419436 | chr1: 21879119-22919436 | chr1: 22251706-22292023 | kgp15282552 | rs209696 |
| CENTG1 | chr12: 58118076-58135944 | chr12: 57618076-58635944 | chr12: 56404343-56422211 | kgp22774357 | rs12825103 |
| CHGB | chr20: 5891973-5906005 | chr20: 5391973-6406005 | chr20: 5840167-5854003 | kgp19217529 | kgp5406173 |
| CHP | chr15: 41523436- | chr15: 41023436-42074083 | chr15: 39310728-39361375 | kgp9389002 | kgp1081542 |
| CHRM2 | chr7: 136553398-136701771 | chr7: 136053398-137201771 | chr7: 136203938-136352311 | rs2882248 | kgp11051162 |
| CMPK | chr2: 6988440-7005950 | chr2: 6488440-7505950 | chr2: 6905891-6923401 | rs16865056 | kgp6717309 |
| CNR1 | chr6: 88849584-88875767 | chr6: 88349584-89375767 | chr6: 88910155-88937281 | kgp11366911 | kgp5424340 |
| COPB2 | chr3: 139076432-139108522 | chr3: 138576432-139608522 | chr3: 140559122-140591212 | kgp17652827 | rs2554152 |
| CYCS | chr7: 25158269-25164980 | chr7: 24658269-25664980 | chr7: 25124799-25131480 | kgp22782658 | kgp9259047 |
| DCN | chr12: 91539034-91576806 | chr12: 91039034-92076806 | chr12: 90063165-90100937 | rs11105720 | rs1602946 |
| DHCR7 | chr11: 71145456-71159477 | chr11: 70645456-71659477 | chr11: 70823104-70837125 | rs2016495 | kgp4157665 |
| DLST | chr14: 75348593-75370450 | chr14: 74848593-75870450 | chr14: 74418371-74440198 | kgp6099186 | rs11621369 |
| DRD2 | chr11: 113280316-113346001 | chr11: 112780316-113846001 | chr11: 112785526-112851211 | kgp12732525 | rs1062613 |
| DRD3 | chr3: 113847556-113918254 | chr3: 113347556-114418254 | chr3: 115330246-115400944 | kgp18078164 | kgp7361746 |
| DSTN | chr20: 17550598-17588652 | chr20: 17050598-18088652 | chr20: 17498598-17536652 | kgp19350858 | rs1581925 |
| ECHS1 | chr10: 135175986-135186908 | chr10: 134675986-135686908 | chr10: 135025979-135036898 | kgp21664075 | kgp22837031 |
| EGFR | chr7: 55086724-55275031 | chr7: 54586724-55775031 | chr7: 55054218-55242525 | kgp12053718 | kgp3314724 |
| EIF3S3 | chr8: 117657055-117768062 | chr8: 117157055-118268062 | chr8: 117726236-117837243 | kgp10576753 | rs1793723 |
| ERBB2 | chr17: 37844392-37884915 | chr17: 37344392-38384915 | chr17: 35097918-35138441 | kgp11528115 | kgp670027 |
| F2R | chr5: 76011867-76031595 | chr5: 75511867-76531595 | chr5: 76047623-76067351 | kgp22518836 | kgp1549629 |
| F2RL2 | chr5: 75911306-75919240 | chr5: 75411306-76419240 | chr5: 75947062-75954996 | kgp10188048 | kgp8041699 |
| F2RL3 | chr19: 16999825-17002830 | chr19: 16499825-17502830 | chr19: 16860825-16863830 | kgp9756004 | kgp12567834 |
| F3 | chr1: 94994731-95007413 | chr1: 94494731-95507413 | chr1: 94767460-94779903 | kgp22732356 | kgp5203715 |
| FKBP3 | chr14: 45584801-45604009 | chr14: 45084801-46104009 | chr14: 44654858-44674272 | kgp8973198 | kgp19724486 |
| FSCN1 | chr7: 5632435-5646287 | chr7: 5132435-6146287 | chr7: 5598979-5612812 | kgp11535801 | kgp2273348 |
| FURIN | chr15: 91411884-91426687 | chr15: 90911884-91926687 | chr15: 89212888-89227691 | kgp19755110 | kgp7570879 |
| FYN | chr6: 111981534-112194655 | chr6: 111481534-112694655 | chr6: 112089177-112301320 | kgp9553033 | kgp10843976 |
| GLP1R | chr6: 39016556-39055520 | chr6: 38516556-39555520 | chr6: 39124534-39163498 | kgp11427391 | kgp8067157 |

TABLE 2-continued

Tier 2 mGluR network genes

| Tier 2 | GeneRange(hg19) | GeneRange +500 kb(hg19) | GeneRange(hg18) | StartSNP | EndSNP |
|---|---|---|---|---|---|
| GLP2R | chr17: 9729380-9793022 | chr17: 9229380-10293022 | chr17: 9670105-9733747 | kgp13857921 | kgp1409530 |
| GNAI1 | chr7: 79764139-79848725 | chr7: 79264139-80348725 | chr7: 79602075-79686661 | kgp3340161 | kgp96572 |
| GNAI3 | chr1: 110091185-110138452 | chr1: 109591185-110638452 | chr1: 109892708-109939975 | kgp28503409 | kgp2138201 |
| GNB2L1 | chr5: 180663927-180670906 | chr5: 180163927-181170906 | chr5: 180596533-180603512 | kgp9825803 | kgp22785368 |
| GOT1 | chr10: 101156626-101190530 | chr10: 100656626-101690530 | chr10: 101146617-101180336 | kgp21656902 | kgp21815940 |
| GP1BA | chr17: 4835591-4838325 | chr17: 4335591-5338325 | chr17: 4776371-4779067 | kgp13949132 | kgp1118664 |
| GPR26 | chr10: 125425870-125456913 | chr10: 124925870-125956913 | chr10: 125415860-125444113 | kgp7582662 | kgp21578542 |
| GRB2 | chr17: 73314156- | chr17: 72814156-73901790 | chr17: 70825751-70913385 | kgp13841089 | kgp1403521 |
| GRB7 | chr17: 37894161-37903538 | chr17: 37394161-38403538 | chr17: 35147712-35157064 | kgp14102913 | kgp13833584 |
| GRIA1 | chr5: 152870083-153193429 | chr5: 152370083-153693429 | chr5: 152850276-153173622 | rs1438937 | rs10057369 |
| GRM2 | chr3: 51741080-51752625 | chr3: 51241080-52252625 | chr3: 51716127-51727665 | rs4367100 | rs13060808 |
| GRM4 | chr6: 33989627-34113869 | chr6: 33489627-34613869 | chr6: 34097605-34231377 | kgp17076142 | rs6909637 |
| GRM6 | chr5: 178405329-178422124 | chr5: 177905329-178922124 | chr5: 178337935-178354730 | rs603852 | rs11249632 |
| HBXIP | chr1: 110943876-110950546 | chr1: 110443876-111450546 | chr1: 110745399-110752069 | kgp8686658 | rs1936942 |
| HD | chr6: 125596496-125623282 | chr6: 125096496-126123282 | chr6: 125638195-125664981 | rs11154263 | rs11967627 |
| HNRPA3 | chr2: 178077422-178088685 | chr2: 177577422-178588685 | chr2: 177785668-177796931 | kgp14203861 | rs1344924 |
| HOMER3 | chr19: 19017768-19045219 | chr19: 18517768-19545219 | chr19: 18901011-18912983 | rs13344313 | rs4808199 |
| HRPT2 | chr1: 193091088-193223942 | chr1: 192591088-193723942 | chr1: 191357711-191490565 | kgp2473538 | kgp12065536 |
| HSP90AB1 | chr6: 44214848-44221614 | chr6: 43714848-44721614 | chr6: 44322826-44329592 | kgp5836209 | kgp8706663 |
| IL8RB | chr2: 218989997-219001975 | chr2: 218489997-219501975 | chr2: 218698242-218710220 | kgp22730583 | rs1055816 |
| IMPDH2 | chr3: 49061761-49066875 | chr3: 48561761-49566875 | chr3: 49036765-49041879 | kgp22731595 | kgp5626213 |
| IQGAP2 | chr5: 75699148-76003957 | chr5: 75199148-76503957 | chr5: 75734904-76039713 | kgp22490664 | rs11739698 |
| ITGB1 | chr10: 33189245-33247293 | chr10: 32689245-33747293 | chr10: 33229251-33287299 | kgp12034252 | rs11009395 |
| ITGB7 | chr12: 53585106-53601000 | chr12: 53085106-54101000 | chr12: 51871373-51887267 | kgp19011413 | kgp3313746 |
| ITPR1 | chr3: 4535031-4889524 | chr3: 4035031-5389524 | chr3: 4510033-4864286 | kgp17889944 | rs1749057 |
| KIAA0090 | chr1: 19544583-19578046 | chr1: 19044583-20078046 | chr1: 19417170-19450633 | rs624761 | rs1009631 |
| KIAA1683 | chr19: 18367905-18385319 | chr19: 17867905-18885319 | chr19: 18228907-18246235 | kgp6435620 | rs10412356 |
| LAMA4 | chr6: 112429133-112575828 | chr6: 111929133-113075828 | chr6: 112535826-112682521 | kgp16962466 | kgp17024247 |
| LRP2BP | chr4: 186285031-186300172 | chr4: 185785031-186800172 | chr4: 186522026-186537166 | kgp7238414 | rs9994907 |
| LRRC59 | chr17: 48458593-48474914 | chr17: 47958593-48974914 | chr17: 45813597-45829831 | kgp1609816 | kgp13856216 |
| LTA | chr6: 2825414-2827639 | chr6: 2825414-2827639 | chr6: 2787675-2789683 | kgp11675228 | rs6912537 |
| LYAR | chr4: 4269428-4291896 | chr4: 3769428-4791896 | chr4: 4320337-4342744 | kgp22780996 | kgp7317116 |
| LYN | chr8: 56792385-56925006 | chr8: 56292385-57425006 | chr8: 56954930-57086494 | kgp8836202 | rs2670027 |
| MAP4 | chr3: 47892179-48130769 | chr3: 47392179-48630769 | chr3: 47867188-48105715 | kgp17741397 | rs35623035 |
| MAPT | chr17: 43971747-44105699 | chr17: 43471747-44605699 | chr17: 41327543-41461546 | kgp22730329 | kgp13941400 |
| MARK4 | chr19: 45754515-45808541 | chr19: 45254515-46308541 | chr19: 50446681-50500381 | kgp10230030 | kgp21456098 |
| MC4R | chr18: 58038563-58040001 | chr18: 57538563-58540001 | chr18: 56189543-56190981 | kgp7049183 | kgp1258536 |
| MGC11082 | chr18: 3602998-3604385 | chr18: 3102998-4104385 | chr18: 3592998-3594385 | kgp15965827 | kgp12318627 |
| MRPL14 | chr6: 44081372-44095191 | chr6: 43581372-44595191 | chr6: 44189349-44203169 | kgp17033193 | rs527322 |
| MRPS16 | chr10: 75006445-75012451 | chr10: 74506445-75512451 | chr10: 74678606-74682457 | kgp21628722 | rs12243089 |
| MTNR1A | chr4: 187454808-187476537 | chr4: 186954808-187976537 | chr4: 187619802-187713531 | rs12648771 | rs4476261 |
| MTNR1B | chr11: 92702788-92715948 | chr11: 92202788-93215948 | chr11: 92342436-92355596 | kgp10063029 | rs2658801 |
| MYC | chr8: 128748314-128753680 | chr8: 128248314-129253680 | chr8: 128817497-128822855 | kgp3177285 | kgp1944877 |
| MYO6 | chr6: 76458908-76629254 | chr6: 75958908-77129254 | chr6: 76515628-76685974 | kgp17262775 | kgp17183304 |
| NANS | chr9: 100818958-100845365 | chr9: 100318958-101345365 | chr9: 99847709-99885178 | kgp10817759 | rs2778908 |
| NCK1 | chr3: 136581049-136667968 | chr3: 136081049-137167968 | chr3: 138063762-138150658 | kgp117446 | kgp10600232 |
| NFKBIA | chr14: 35870715-35873960 | chr14: 35370715-36373960 | chr14: 34940466-34943711 | kgp19552677 | kgp19707730 |
| NPY2R | chr4: 156129780-156138228 | chr4: 155629780-156638228 | chr4: 156349230-156357678 | kgp3956236 | kgp20850236 |
| NUDC | chr1: 27248223-27272887 | chr1: 26748223-27772887 | chr1: 27145474-27170128 | rs11247955 | kgp1559749 |
| OPRD1 | chr1: 29138653-29190208 | chr1: 28638653-29690208 | chr1: 29011240-29062795 | kgp9104521 | kgp15855740 |
| PAFAH1B3 | chr19: 42801184-42806952 | chr19: 42301184-43306952 | chr19: 47493024-47498563 | kgp21540635 | kgp22735078 |
| PCBP1 | chr2: 70314584-70316334 | chr2: 69814584-70816334 | chr2: 70168204-70169836 | kgp14596264 | kgp6568959 |
| PCDHA4 | chr5: 140186671-140391929 | chr5: 139686671-140891929 | chr5: 140166855-140372115 | kgp6468526 | kgp10727572 |
| PCID1 | chr11: 32605313-32624037 | chr11: 32105313-33124037 | chr11: 32561889-32580613 | kgp13035948 | rs10836023 |
| PCMT1 | chr6: 150070830-150132557 | chr6: 149570830-150632557 | chr6: 150112657-150174249 | kgp17277449 | kgp10169289 |
| PDCD5 | chr19: 33072093-33078358 | chr19: 32572093-33578358 | chr19: 37763943-37770169 | kgp21531284 | rs7259333 |
| PDE1B | chr12: 54943176-54973023 | chr12: 54443176-55473023 | chr12: 53229670-53259290 | kgp18962385 | rs11171250 |
| PDE6G | chr17: 79617488-79623607 | chr17: 79117488-80123607 | chr17: 77227893-77234038 | kgp317116 | kgp13898509 |
| PGM1 | chr1: 64058946-64125916 | chr1: 63558946-64625916 | chr1: 63831534-63898505 | kgp175729 | kgp1541679 |
| PHKB | chr16: 47495209-47735434 | chr16: 46995209-48235434 | chr16: 46052710-46292935 | kgp8481371 | rs16945930 |
| PHKG2 | chr16: 30759619-30772497 | chr16: 30259619-31272497 | chr16: 30667237-30676183 | kgp16316196 | kgp22773724 |
| PICK1 | chr22: 38453261-38471708 | chr22: 37953261-38971708 | chr22: 36783207-36801654 | kgp5170623 | kgp1759680 |
| PIK3CA | chr3: 178866310-178952497 | chr3: 178366310-179452497 | chr3: 180349004-180435191 | rs7615444 | rs1025864 |
| PIK3R1 | chr5: 67511583-67597649 | chr5: 67011583-68097649 | chr5: 67547359-67633405 | kgp7844449 | rs7737296 |
| PLA2G7 | chr6: 46672052-46703430 | chr6: 46172052-47203430 | chr6: 46780011-46811110 | kgp4678268 | kgp9155835 |
| PLCB1 | chr20: 8113295-8865547 | chr20: 7613295-9365547 | chr20: 8061295-8813547 | kgp19226483 | rs2076234 |
| PLCB3 | chr11: 64018994-64036924 | chr11: 63518994-64536924 | chr11: 63775697-63793195 | kgp9427286 | rs484886 |
| PLCG2 | chr16: 81812898-81991899 | chr16: 81312898-82491899 | chr16: 80370430-80549400 | kgp4622733 | kgp3230988 |
| PPIH | chr1: 43124047-43142429 | chr1: 42624047-43642429 | chr1: 42896634-42915016 | kgp1870818 | rs11210802 |
| PRDX1 | chr1: 45976706-46988562 | chr1: 45476706-46488562 | chr1: 45749293-45760196 | rs3806405 | rs1556031 |
| PRKCA | chr17: 64298925-64806862 | chr17: 63798925-65306862 | chr17: 61729387-62237324 | kgp13847618 | kgp13994829 |
| PRLHR | chr10: 120352915-120355160 | chr10: 119852915-120855160 | chr10: 120342905-120345150 | rs853584 | kgp21690663 |
| PRMT1 | chr19: 50180408-50191707 | chr19: 49680408-50691707 | chr19: 54872307-54883516 | kgp1460116 | kgp5315133 |
| PSAT1 | chr9: 80912058-80945009 | chr9: 80412058-81445009 | chr9: 80101878-80134829 | kgp2581728 | kgp9769053 |
| PSEN1 | chr14: 73603142-73690399 | chr14: 73103142-74190399 | chr14: 72672931-72756862 | kgp8405661 | kgp19611371 |

TABLE 2-continued

Tier 2 mGluR network genes

| Tier 2 | GeneRange(hg19) | GeneRange +500 kb(hg19) | GeneRange(hg18) | StartSNP | EndSNP |
|---|---|---|---|---|---|
| PSMA1 | chr11: 14526421-14665180 | chr11: 14026421-15165180 | chr11: 14482997-14621739 | kgp12643195 | kgp13010596 |
| PSMC1 | chr14: 90722893-90738966 | chr14: 90222893-91238966 | chr14: 89792646-89808719 | rs10140098 | kgp19595798 |
| PSMD1 | chr2: 231921577-232037540 | chr2: 231421577-232537540 | chr2: 231629852-231745717 | rs1678155 | kgp11602861 |
| PSMD6 | chr3: 63996230-64009658 | chr3: 63496230-64509658 | chr3: 63971270-63984698 | kgp9706776 | kgp17718198 |
| PSME1 | chr14: 24605377-24608176 | chr14: 24105377-25108176 | chr14: 23675217-23678016 | kgp11494860 | kgp2234181 |
| PTHR2 | chr2: 209353736-209704818 | chr2: 208853736-210204818 | chr2: 209061981-209413063 | kgp14652386 | rs1020407 |
| PYGL | chr14: 51371934-51411248 | chr14: 50871934-51911248 | chr14: 50441686-50480984 | kgp10991856 | rs7146882 |
| PYGM | chr11: 64513860-64528187 | chr11: 64013860-65028187 | chr11: 64270436-64284763 | kgp12876954 | rs675671 |
| RAB2 | chr8: 61429469-61536203 | chr8: 60929469-62036203 | chr8: 61592023-61698757 | kgp7067636 | rs3864667 |
| RALA | chr7: 39663151-39747723 | chr7: 39163151-40247723 | chr7: 39629686-39714242 | kgp22733616 | rs11768838 |
| RCC2 | chr1: 17733250-17766250 | chr1: 17233250-18266250 | chr1: 17605865-17638807 | kgp15535308 | kgp7647703 |
| RGS2 | chr1: 192778168-192781407 | chr1: 192278168-193281407 | chr1: 191044793-191048026 | rs10921130 | kgp11065785 |
| RHOA | chr3: 49396578-49449526 | chr3: 48896578-49949526 | chr3: 49371582-49424530 | kgp11466037 | rs868891 |
| RPA2 | chr1: 28218048-28241236 | chr1: 27718048-28741236 | chr1: 28090635-28113823 | rs12033326 | kgp1570553 |
| RPLP2 | chr11: 809935-812876 | chr11: 309935-1312876 | chr11: 799935-802876 | kgp11473410 | kgp7750669 |
| RPN2 | chr20: 35807455-35870025 | chr20: 35307455-35370025 | chr20: 35240887-35303439 | kgp9846122 | kgp19260650 |
| RPS14 | chr5: 149823791-149829319 | chr5: 149323791-150329319 | chr5: 149803984-149809512 | kgp22444746 | kgp22218062 |
| RRM1 | chr11: 4137307-4223759 | chr11: 3637307-4723759 | chr11: 4072499-4116682 | rs6578398 | kgp4491491 |
| S100A6 | chr1: 153507075-153508717 | chr1: 153007075-154008717 | chr1: 151773699-151775341 | kgp15193014 | rs10908627 |
| SACS | chr13: 23902964-24007841 | chr13: 23402964-24507841 | chr13: 22800964-22905841 | kgp16818396 | rs2765089 |
| SARS | chr1: 109756514-109780804 | chr1: 109256514-110280804 | chr1: 109558062-109582308 | kgp5910329 | rs1803687 |
| SCTR | chr2: 120197418-120282028 | chr2: 119697418-120782028 | chr2: 119913888-119998498 | kgp12364473 | kgp22762988 |
| SET | chr9: 131445933-131458675 | chr9: 130945933-131958675 | chr9: 130485754-130498496 | kgp11282765 | kgp18608937 |
| SF3B14 | chr2: 24290453-24299314 | chr2: 23790453-24799314 | chr2: 24143957-24152818 | kgp14521970 | rs12474894 |
| SHBG | chr17: 7517381-7536700 | chr17: 7017381-8036700 | chr17: 7458106-7477395 | kgp7760759 | rs6503086 |
| SIAH1 | chr16: 48390274-48482309 | chr16: 47890274-48982309 | chr16: 46947777-47039810 | kgp4639784 | kgp7644930 |
| SLC2A1 | chr1: 43391045-43424847 | chr1: 42891045-43924847 | chr1: 43163632-43197434 | kgp2036523 | rs2782652 |
| SLC6A3 | chr5: 1392904-1445543 | chr5: 892904-1945543 | chr5: 1445909-1498538 | kgp22585075 | kgp9690399 |
| SNCA | chr4: 90645249-90759447 | chr4: 90145249-91259447 | chr4: 90865727-90978470 | kgp11552673 | kgp8195783 |
| SNRPB2 | chr20: 16710608-16722417 | chr20: 16210608-17222417 | chr20: 16658628-16670037 | kgp19326624 | kgp19208923 |
| SOCS6 | chr18: 67956136-67997434 | chr18: 67456136-68497434 | chr18: 66107116-66148414 | kgp10928836 | rs4243325 |
| SOCS7 | chr17: 36508006-36561846 | chr17: 36008006-33809545 | chr17: 33761530-33809545 | rs12936144 | rs4794796 |
| SRC | chr20: 35973087-36033821 | chr20: 35473087-36533821 | chr20: 35406501-35467235 | kgp19359278 | kgp9150551 |
| STAU1 | chr20: 47729875-47805288 | chr20: 47229875-48305288 | chr20: 47163282-47238695 | rs11905650 | kgp19233876 |
| STX12 | chr1: 28099693-28150963 | chr1: 27599693-28650963 | chr1: 27972280-28023550 | kgp22731625 | kgp1528794 |
| SYK | chr9: 93564011-93660842 | chr9: 93064011-94160842 | chr9: 92603890-92698304 | kgp12394293 | rs894962 |
| TBCA | chr5: 76986994-77072185 | chr5: 76486994-77572185 | chr5: 77022750-77107941 | rs2928164 | rs10059285 |
| TBXA2 | chr19: 3594503-3606831 | chr19: 3094503-4106831 | chr19: 3545503-3557658 | kgp21472781 | kgp1760692 |
| TCP1 | chr6: 160199529-160210735 | chr6: 159699529-160710735 | chr6: 160119519-160130725 | kgp16923201 | kgp10518192 |
| TEAD3 | chr6: 35441373-35464861 | chr6: 34941373-35964861 | chr6: 35549351-35572839 | rs847861 | kgp3339 |
| TFAM | chr10: 60145175-60155897 | chr10: 59815181-59825903 | chr10: 59815181-59825903 | kgp9406331 | kgp6514369 |
| TGM2 | chr20: 36756863-36793700 | chr20: 36256863-37293700 | chr20: 36190277-36227114 | rs6067098 | kgp9992037 |
| TJP1 | chr15: 29992356-30114706 | chr15: 29492356-30614706 | chr15: 27779648-27901998 | kgp19895791 | rs2604694 |
| TLR10 | chr4: 38773859-38784611 | chr4: 38273859-39284611 | chr4: 38450646-38460984 | kgp9612652 | rs6531705 |
| TMEM4 | chr12: 56704213-56710128 | chr12: 56204213-57210128 | chr12: 54990480-54996395 | kgp6718939 | kgp6565807 |
| TPI1 | chr12: 6976583-6980110 | chr12: 6476583-7480110 | chr12: 6846966-6850253 | kgp3883976 | kgp1884905 |
| TRAF2 | chr9: 139776384-139821067 | chr9: 139276384-140321067 | chr9: 138896205-138940888 | rs3812570 | kgp9465784 |
| TRMT1 | chr11: 64084164-64085033 | chr11: 63584164-64585033 | chr11: 63840740-63841609 | kgp1242205 | rs2957154 |
| TUBA1 | chr12: 49521565-49525304 | chr12: 49021565-50025304 | chr12: 47807832-47811571 | kgp4948752 | kgp18737983 |
| TUBA1A | chr12: 49578582-49582861 | chr12: 49078582-50082861 | chr12: 47864849-47869128 | kgp5373125 | kgp1407179 |
| TUBA1B | chr12: 49521566-49525304 | chr12: 49021566-50025304 | chr12: 47807832-47866883 | kgp4948752 | kgp18737983 |
| TUBA2 | chr12: 49578793-49580616 | chr12: 49078793-50080616 | chr12: 47865060-47866883 | kgp18983720 | kgp75177 |
| TUBB | chr6: 1981087-1986127 | chr6: 1481087-2486127 | chr6: 1935034-1940074 | kgp17000846 | kgp16908954 |
| TUBG1 | chr17: 40761357-40767256 | chr17: 40261357-41267256 | chr17: 38015219-38020777 | rs12600570 | kgp3534380 |
| TXN | chr9: 113006091-113018920 | chr9: 112506091-113518920 | chr9: 112046130-112058599 | kgp18601393 | kgp652846 |
| TXNDC4 | chr9: 102741463-102861330 | chr9: 102241463-103361330 | chr9: 101781284-101901151 | kgp22740558 | rs10989168 |
| TXNL2 | chr10: 131934639-131977932 | chr10: 131434639-132477932 | chr10: 131824629-131867922 | kgp21587397 | rs2921907 |
| TYMS | chr18: 657603-673499 | chr18: 157603-1173499 | chr18: 647603-663499 | kgp1671520 | kgp5560925 |
| UBQLN4 | chr1: 156005091-156023516 | chr1: 155505091-156523516 | chr1: 154271715-154290140 | rs12746592 | kgp204451 |
| UCHL1 | chr4: 41258897-41270446 | chr4: 40758897-41770446 | chr4: 40953685-40965203 | rs10029833 | kgp2115771 |
| VIPR1 | chr3: 42530790-42579065 | chr3: 42030790-43079065 | chr3: 42519120-42554064 | rs794894 | kgp1077139 |
| YWHA | chr2: 9724105-9771106 | chr2: 9224105-10271106 | chr2: 9641556-9688557 | kgp7327726 | rs1138729 |
| ZAP70 | chr2: 98330030-98356323 | chr2: 97830030-98856323 | chr2: 97696462-97722755 | kgp10723114 | kgp1430880 |

The primary analysis of the non-interventional study was to estimate the prevalence of copy number variations (CNVs) in mGluR network genes within this population of children/adolescents with ADHD.

Exploratory analyses were based on phenotype analysis of cohorts that were defined by CNV status of either CNV-positive or CNV-negative for CNVs in mGluR network genes. CNV status was assessed in relation to demographics; psychiatric comorbidity; current behavioral concerns; past medical history: development/education history; ADHD pharmacotherapy (current/past); ADHD behavioral therapy (current/past); other psychiatric medications (current/pest) of the patient. In addition, CNV status was assessed in relation to the psychiatric history of the patient's immediate family (mother, family, and siblings).

Post-hoc analysis included subset analyses based on CNVs in a single mGluR network gene. Based on data from this study that will be described below, a post-hoc analysis was performed for CNTN4.

Figure 1:
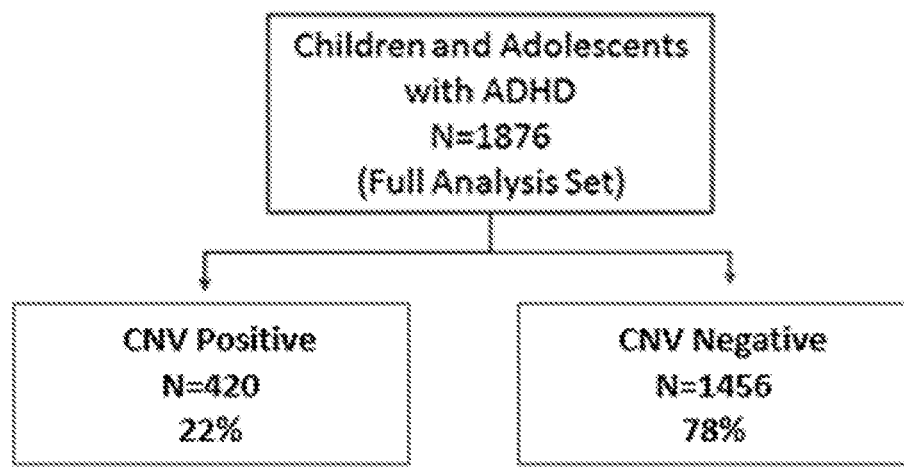
FIG. 1 shows data on the number of children and adolescents enrolled in the non-interventional study. "CNV positive" indicates that the subject had one or more copy number variant (CNV) in one of the 273 mGluR network genes listed in Tables 1-2. "CNV negative" patients did not have a CNV in any of these 273 genes.

FIG. 1 represents data on patients that were enrolled in the study. Of a total of 1876 patients, 22% were positive for a CNV in a mGluR network gene.

Demographic data on enrolled subjects are presented in Table 3. "Positive" CNV status indicates that a subject had one or CNVs in one or more of the genes listed in Tables 1 or 2, and these subjects are the "CNV-positive cohort." "Negative" CNV status indicates that a subject had no CNVs in any gene listed in Tables 1 or 2, and these subjects are the "CNV-negative cohort."

TABLE 3

Demographics of enrolled subjects

| | CNV Status | | | |
|---|---|---|---|---|
| | Positive (N = 420) | | Negative (N = 1456) | |
| | N | % subjects | N | % subjects |
| Age Group | | | | |
| 6-11 yrs | 76 | 18% | 216 | 15% |
| 12-17 yrs | 344 | 82% | 1240 | 85% |
| Gender, male | 276 | 66% | 994 | 68% |
| Race* | | | | |
| White | 254 | 60% | 1158 | 80% |
| Black/African-American | 164 | 39% | 298 | 20% |
| Other | 33 | 8% | 68 | 5% |
| ADHD Presentation | | | | |
| Combined | 312 | 74% | 1088 | 75% |
| Hyperactive | 13 | 3% | 53 | 4% |
| Inattentive | 95 | 23% | 315 | 22% |

*Subjects of multiple races were included in "other" category.

No notable differences between cohorts were seen in demographic parameters other than race. A higher percentage of African-American/black subjects were found in the CNV-positive cohort.

Also, no notable differences were found between cohorts in past medical history or comorbidities commonly associated with ADHD (opposition defiant/conduct disorder, autism spectrum disorder, tics/Tourette's, learning disabilities, anxiety disorders, depression).

Based on assessment of parent/sibling psychiatric history, the only notable differences were higher rate of paternal history of developmental disability/delay ($p \leq 0.05$) and marginally ($p = 0.06$) higher rate of sibling ADHD in CNV-positive subjects.

Figure 2:
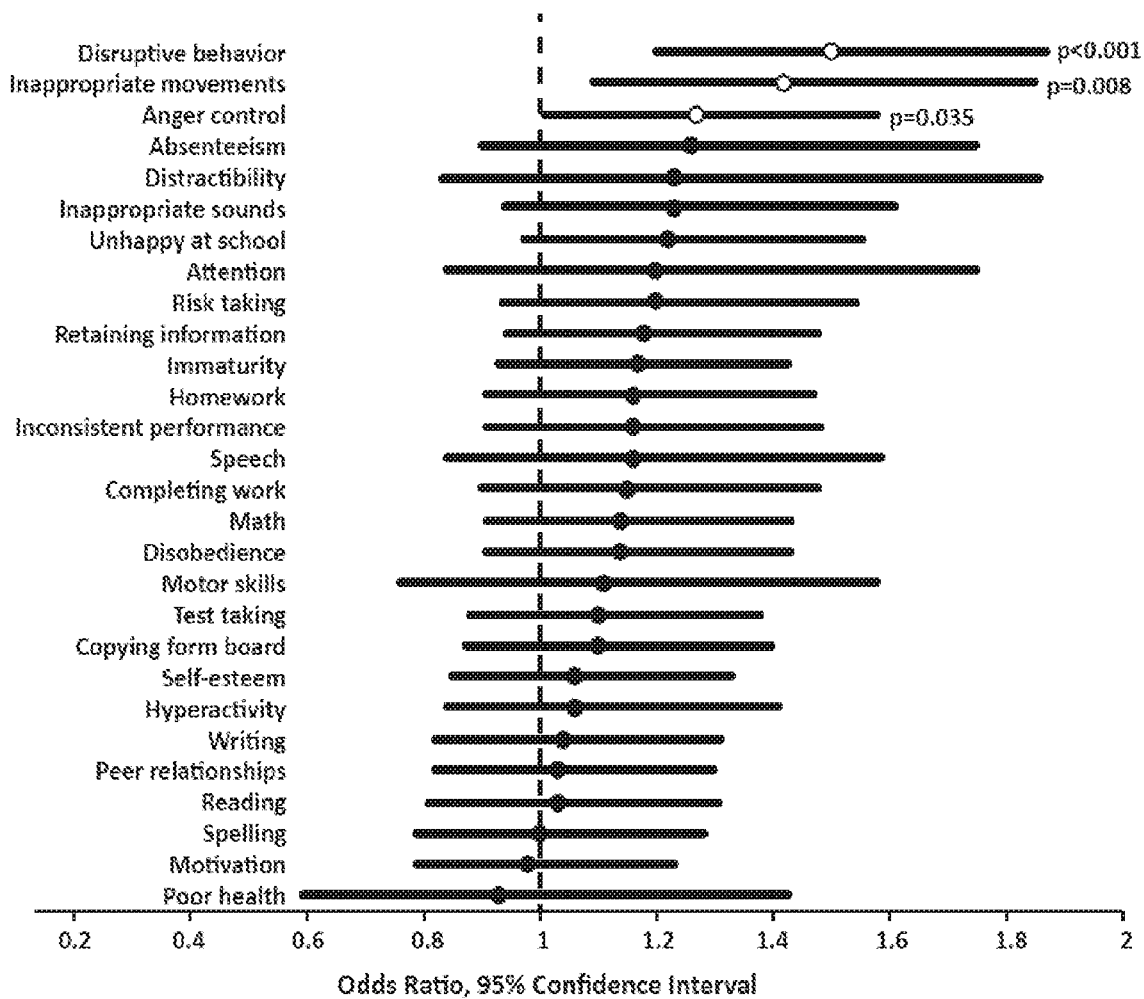
FIG. 2 shows the odds ratio (OR) of current behavioral concerns listed by parents of subjects in the CNV-positive cohort compared to the CNV-negative cohorts. An OR greater than 1 indicates that a behavioral concern was more frequent in the CNV-positive cohort.

FIG. 2 presents the odds ratio (OR) of current behavioral concerns listed by parents of subjects in relation to the CNV-positive or CNV-negative cohorts. A higher OR indicates a greater frequency of the behavior within the CNV-positive cohort. Current behavioral concerns positively associated with the CNV-positive cohort were disruptive behavior ($p < 0.001$), inappropriate movements ($p = 0.008$), and anger control ($p < 0.0^{35}$).

CNTN4 was the most commonly-mutated gene of interest (N=92 subjects), comprising 22% of the CNV-positive population.

Table 4 lists the location of CNVs in subjects in the non-interventional study with CNVs in CA7N4. Some individuals in the study may have harbored more than one CNV. These subjects are included in the listing below, but not included in the 92-subject statistical analysis referenced above. Note that the table includes duplicates. That is, some of the rows report the same CNV. We retained the duplicates for at least the reason that it may be informative to know the frequency of particular CNTN4 CNVs in the tested population.

TABLE 4

Location of CNVs in CNTN4 in non-interventional study

| Type of CNV | Start-End of CNV |
|---|---|
| Deletion | chr3: 2381839-2476577 |
| Deletion | chr3: 1917909-1920416 |
| Deletion | chr3: 1936873-1944855 |
| Deletion | chr3: 1913371-1925851 |
| Duplication | chr3: 2212759-2473281 |
| Deletion | chr3: 1917909-1922565 |
| Deletion | chr3: 2023020-2028135 |
| Duplication | chr3: 2572993-2574706 |
| Deletion | chr3: 1936873-1944855 |
| Deletion | chr3: 1917909-1922565 |
| Deletion | chr3: 1917909-1922565 |
| Deletion | chr3: 1917909-1922565 |
| Deletion | chr3: 1918149-1922565 |
| Deletion | chr3: 1936873-1944855 |
| Deletion | chr3: 1912520-1925851 |
| Deletion | chr3: 1913371-1925851 |
| Deletion | chr3: 2947575-2953111 |
| Deletion | chr3: 1936873-1944855 |
| Deletion | chr3: 1936873-1944855 |
| Deletion | chr3: 1936873-1945563 |
| Deletion | chr3: 1936873-1944855 |
| Deletion | chr3: 1928752-1968641 |
| Deletion | chr3: 1936873-1944855 |
| Deletion | chr3: 1918149-1920416 |
| Deletion | chr3: 1917909-1920416 |
| Deletion | chr3: 1917909-1922565 |
| Deletion | chr3: 2346871-2403275 |
| Deletion | chr3: 1918149-1922565 |
| Deletion | chr3: 1917909-1920416 |
| Deletion | chr3: 1917909-1922565 |
| Deletion | chr3: 1936873-1944855 |
| Deletion | chr3: 1917909-1922565 |
| Deletion | chr3: 1917909-1922565 |
| Deletion | chr3: 1913371-1926058 |
| Deletion | chr3: 2669708-3050406 |
| Deletion | chr3: 1936873-1944855 |
| Deletion | chr3: 1917909-1922565 |
| Deletion | chr3: 2409519-2422385 |
| Deletion | chr3: 1917909-1922565 |
| Deletion | chr3: 1917909-1920416 |
| Deletion | chr3: 1913371-1925851 |
| Deletion | chr3: 2764220-2766604 |
| Deletion | chr3: 1917909-1922565 |
| Deletion | chr3: 2748076-2751249 |
| Deletion | chr3: 2748076-2751249 |
| Duplication | chr3: 2569261-2574706 |
| Duplication | chr3: 2572993-2574706 |
| Duplication | chr3: 2567829-2574706 |
| Deletion | chr3: 2765286-2769230 |
| Deletion | chr3: 1936873-1944855 |
| Deletion | chr3: 1917909-1922565 |
| Deletion | chr3: 1917909-1922565 |
| Deletion | chr3: 1917909-1922565 |
| Deletion | chr3: 1917909-1922565 |
| Deletion | chr3: 1917909-1922565 |
| Deletion | chr3: 1917909-1922565 |
| Deletion | chr3: 1917909-1922565 |
| Deletion | chr3: 1917909-1922565 |
| Deletion | chr3: 1936873-1944855 |
| Deletion | chr3: 1917909-1920416 |
| Duplication | chr3: 2595938-2744952 |
| Deletion | chr3: 2229166-2233338 |
| Duplication | chr3: 2567829-2574706 |
| Deletion | chr3: 1936873-1945563 |
| Deletion | chr3: 1917909-1922565 |
| Deletion | chr3: 2086416-2111940 |

TABLE 4-continued

Location of CNVs in CNTN4 in non-interventional study

| Type of CNV | Start-End of CNV |
|---|---|
| Duplication | chr3: 2567829-2574706 |
| Deletion | chr3: 1917909-1922565 |
| Duplication | chr3: 2572993-2574706 |
| Deletion | chr3: 1917909-1920416 |
| Deletion | chr3: 1936873-1944855 |
| Deletion | chr3: 1872119-1932203 |
| Deletion | chr3: 1872119-1932203 |
| Deletion | chr3: 1936873-1944855 |
| Deletion | chr3: 1917909-1920416 |
| Deletion | chr3: 1917909-1920416 |
| Deletion | chr3: 1899050-1971129 |
| Deletion | chr3: 1917909-1922565 |
| Deletion | chr3: 1918149-1922565 |
| Duplication | chr3: 2572993-2574706 |
| Duplication | chr3: 2572993-2574706 |
| Deletion | chr3: 1913371-1917400 |
| Deletion | chr3: 1917909-1922565 |
| Deletion | chr3: 1917909-1922565 |
| Duplication | chr3: 2035573-2202059 |
| Deletion | chr3: 1917909-1922565 |
| Duplication | chr3: 2567829-2574706 |
| Deletion | chr3: 1936873-1944855 |
| Deletion | chr3: 1917909-1922565 |
| Deletion | chr3: 1917909-1922565 |
| Deletion | chr3: 1917909-1922565 |
| Deletion | chr3: 1145301-2937380 |
| Deletion | chr3: 1913371-1925401 |
| Deletion | chr3: 1913371-1925851 |
| Deletion | chr3: 1913371-1925851 |
| Deletion | chr3: 1917909-1922565 |
| Deletion | chr3: 1913776-1917909 |
| Deletion | chr3: 1917909-1922565 |
| Deletion | chr3: 1917909-1922565 |
| Deletion | chr3: 1918149-1922565 |

In conclusion, 22% of subjects in a clinical sample of 1876 children and adolescents with ADHD had CNVs in glutamatergic network and neuronal connectivity genes of interest. CNV-positive and CNV-negative subjects were clinically similar, although parents identified disruptive behaviors, inappropriate movements, and anger control as clinical concerns in significantly more CNV-positive subjects. This finding may have been driven, in large part, by the relatively large number of CNV-positive subjects with CNTN4 CNVs. CNTN4 encodes an axon-associated cell adhesion molecule important in neuronal network formation and plasticity.

Example 2—Posthoc Analysis of Subjects with and without Mutations in CNTN4 in the Non-Interventional Study of Glutamatergic Network Gene CNVs in Children and Adolescents with ADHD Further post-hoc analysis of a subset of the Full Analysis Set was also performed using data from the non-interventional study. The subset included subjects with mutations in the CNTN4 gene (CNTN4-positive subjects) and subjects with no metabotropic glutamate receptor (mGluR) mutations (mGluR-negative subjects), which included a total of 1,548 subjects. The planned analyses for this study were repeated for the comparison of CNTN4-positive subjects with mnGluR-negative subjects, with the exception of the summary of subject disposition and estimates of attention-deficit hyperactivity disorder (ADHD) prevalence using Bayesian probabilities.

The numbers and percentages of subjects who were CNTN4-positive or mGluR-negative by age group and overall are shown in Table 5. A total of 92 (5.9%) of the 1,548 subjects in this subset were CNTN4-positive. The percentage of pediatric subjects (6 to 11 years of age) who were CNTN4-positive (8.1%) was slightly higher than the percentage of adolescent subjects (12 to 17 years of age) who were CNTN4-positive.

TABLE 5

Numbers and Percentages of Subjects who were CNTN4-positive or mGluR-negative by Age Group and Overall

| | CNTN4-positive n (%) | No mGluR Mutation n (%) | Overall n (%) |
|---|---|---|---|
| Full Analysis Set | 92 (5.9) | 1456 (94.1) | 1548 (100) |
| Children (6-11 years) | 19 (8.1) | 216 (91.9) | 235 (15.2) |
| Adolescents (12-17 years) | 73 (5.6) | 1240 (94.4) | 1313 (84.8) |

Note:
Percentages are 100*n/N.

Table 6 summarizes demographic and baseline disease characteristics for CNTN4-positive and mGluR-negative subjects.

TABLE 6

Demographic and Baseline Characteristics for the Subset of Subjects who were CNTN4-positive or mGluR-negative

| Parameter Category | CNTN4-Positive Subjects (N = 92) n (%) | No mGluR Mutation (N = 1456) n (%) | Overall (N = 1548) n (%) |
|---|---|---|---|
| Age (Years) | | | |
| n | 92 | 1456 | 1548 |
| Mean | 12.9 | 13.4 | 13.4 |
| Standard Deviation | 2.74 | 2.40 | 2.43 |
| Median | 13.5 | 14.0 | 14.0 |
| Minimum, Maximum | 6, 17 | 6, 17 | 6, 17 |
| Gender | | | |
| Male | 57 (62.0%) | 994 (68.3%) | 1051 (67.9%) |
| Female | 35 (38.0%) | 462 (31.7%) | 497 (32.1%) |
| Ethnicity | | | |
| Hispanic or Latino | 8 (8.7%) | 212 (14.6%) | 220 (14.2%) |
| Not Hispanic or Latino | 84 (91.3%) | 1229 (84.4%) | 1313 (84.8%) |
| Not Reported | 0 | 15 (1.0%) | 15 (1.0%) |
| Race | | | |
| American Indian or Alaska Native | 0 | 5 (0.3%) | 5 (0.3%) |
| Asian | 0 | 13 (0.9%) | 13 (0.8%) |
| Black or African American | 60 (65.2%) | 257 (17.7%) | 317 (20.5%) |
| Native Hawaiian or Other Pacific Islander | 0 | 3 (0.2%) | 3 (0.2%) |
| White | 22 (23.9%) | 1101 (75.6%) | 1123 (72.5%) |
| Multiple | 8 (8.7%) | 60 (4.1%) | 68 (4.4%) |
| Other | 2 (2.2%) | 17 (1.2%) | 19 (1.2%) |
| ADHD Subtype | | | |
| Combined | 72 (78.3%) | 1088 (74.7%) | 1160 (74.9%) |
| Hyperactive | 3 (3.3%) | 53 (3.6%) | 56 (3.6%) |
| Inattentive | 17 (18.5%) | 315 (21.6%) | 332 (21.4%) |
| Age at Which ADHD Diagnosed (years) | | | |
| n | 92 | 1456 | 1548 |
| Mean | 7.8 | 7.9 | 7.9 |
| Standard Deviation | 3.01 | 2.92 | 2.93 |
| Median | 7.0 | 7.0 | 7.0 |
| Minimum, Maximum | 2, 16 | 2, 17 | 2, 17 |

Note:
Percentages are 100*n/N.

Demographic and baseline characteristics were similar for CNTN4-positive subjects and mGluR-negative subjects with the exception of race. The mean (standard deviation [SD]1) age of subjects in this subset was 13.4 (2.43) years. The majority of subjects were male (67.9%) and not Hispanic or Latino (84.8%). The majority of subjects were diagnosed with the combined ADHD subtype (74.9%); the mean (SD) age at diagnosis was 7.9 (2.93) years. The percentage of subjects who were black was higher among CNTN4-positive subjects (65.2%) than among mGluR-negative subjects (17.7%).

Table 7 summarizes the numbers and percentages of subjects ever prescribed various ADHD therapies for CNTN4-positive and mGluR-negative subjects.

TABLE 7

Summary of ADHD Therapies Ever Prescribed for the Subset of Subjects who were CNTN4-positive or mGluR-negative

| Category Therapy | CNTN4-positive (N = 92) n (%) | No mGluR Mutation (N = 1456) n (%) | Overall (N = 1548) n (%) |
| --- | --- | --- | --- |
| Subjects who were Ever Prescribed ADHD Therapy | 83 (90.2%) | 1368 (94.0%) | 1451 (93.7%) |
| Stimulant | 80 (87.0%) | 1274 (87.5%) | 1354 (87.5%) |
| Methylphenidate, Long Acting | 51 (55.4%) | 812 (55.8%) | 863 (55.7%) |
| Methylphenidate, Short Acting | 22 (23.9%) | 378 (26.0%) | 400 (25.8%) |
| Amphetamine, Long Acting | 46 (50.0%) | 809 (55.6%) | 855 (55.2%) |
| Amphetamine, Short Acting | 18 (19.6%) | 261 (17.9%) | 279 (18.0%) |
| Non-Stimulant | 23 (25.0%) | 545 (37.4%) | 568 (36.7%) |
| Atomoxetine | 11 (12.0%) | 244 (16.8%) | 255 (16.5%) |
| Clonidine, Long Acting | 2 (2.2%) | 68 (4.7%) | 70 (4.5%) |
| Clonidine, Short Acting | 4 (4.3%) | 123 (8.4%) | 127 (8.2%) |
| Guanfacine, Long Acting | 8 (8.7%) | 249 (17.1%) | 257 (16.6%) |
| Guanfacine, Short Acting | 7 (7.6%) | 93 (6.4%) | 100 (6.5%) |
| Other Medications for Psychiatric Conditions | 24 (26.1%) | 420 (28.8%) | 444 (28.7%) |
| Anti-depressants | 17 (18.5%) | 366 (25.1%) | 383 (24.7%) |
| Neuroleptics | 13 (14.1%) | 189 (13.0%) | 202 (13.0%) |
| ADHD Behavioral Therapy | 56 (60.9%) | 797 (54.7%) | 853 (55.1%) |
| Behavioral Treatment | 34 (37.0%) | 422 (29.0%) | 456 (29.5%) |
| Psychotherapy | 32 (34.8%) | 477 (32.8%) | 509 (32.9%) |
| Family Therapy with Child | 18 (19.6%) | 356 (24.5%) | 374 (24.2%) |
| Inpatient Evaluation/Treatment | 8 (8.7%) | 117 (8.0%) | 125 (8.1%) |
| ADHD Coaching | 9 (9.8%) | 94 (6.5%) | 103 (6.7%) |
| ADHD Video Games/Cognitive Training | 2 (2.2%) | 51 (3.5%) | 53 (3.4%) |

Note:
Percentages are 100*n/N. A subject was counted only 1 time per individual therapy listed. Subjects who participated in multiple therapies were counted 1 time for each therapy Over 90% of subjects in this subset had previously been prescribed an ADHD therapy. The percentages of subjects previously prescribed stimulants (87.5%) were similar for CNTN4-positive subjects and mGluR-negative subjects. However, within this category, the percentage of CNTN4-positive subjects ever prescribed long-acting amphetamines (50.0%) was lower than the percentage calculated for mGluR-negative subjects (55.6%).

The percentage of subjects previously prescribed non-stimulant therapy was lower among CNTN4-positive subjects (25.0%) than among mGluR-negative subjects (37.4%). This difference was largely accounted for by percentages of CNTN4-positive subjects prescribed atomoxetine (12.0%) or long-acting guanfacine (8.7%) that were lower than percentages of mGluR-negative subjects identified as receiving these therapies (16.8% and 17.1%, respectively).

The percentages of subjects ever prescribed other medications for psychiatric conditions were similar for CNTN4-positive subjects (26.1%) and mGluR-negative subjects (28.8%). However, within this category, the percentage of CNTN4-positive subjects previously prescribed anti-depressants (18.5%) was lower than this percentage in mGluR-negative subjects (25.1%).

The percentage of CNTN4-positive subjects who were prescribed ADHD behavioral therapy was higher (60.9%) than the percentage of mGluR-negative subjects previously prescribed ADHD behavioral therapy (54.7%). This difference was largely accounted for by the higher percentage of behavioral treatment prescribed among CNTN4-positive subjects (37.0%) than among mGluR-negative subjects (29.0%).

There were no notable differences in reported positive medical histories between CNTN4-positive subjects and mGluR-negative subjects. Positive medical histories analyzed included congenital structural heart disease, arrhythmia, head injury, seizures, meningitis/encephalitis, and headaches.

Psychiatric histories were also assessed, including psychiatric histories for alcohol abuse, anxiety disorders, autism spectrum disorder, cigarette smoking, depression, drug/substance abuse, eating disorders, learning disabilities, oppositional defiant disorder/conduct disorder, psychosis, and tics/Tourette's syndrome in CNTN4-positive and mGluR-negative subjects. With the exception of oppositional defiant disorder/conduct disorder, there were no notable ditTerences between CNTN4-positive subjects and mGluR-negative subjects in the reported psychiatric histories evaluated, which represent comorbidities commonly associated with ADHD. Oppositional defiant disorder/conduct disorder was reported more frequently for CNTN4-positive subjects (28.3%) than in mGluR-negative subjects (17.2%; p=0.0109).

Specific psychiatric histories for the subjects' mothers, fathers, and siblings for CNTN4-positive and mGluR-negative subjects were also evaluated. Specific psychiatric histories evaluated included ADHD, alcohol abuse, anxiety disorders, autism spectrum disorder, cigarette smoking, depression, developmental disability/delay, drug/substance abuse, eating disorders, learning disabilities, oppositional defiant disorder/conduct disorder, psychosis, tics/Tourette's syndrome, and schizophrenia.

Notable differences in psychiatric family history in the subset are summarized in Table 8. A higher rate of reported maternal history of alcohol abuse was seen in CNTN4-positive subjects (14.1%) than in mGluR-negative subjects (7.0%; p-0.0208). A higher rate of reported paternal history of depression was seen in CNTN4-positive subjects (30.4%) than in mGluR-negative subjects (19.0%; p=0.0088). A higher rate of reported maternal history of developmental disability/delay was seen in CNTN4-positive subjects (5.4%) than in mGluR-negative subjects (1.9%; p-0.0362). A higher rate of reported paternal history of developmental disability/delay was seen in CNTN4-positive subjects (6.5%) than in mGluR-negative subjects (2.5%; p=0.0340). A higher rate of reported maternal history of drug/substance abuse was seen in CNTN4-positive subjects (18.5%) than in mGluR-negative subjects (8.6%; p-0.0041). A higher rate of reported paternal history of drug/substance abuse was seen in CNTN4-positive subjects (23.9%) than in mGluR-negative subjects (15.2%; p=0.0367). A higher rate of reported paternal history of oppositional defiant disorder/conduct disorder was seen in CNTN4-positive subjects (13.0%) than in mGluR-negative subjects (5.4%; p=0.0086). A higher rate of reported sibling history of oppositional defiant disorder/conduct disorder was seen in CNTN4-positive subjects (23.9%) than in mGluR-negative subjects (11.5%; p=0.0014).

Notable differences in psychiatric histories in either parent for CNTN4-positive and mGluR-negative subjects are summarized in Table 9. A higher rate of reported parental history of developmental disability/delay was seen in CNTN4-positive subjects (12.0%) than in mGluR-negative subjects (4.0%: p=0.0017). A higher rate of reported parental drug/substance abuse was seen in CNTN4-positive subjects (35.9%) than in mGluR-negative subjects (18.7%; p=0.0002). A higher rate of reported parental history of oppositional defiant disorder/conduct disorder was seen in CNTN4-positive subjects (17.4%) than in mGluR-negative subjects (7.5%; p=0.0021).

TABLE 8

Selected Psychiatric Family History (Mother, Father, or Sibling) for the Subset of Subjects who were CNTN4-positive or mGluR-negative

| Parameter Category | CNTN4-positive ADHD Subjects (N = 92) | ADHD Subjects without mGluR Mutation (N = 1456) | P-value[a] | OR[b] | 95% CI[b] |
|---|---|---|---|---|---|
| Alcohol Abuse - Mother | | | | | |
| Yes | 13 (14.1%) | 102 (7.0%) | 0.0208 | 2.20 | (1.08, 4.15) |
| No | 77 (83.7%) | 1328 (91.2%) | — | — | — |
| Not applicable | 2 (2.2%) | 26 (1.8%) | — | — | — |
| Depression - Father | | | | | |
| Yes | 28 (30.4%) | 277 (19.0%) | 0.0088 | 1.92 | (1.15, 3.12) |
| No | 59 (64.1%) | 1120 (76.9%) | — | — | — |
| Not applicable | 5 (5.4%) | 59 (4.1%) | — | — | — |
| Developmental Disability/Delay - Mother | | | | | |
| Yes | 5 (5.4%) | 27 (1.9%) | 0.0362 | 3.07 | (0.90, 8.36) |
| No | 84 (91.3%) | 1393 (95.7%) | — | — | — |
| Not applicable | 3 (3.3%) | 36 (2.5%) | — | — | — |
| Developmental Disability/Delay - Father | | | | | |
| Yes | 6 (6.5%) | 36 (2.5%) | 0.0340 | 2.77 | (0.93, 6.89) |
| No | 82 (89.1%) | 1362 (93.5%) | — | — | — |
| Not applicable | 4 (4.3%) | 58 (4.0%) | — | — | — |
| Drug/Substance Abuse - Mother | | | | | |
| Yes | 17 (18.5%) | 125 (8.6%) | 0.0041 | 2.42 | (1.30, 4.31) |
| No | 73 (79.3%) | 1301 (89.4%) | — | — | — |
| Not applicable | 2 (2.2%) | 30 (2.1%) | — | — | — |
| Drug/Substance Abuse - Father | | | | | |
| Yes | 22 (23.9%) | 221 (15.2%) | 0.0367 | 1.76 | (1.01, 2.96) |
| No | 67 (72.8%) | 1184 (81.3%) | — | — | — |
| Not applicable | 3 (3.3%) | 51 (3.5%) | — | — | — |
| Oppositional Defiant Disorder/Conduct Disorder - Father | | | | | |
| Yes | 12 (13.0%) | 78 (5.4%) | 0.0086 | 2.67 | (1.27, 5.21) |
| No | 76 (82.6%) | 1321 (90.7%) | — | — | — |
| Not applicable | 4 (4.3%) | 57 (3.9%) | — | — | — |
| Oppositional Defiant Disorder/Conduct Disorder - Sibling | | | | | |
| Yes | 22 (23.9%) | 167 (11.5%) | 0.0014 | 2.43 | (1.39, 4.12) |
| No | 64 (69.6%) | 1181 (81.1%) | — | — | — |
| Not applicable | 6 (6.5%) | 108 (7.4%) | — | — | — |

CI = confidence interval; OR = odds ratio.
Note:
Percentages are 100*n/N.
[a]p-values derived from Fisher's Exact Test.
[b]OR and 95% CI derived from SAS Proc FREQ.

TABLE 9

Selected Psychiatric Family History (Either Parent) for the Subset of Subjects who were CNTN4-positive or mGluR-negative

| Parameter Category | CNTN4-positive ADHD Subjects (N = 92) | ADHD Subjects without mGluR Mutation (N = 1456) | P-value[a] | OR[b] | 95% CI[b] |
|---|---|---|---|---|---|
| Developmental Disability/Delay | | | | | |
| Yes | 11 (12.0%) | 58 (4.0%) | 0.0017 | 3.32 | (1.51, 6.71) |
| No | 78 (84.8%) | 1365 (93.8%) | — | — | — |
| Not applicable | 3 (3.3%) | 33 (2.3%) | — | — | — |
| Drug/Substance Abuse | | | | | |
| Yes | 33 (35.9%) | 272 (18.7%) | 0.0002 | 2.46 | (1.52, 3.93) |
| No | 57 (62.0%) | 1157 (79.5%) | — | — | — |
| Not applicable | 2 (2.2%) | 27 (1.9%) | — | — | — |
| Oppositional Defiant Disorder/Conduct Disorder | | | | | |
| Yes | 16 (17.4%) | 109 (7.5%) | 0.0021 | 2.64 | (1.38, 4.77) |
| No | 73 (79.3%) | 1313 (90.2%) | — | — | — |
| Not applicable | 3 (3.3%) | 34 (2.3%) | — | — | — |

Note:
Percentages are 100*n/N.
[a]p-values derived from Fisher's Exact Test.
[b]OR and 95% CI derived from SAS Proc FREQ.

Specific areas of concern evaluated (i.e., noted as present or absent) were also assessed regarding health problems/poor health, absenteeism, motivation, disobedience, inappropriate sounds, inappropriate movements, risk taking, peer relationships, immaturity, self-esteem, anger control, hyperactivity, unhappy at school, motor skills, attention, distractibility, inconsistent performance, disruptive behavior, test taking, homework, completing work, copying from board, retaining information, speech, reading, writing, spelling, and math.

Figure 3:
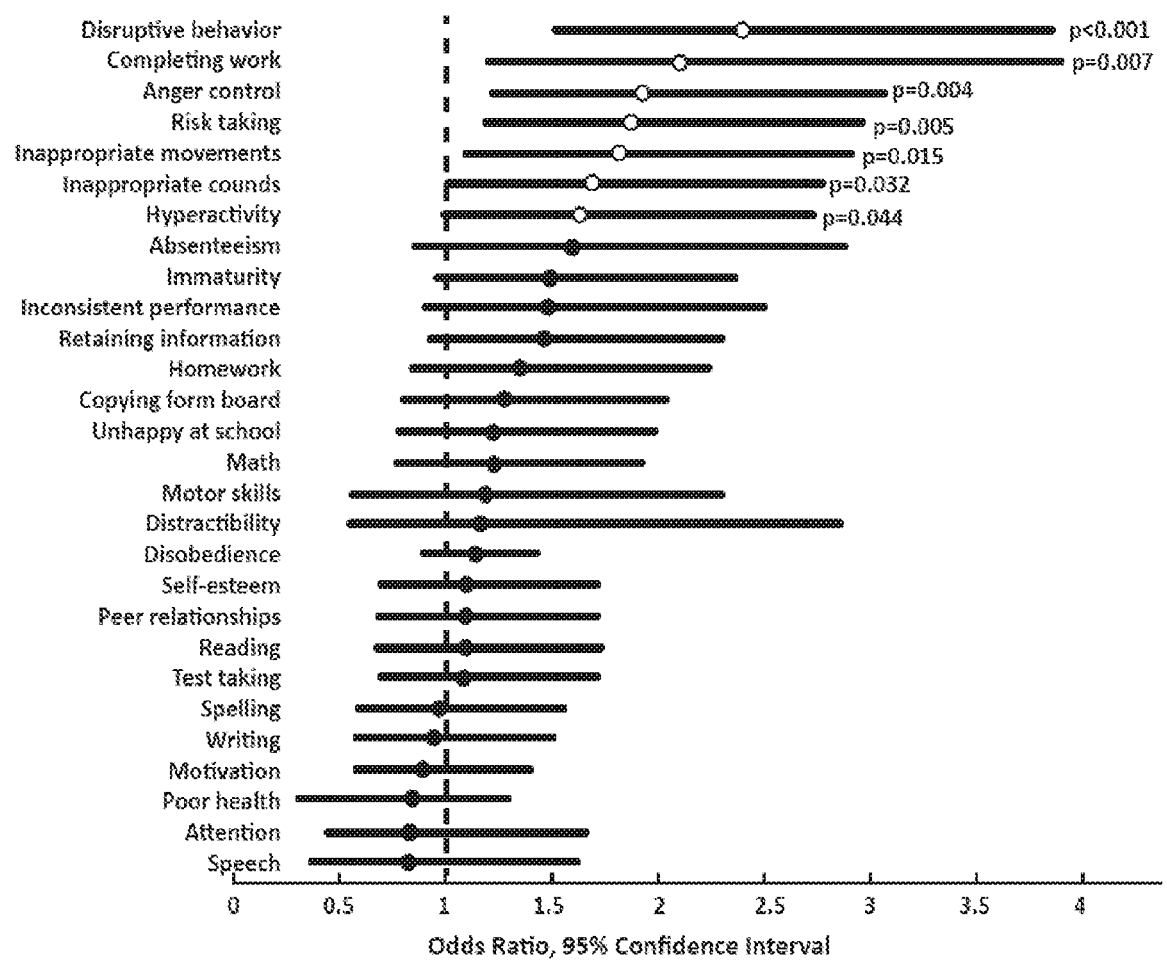
FIG. 3 shows the odds ratio (OR) of current behavioral concerns listed by parents of subjects in the CNTN4 CNV-positive cohort compared to the CNV-negative cohort. An OR greater than 1 indicates that a behavioral concern was more frequent in the subjects positive for a CNV in CNTN4.

Notable differences in current areas of parental concern for CNTN4-positive and mGluR-negative subjects are summarized in Table 10 and FIG. 3. A higher odds ratio (OR) in Table 10 or FIG. 3 indicates a higher frequency of the behavior in CNTN4-positive subjects compared with mGluR-negative subjects. Note that ORs were rounded to 3 significant digits in FIG. 3.

A higher rate of parental concern over inappropriate sounds was seen in CNTN4-positive subjects (29.3%) than in mGluR-negative subjects (19.6%: p=0.0315). A higher rate of parental concern over inappropriate movements was seen in CNTN4-positive subjects (30.4%) than in mGluR-negative subjects (19.4%; p=0.0151). A higher rate of parental concern over risk-taking was seen in CNTN4-positive subjects (40.2%) than in mGluR-negative subjects (26.2%:

p=0.0051). A higher rate of parental concern over anger control was seen in CNTN4-positive subjects (64.1%) than in mGluR-negative subjects (48.1%; p=0.0035). A higher rate of parental concern over hyperactivity was seen in CNTN4-positive subjects (73.9%) than in mGluR-negative subjects (63.5%: p=0.0442). A higher rate of parental concern over disruptive behavior was seen in CNTN4-positive subjects (65.2%) than in mGluR-negative subjects (43.8%; p=0.0001). A higher rate of parental concern over completing work was seen in CNTN4-positive subjects (82.6%) than in mGluR-negative subjects (69.2%; p=0.0066).

TABLE 10

Selected Current Areas of Parental Concern for the Subset of Subjects who were CNTN4-positive or mGluR-negative

| Parameter Category | CNTN4-positive ADHD Subjects (N = 92) | ADHD Subjects without mGluR Mutation (N = 1456) | P-value[a] | OR[b] | 95% CI[b] |
|---|---|---|---|---|---|
| Inappropriate Sounds | | | | | |
| Yes | 27 (29.3%) | 286 (19.6%) | 0.0315 | 1.70 | (1.02, 2.76) |
| No | 65 (70.7%) | 1170 (80.4%) | — | — | — |
| Inappropriate Movements | | | | | |
| Yes | 28 (30.4%) | 283 (19.4%) | 0.0151 | 1.81 | (1.10, 2.93) |
| No | 64 (69.6%) | 1173 (80.6%) | — | — | — |
| Risk Taking | | | | | |
| Yes | 37 (40.2%) | 382 (26.2%) | 0.0051 | 1.89 | (1.19, 2.97) |
| No | 55 (59.8%) | 1074 (73.8%) | — | — | — |
| Anger Control | | | | | |
| Yes | 59 (64.1%) | 701 (48.1%) | 0.0035 | 1.93 | (1.22, 3.08) |
| No | 33 (35.9%) | 755 (51.9%) | — | — | — |
| Hyperactivity | | | | | |
| Yes | 68 (73.9%) | 925 (63.5%) | 0.0442 | 1.63 | (0.99, 2.74) |
| No | 24 (26.1%) | 531 (36.5%) | — | — | — |
| Disruptive Behavior | | | | | |
| Yes | 60 (65.2%) | 637 (43.8%) | 0.0001 | 2.41 | (1.52, 3.87) |
| No | 32 (34.8%) | 819 (56.3%) | — | — | — |
| Completing Work | | | | | |
| Yes | 76 (82.6%) | 1008 (69.2%) | 0.0066 | 2.11 | (1.20, 3.92) |
| No | 16 (17.4%) | 448 (30.8%) | — | — | — |

Note:
Percentages are 100*n/N.
[a] p-values derived from Fisher's Exact Test.
[b] OR and 95% CI derived from SAS Proc FREQ.

Notable differences (i.e., differences >5.0%) in parent-reported positive developmental histories for CNTN4-positive and mGluR-negative subjects are presented in Table 11. Specific developmental histories evaluated (i.e., noted as present or absent) included vision problems, hearing problems, speech problems, delayed gross motor skills, delayed fine motor skills, delayed social skills, repeating a grade, need for an IEP/540 evaluation, placement in a special education class, previous need for tutoring, currently receiving tutoring, and number of times a grade was repeated. A frequency distribution of the current grade was also determined for CNTN4-positive and mGluR-negative subjects.

A lower rate of reported speech problems was seen in CNTN4-positive subjects (16.3%) than in mGluR-negative subjects (21.8%). A lower rate of reported delayed fine motor skills was seen in CNTN4-positive subjects (9.8%) than in mGluR-negative subjects (20.0%). A lower rate of reported delayed social skills was seen in CNTN4-positive subjects (15.2%) than in mGluR-negative subjects (24.5%). A higher rate of reports of having to repeat a grade was seen in CNTN4-positive subjects (22.8%) than in mGluR-negative subjects (17.1%). A higher rate of reports of ever receiving tutoring was seen in CNTN4-positive subjects (55.4%) than in mGluR-negative subjects (49.9%). A higher rate of reports of currently receiving tutoring was seen in CNTN4-positive subjects (28.3%) than in mGluR-negative subjects (20.5%).

TABLE 11

Selected Developmental Histories for the Subset of Subjects who were CNTN4- positive or mGluR-negative

| Parameter Category | CNTN4-positive ADHD Subjects (N = 92) | ADHD Subjects without mGluR Mutation (N = 1456) | Overall |
|---|---|---|---|
| Speech Problems | | | |
| Yes | 15 (16.3%) | 318 (21.8%) | 333 (21.5%) |
| No | 77 (83.7%) | 1138 (78.2%) | 1215 (78.5%) |
| Delayed Fine Motor Skills | | | |
| Yes | 9 (9.8%) | 291 (20.0%) | 300 (19.4%) |
| No | 83 (90.2%) | 1165 (80.0%) | 1248 (80.6%) |
| Delayed Social Skills | | | |
| Yes | 14 (15.2%) | 357 (24.5%) | 371 (24.0%) |
| No | 78 (84.8%) | 1099 (75.5%) | 1177 (76.0%) |
| Repeated a Grade | | | |
| Yes | 21 (22.8%) | 249 (17.1%) | 270 (17.4%) |
| No | 71 (77.2%) | 1207 (82.9%) | 1278 (82.6%) |
| Ever Received Tutoring | | | |
| Yes | 51 (55.4%) | 726 (49.9%) | 777 (50.2%) |
| No | 41 (44.6%) | 730 (50.1%) | 771 (49.8%) |
| Currently Receiving Tutoring | | | |
| Yes | 26 (28.3%) | 299 (20.5%) | 325 (21.0%) |
| No | 66 (71.7%) | 1157 (79.5%) | 1223 (79.0%) |

Note:
Percentages are 100*n/N
Thus, posthoc analyses on subjects with CNTN4 CNVs suggest that they are a vulnerable population of ADHD subjects at higher risk for poor outcomes.

Thus, posthoc analyses on subjects with CNTN4 CNVs suggest that they are a vulnerable population of ADHD subjects at higher risk for poor outcomes.

Example 3—Interventional Study of NFC-1 (Fasoracetam Monohydrate) in Children and Adolescents with ADIHD and Glutamatergic Network Gene CNVs To assess the efficacy and tolerability/safety of NFC-1 (also known as fasoracetam monohydrate) in CNV-positive adolescents with moderately severe ADHD, a randomized, double-blind, placebo-controlled, parallel-group phase 2 study of ADHD subjects 12-17 years old was conducted. This study, termed SAGA (SAGA (Study of Adolescent Glutamate Receptor Network Copy Number Variant ADHD), evaluated the efficacy and tolerability/safety of NFC-1 in CNV-positive adolescents with moderately severe ADHD (NCT03006367).

Positive effects of NFC-1 on learning and memory in animal models have been attributed to modulation of adenylyl cyclase activity and glutamate signaling mediated by metabotropic glutamate receptors (GRMs). Other reported actions have included facilitation of central cholinergic activity and upregulation of GABAB receptors.

Subjects received randomized treatment with either NFC-1 or placebo. Subjects had ADHD as defined by the Diagnostic and Statistical Manual of Mental Disorders, 5th edition (DSM-5) and Version 5 of the Attention Deficit Hyperactivity Disorder Rating Scale (ADHD RS-5) >28 at Baseline with or without conventional ADHD therapy.

The study was a multicenter, Phase 2, double-blind, randomized, placebo-controlled, parallel-group, dose-optimization study. The study enrolled adolescents 12-17 yrs (inclusive) with ADHD defined by DSM-5 criteria.

Subjects were CNV positive for a CNVs in at least one of the 273 Tier 1 or Tier 2 glutamatergic network genes of interest as listed in Table 1 or 2. These subjects positive for a CNV may also be termed "biomarker positive."

All subjects had a ADHD-RS-5 Total score ?28 at Baseline after ADHD medication washout.

Subjects who enrolled and completed the washout were randomly assigned to receive either NFC-1 or placebo on Day −1 and started taking NFC-1 at a dose of 10 mg twice daily on Day 1. Dosing was optimized to 100 mg, 200 mg, or 400 mg twice daily (BID), as appropriate, over the 4 weeks of treatment (dose optimization phase), based on clinical response and tolerability. The maximum dose was 400 mg BID or placebo. If the subject tolerated a dose well, the dose was maintained for an additional 2 weeks (dose maintenance phase) when the primary assessments of efficacy and tolerability were performed. Thus, optimized doses of NFC-1 were 100 mg, 200 mg, or 400 mg BID, and these doses were compared to placebo.

Efficacy was assessed by the ADHD RS-5, CGI-I, CGI-S, the Adolescent Sleep Hygiene Scale (ASHS), and the Screen for Childhood Anxiety-related Emotional Disorders (SCARED).

The ASHS is a self-report questionnaire assessing sleep practices theoretically important for optimal sleep in adolescents aged ≥12 years of age. It assesses physiological (e.g., evening caffeine consumption), cognitive (e.g., thinking about things that need to be done at bedtime), emotional (e.g., going to bed feeling upset), sleep environment (e.g., falling asleep with the lights on), sleep stability (e.g., different bedtime/wake time pattern on weekdays and at weekends), substance use (e.g., evening alcohol use), daytime sleep (e.g., napping), and having a bedtime routine.

The SCARED is a self-report instrument for children ages 8-18 years used to screen for childhood anxiety disorders including general anxiety disorder, separation anxiety disorder, panic disorder, and social phobia. In addition, it assesses symptoms related to school phobias. The SCARED consists of 41 items and 5 factors that parallel the DSM-IV classification of anxiety disorders. The scale has good internal consistency, test-retest reliability, and discriminant validity, and it is sensitive to treatment response.

The primary efficacy endpoint was the change from baseline in ADHD-RS-5 total score to end of study (last observation carried forward, LOCF) in Intent-to-Treat (ITT) population. The ITT population consisted of 101 patients randomized to NFC-1 or placebo.

Treatment response was evaluated by measurement of responders and remission. The definition of a "responder" in this study was a response at endpoint of:

A) ≥30% reduction from Baseline in ADHD-RS-5 Total score;
B) CGI-I score of 1 (very much improved) or 2 (much improved); OR
C) Composite (both A and B)

The definition of a "remission" in this study was a response at endpoint of:

A) ADHD-RS-5 Total score ≤18;
B) CGI-I score of 1. OR
C) Composite (both A and B)

In addition, post-hoc analysis evaluated predictors of treatment response.

Table 12 presents data on the subject characteristics of the safety population. A total of 101 patients were randomized to NFC-1 (N=49) or placebo (N=52), which constituted the ITTT population The number of subjects in the ITT population with post-Baseline efficacy data was NFC-1, n=46 (94%) and placebo, n=50 (96%). The safety population (randomized subjects receiving?1 dose of study drug) was NFC-1, n=47 (96%) and placebo, n=50 (96%).

TABLE 12

Subject Characteristics (Safety Population)

|  | NFC-1 BID (n = 47) | Placebo BID (n = 50) |
|---|---|---|
| Age, yrs, mean (SD) | 13.8 (1.40) | 14.4 (1.68) |
| Male, % (n) | 55% (26) | 70% (35) |
| ADHD Presentation, % (n) | | |
| Combined | 66% (31) | 74% (37) |
| Inattentive | 32% (15) | 24% (12) |
| Impulsive/Hyperactive | 2% (1) | 2% (1) |
| ADHD-RS-5 score at Baseline, mean (SD) | | |
| Total | 36.8 (6.88) | 38.6 (7.23) |
| Inattention | 21.8 (3.10) | 22.2 (3.01) |
| Hyperactivity-impulsivity | 15.0 (5.84) | 16.5 (6.12) |
| CGI-S score at Baseline | | |
| 4 - Moderately Ill, % (n) | 60% (28) | 62% (31) |
| 5 - Markedly Ill, % (n) | 38% (18) | 38% (19) |
| 6 - Severely Ill, % (n) | 2% (1) | 0 |

Figure 4:
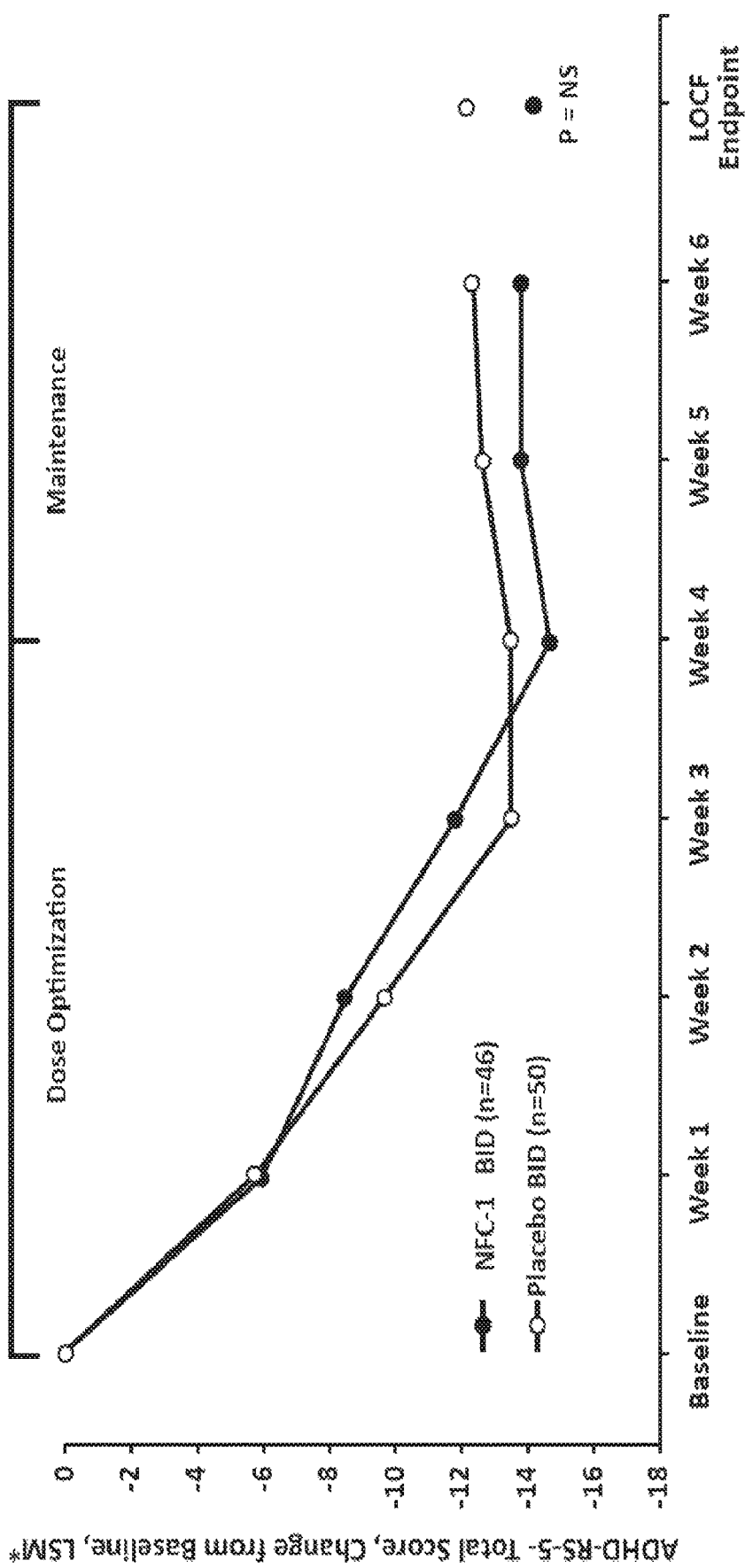
FIG. 4 shows ADHD-RS-5 total score change from baseline at endpoint (last observation carried forward, LOCF) and by visit for subjects having a CNV in a mGluR network gene and treated with NFC-1, fasoracetam) or placebo. At weeks 4-6, subjects were on their optimized dose of NFC-1 or placebo.

FIG. 4 shows primary efficacy endpoint data of ADHD-RS-5 total score change from Baseline to LOCF endpoint. FIG. 4 also presents ADHD-RS-5 total score measures at each visit (baseline and Weeks 1-Week 6). The difference between placebo and NFC-1 for the primary endpoint was not significant (NS).

A prespecified analysis of treatment response at endpoint was also performed, as shown in Table 13.

TABLE 13

Treatment response at endpoint (ITT, LOCF)

| Response Parameter | NFC-1 BID (n = 46) % (n) | Placebo BID (n = 50) % (n) | p value |
|---|---|---|---|
| ADHD RS-5 Total Score: ≥30% Reduction from Baseline | 70% (32) | 42% (21) | <0.01 |
| CGI-I Score 1 or 2 | 57% (26) | 32% (16) | <0.05 |
| Composite | 57% (26) | 32% (16) | <0.05 |

Compared to subjects treated with placebo, significantly more subjects treated with NFC-1 had a 30% or greater reduction from baseline in ADHD RS-5 total score (p<0.01), a CGI-I score of 1 or 2 at endpoint (p<:0.05), or a composite response (p<0.05). There was no significant difference between treatment groups in remission (data not shown).

Post-hoc analyses were performed to investigate predictors of treatment response. These predictors included specific gene CNVs.

Post-hoc inspection revealed that 8 genes were associated with robust treatment response in multiple subjects, CNTV4, GRM5, GRM8, MC4R, CTNNA2, SNCA. ADRA2A, and CA8. These 8 genes of interest were identified in 39 subjects (NFC-1, n=17; Placebo, n=22) included certain GRM genes and other CNS/neurodevelopmental genes. CNTN4 was the most frequent gene CNV in study population (n=19, 19% of randomized sample).

Table 14 presents data on subjects in the study with CNVs in one or more of the 8 genes of interest. "Response" represents change from baseline in ADHD RS-5 total score. Some subjects had more CNV(s) that affected more than 1 gene of interest edly Ill. 56%; Severely Ill, 6%), as compared to the CGI-Severity scores for the whole safety population as presented in Table 12.

A total of 18 subjects with a CNV in CNTN4 who were treated with either NFC-1 or placebo. Table 15 lists the responses of 12 subjects with a CNV in CNTN4 who were assigned to the placebo group, along with information on the CNV that was present in the subject. Table 15 includes data on the type (duplication or deletion), region (based on hg19), and size in nucleotides of the CNV present in CNTN4. The size of CNVs ranged frmn 1713-149014 nucleotides. As shown in Table 15, only 3/12 subjects with a CNTN4 CNV treated with placebo had a 30% or greater reduction from baseline in ADHD RS-5 total score labeled "Response").

TABLE 14

Data on subjects with CNVs in one or more gene of interest

| Age | Sex | Treatment Group | Gene | Response | Chr: start-stop(hg19) | Type |
|---|---|---|---|---|---|---|
| 13 | M | Placebo | ADRA2A | -30.76923077 | chr10: 113003211-113007752 | Deletion |
| 13 | F | Active | ADRA2A | -65 | chr10: 113000166-113011038 | Deletion |
| 14 | M | Active | CA8 | -33.33333333 | chr8: 60996982-61006187 | Deletion |
| 17 | M | Placebo | CA8 | -3.448275862 | chr8: 60997355-61006187 | Deletion |
| 15 | M | Placebo | CNTN4 | -5.405405405 | chr3: 2381839-2476577 | Deletion |
| 12 | F | Placebo | CNTN4 | -100 | chr3: 2023020-2028135 | Deletion |
| 14 | M | Placebo | CNTN4 | -7.142857143 | chr3: 1917909-1922565 | Deletion |
| 14 | M | Active | CNTN4 | -70 | chr3: 1918149-1922565 | Deletion |
| 13 | F | Active | CNTN4 | -45.71428571 | chr3: 1917909-1922565 | Deletion |
| 16 | M | Placebo | CNTN4 | -82.35294118 | chr3: 1917909-1922565 | Deletion |
| 13 | F | Active | CNTN4 | -48.64864865 | chr3: 1917909-1922565 | Deletion |
| 13 | M | Placebo | CNTN4 | -33.33333333 | chr3: 2748076-2751249 | Deletion |
| 15 | F | Active | CNTN4 | -35.8974359 | chr3: 2748076-2751249 | Deletion |
| 16 | M | Active | CNTN4 | -62.5 | chr3: 1917909-1922565 | Deletion |
| 14 | M | Placebo | CNTN4 | -6.666666667 | chr3: 1917909-1922565 | Deletion |
| 12 | M | Placebo | CNTN4 | -12.24489796 | chr3: 1917909-1922565 | Deletion |
| 15 | M | Placebo | CNTN4 | 5.714285714 | chr3: 1917909-1922565 | Deletion |
| 12 | F | Active | CNTN4 | 0 | chr3: 1917909-1922565 | Deletion |
| 16 | F | Placebo | CNTN4 | -7.5 | chr3: 2595938-2744952 | Duplication |
| 15 | M | Placebo | CNTN4 | 0 | chr3: 1917909-1920416 | Deletion |
| 13 | M | Active | CNTN4 | 0 | chr3: 1917909-1922565 | Deletion |
| 15 | M | Placebo | CNTN4 | 10.20408163 | chr3: 2572993-2574706 | Duplication |
| 16 | M | Placebo | CNTN4 | -18.91891892 | chr3: 1917909-1922565 | Deletion |
| 17 | F | Placebo | CNTN4 | -14.28571429 | chr3: 1913371-1925401 | Deletion |
| 14 | F | Active | CNTN4 | -77.41935484 | chr3: 1145301-2937380 | Deletion |
| 14 | F | Active | CTNNA2 | 0 | chr2: 80663912-80669260 | Deletion |
| 14 | M | Placebo | CTNNA2 | 21.875 | chr2: 79752148-79761222 | Deletion |
| 13 | M | Active | CTNNA2 | -6.666666667 | chr2: 79752148-79761222 | Deletion |
| 15 | M | Placebo | GRM5 | 0 | chr11: 88557991-88565086 | Duplication |
| 12 | M | Active | GRM5 | -37.5 | chr11: 88372708-88380551 | Deletion |
| 13 | M | Active | GRM8 | -48.27586207 | chr7: 125566215-125569665 | Deletion |
| 14 | F | Active | GRM8 | -39.02439024 | chr7: 126802341-126806732 | Deletion |
| 13 | M | Placebo | GRM8 | -12 | chr7: 126801989-126811206 | Deletion |
| 12 | F | Placebo | GRM8 | 2.43902439 | chr7: 126801989-126806732 | Deletion |
| 13 | M | Active | MC4R | -48.27586207 | chr18: 58043113-58044824 | Deletion |
| 12 | M | Active | MC4R | -18.18181818 | chr18: 58117122-58121144 | Deletion |
| 13 | M | Active | MC4R | -50 | chr18: 58100665-58121144 | Deletion |
| 13 | M | Placebo | MC4R | -16.21621622 | chr18: 58100665-58121144 | Deletion |
| 16 | M | Placebo | MC4R | 0 | chr18: 58117122-58121144 | Deletion |
| 15 | F | Active | MC4R | -62.85714286 | chr18: 58498845-58512420 | Deletion |
| 17 | F | Placebo | SNCA | 17.07317073 | chr4: 90581986-90592311 | Deletion |
| 13 | M | Active | SNCA | -76.92307692 | chr4: 90581986-90592311 | Deletion |
| 14 | F | Placebo | SNCA | 0 | chr4: 90581986-90592311 | Deletion |

ADHD-RS-5 total score change from baseline at endpoint (LOCF) and by visit for those subjects having a CNV in one of the genes in the 8-gene network (n=39) are shown in FIG. 5. A significantly greater reduction in ADHD-RS-5 total score was seen in patients treated with NFC-1 compared to those treated with placebo (p<0.001).

CNTN4 (encoding contactin 4, a cell adhesion molecule) was the gene that most commonly had a CNV in the study population (n=19, 19% of randomized sample). Baseline CGI-Severity index scores were skewed to more severe disease in the CNTN4 subset (Moderately Ill, 39%; Mark-

TABLE 15

Data on response rate and type of CNV in individual subjects in the placebo-treated group

| Response | Gene | Type | Region | Size |
|---|---|---|---|---|
| -100 | CNTN4 | Deletion | chr3: 2023020-2028135 | -5115 |
| -82.37 | CNTN4 | Deletion | chr3: 1917909-1922565 | -4656 |

TABLE 15-continued

Data on response rate and type of CNV in individual subjects in the placebo-treated group

| Response | Gene | Type | Region | Size |
|---|---|---|---|---|
| −33.33 | CNTN4 | Deletion | chr3: 2748076-2751249 | −3173 |
| −18.92 | CNTN4 | Deletion | chr3: 1917909-1922565 | −4656 |
| −14.29 | CNTN4 | Deletion | chr3: 1913371-1925401 | −12030 |
| 12.24 | CNTN4 | Deletion | chr3: 1917909-1922565 | −4656 |
| −7.5 | CNTN4 | Duplication | chr3: 2595938-2744952 | +149014 |
| −7.14 | CNTN4 | Deletion | chr3: 1917909-1922565 | −4656 |
| −6.67 | CNTN4 | Deletion | chr3: 1917909-1922565 | −4656 |
| −5.41 | CNTN4 | Deletion | chr3: 2381839-2476577 | −94738 |

RS-S Total Score by LSM (p=0.09); the between-group difference was significant (p=:0.03) with uncorrected Wilcoxon rank-sum test.

Table 17 presents data on the treatment response at study end for subjects with a CNV in the 8-gene subset (that included CNTN4) and for subjects with a CNV specifically in CTNT4. All CNTN4 CNV-positive patients are included in the 8-gene subset. As shown in Table 17, the presence of a CNV in the 8-gene network or specifically in CNTN4 were predictive of a clinically meaningful response to NFC-1 treatment.

TABLE 17

Treatment response at study end (LOCF) for 8-gene subset and CNTN4 subset

| | 8-Gene Subset including CNTN4 | | | CNTN4 Subset | | |
|---|---|---|---|---|---|---|
| Response Parameter | NFC-1 BID (n = 17) % (n) | Placebo BID (n = 22) % (n) | p value$^a$ | NFC-1 BID (n = 6) % (n) | Placebo BID (n = 12) % (n) | p value$^a$ |
| ADHD-RS-5 Total Score: ≥30% Reduction from Baseline | 88% (15) | 18% (4) | <0.0001 | 100% (6) | 25% (3) | <0.005 |
| CGI-I Score 1 or 2 | 76% (13) | 9% (2) | <0.0001 | 83% (5) | 17% (2) | <0.01 |
| Composite | 76% (13) | 9% (2) | <0.0001 | 83% (5) | 17% (2) | <0.01 |

$^a$p-value from Chi-square test of association.

TABLE 15-continued

Data on response rate and type of CNV in individual subjects in the placebo-treated group

| Response | Gene | Type | Region | Size |
|---|---|---|---|---|
| 5.71 | CNTN4 | Deletion | chr3: 1917909-1922565 | −4656 |
| 10.2 | CNTN4 | Duplication | chr3: 2572993-2574706 | +1713 |

Throughout, the "Response" columns represent the % reduction in ADHD-RS score at endpoint from baseline.

Table 16 lists the responses of the 6 subject with a CNV in CNTN4 who were assigned to the NFC-1 group, along with information on the CNV that was present in the subject. Table 16 includes data on the type (duplication or deletion), region (based on hg19), and size in nucleotides of the CNV present in CNTN4. The size of CNVs ranged from 3173-1792079 nucleotides. As shown in Table 16, all 6/6 patients treated with NFC-1 had a 30% or greater reduction from baseline in ADHD RS-5 total score (labeled "Response").

TABLE 16

Data on response rate and type of CNV in individual subjects in the NFC-1-treated group

| Response | Gene | Type | Region | Size |
|---|---|---|---|---|
| −77.42 | CNTN4 | Deletion | chr3: 1145301-2937380 | −1792079 |
| −70 | CNTN4 | Deletion | chr3: 1918149-1922565 | −4416 |
| −62.5 | CNTN4 | Deletion | chr3: 1917909-1922565 | −4656 |
| −48.65 | CNTN4 | Deletion | chr3: 1917909-1922565 | −4656 |
| −41.46 | CNTN4 | Deletion | chr3: 1917909-1922565 | −4656 |
| −35.9 | CNTN4 | Deletion | chr3: 2748076-2751249 | −3173 |

FIG. 6 presents data on the 18 subjects who were positive for a CNV in CNTN4. There was a trend in favor of NFC-1 compared with placebo in change from Baseline ADHD- Table 18 presents a summary of responses for each placebo-treated subject with a CNV in one of the 8 genes of interest. "Response" represents change from baseline in ADHD RS-5 total score. "Responder" indicates a 30% or greater reduction from baseline in ADHD RS-5 total score.

TABLE 18

Responses of placebo-treated patients with CNV in gene of interest

| Gene | Response | Responder? (Y/N) |
|---|---|---|
| ADRA2A | −30.7692 | Y |
| CA8 | −3.44828 | N |
| CNTN4 | −100 | Y |
| CNTN4 | −12.2449 | N |
| CNTN4 | −33.3333 | Y |
| CNTN4 | −7.14286 | N |
| CNTN4 | −6.66667 | N |
| CNTN4 | −5.40541 | N |
| CNTN4 | 5.714286 | N |
| CNTN4 | 10.20408 | N |
| CNTN4 | −82.3529 | Y |
| CNTN4 | −18.9189 | N |
| CNTN4 | −7.5 | N |
| CNTN4 | −14.2857 | N |
| CTNNA2 | 21.875 | N |
| GRM5 | 0 | N |
| GRM8 | 2.439024 | N |
| GRM8 | −12 | N |
| MC4R | −16.2162 | N |
| MC4R | 0 | N |
| SNCA | 0 | N |
| SNCA | 17.07317 | N |

Table 19 presents a summary of responses for each NFC-1-treated subject with a CNV in one of the 8 genes of interest.

TABLE 19

Responses of NFC-1-treated patients with CNV in gene of interest

| Gene | Response | Responder? (Y/N) |
|---|---|---|
| ADRA2A | −65 | Y |
| CA8 | −33.3333 | Y |
| CNTN4 | N/A | N/A |
| CNTN4 | −48.6486 | Y |
| CNTN4 | −41.4634 | Y |
| CNTN4 | −77.4194 | Y |
| CNTN4 | −70 | Y |
| CNTN4 | −35.8974 | Y |
| CNTN4 | −62.5 | Y |
| CTNNA2 | −6.66667 | N |
| CTNNA2 | −63.4146 | Y |
| GRM5 | −37.5 | Y |
| GRM8 | −48.2759 | Y |
| GRM8 | −39.0244 | Y |
| MC4R | −18.1818 | N |
| MC4R | −50 | Y |
| MC4R | −62.8571 | Y |
| SNCA | −76.9231 | Y |

Table 20 presents data on the tolerability and safety of NFC-1 treatment in the safety population (N=97).

TABLE 20

Most frequent (≥5% Occurrence) treatment-emergent adverse events (TEAEs)

| | NFC-1 (n = 47) % (n) | Placebo (n = 50) % (n) |
|---|---|---|
| Any TEAE | 70% (33) | 56% (28) |
| Discontinuations due to TEAEs | 6% (3) | 6% (3) |
| Fatigue | 15% (7) | 6% (3) |
| Weight increased | 15% (7) | 4% (2) |
| Accidental overdose | 11% (5) | 6% (3) |
| Headache | 9% (4) | 10% (5) |
| Appetite increased | 6% (3) | 4% (2) |
| Nausea | 6% (3) | 8% (4) |
| Upper respiratory tract infection | 4% (2) | 10% (5) |
| Nasopharyngitis | 2% (1) | 8% (4) |
| Irritability | 2% (1) | 6% (3) |

Dosing with the highest dose of NFC-1 (400 mg BID) was achieved in 91% of subjects in the safety population who were randomized to NFC-1. TEAE occurrence increased with optimized dose (100 mg BID, 30%; 200 mg BID, 32%; 400 mg BID, 54%). No serious TEAEs were reported, and the majority of TEAEs were mild-to-moderate in severity. These data indicate that NFC-1 was generally well-tolerated.

In summary, the difference between NFC-1 and placebo in change from Baseline ADHD-RS-5 Total score was not significant in the overall population of this Phase 2 study in adolescents with ADHD and CNVs in glutamate signaling and connectivity genes of interest.

NFC-1 was associated with significantly greater proportion of subjects meeting pre-specified criteria indicating clinically meaningful response. Predictors of clinically meaningful response to NFC-1 were CNVs in a 8-gene subset that included certain GRMs and CNTN4.

CNVs in CNTN4 were the most prevalent in the overall population, accounting for 19% of randomized subjects, and were associated with a robust clinical response to NFC-1. The clinically meaningful response observed in the 8-gene subset appeared largely attributable to the CNTN4 subset.

Based on these data, alterations in CNTN4 are important biomarker for studying treatment responses to ADHD medications. Preliminary findings suggest that NFC-1 may be a treatment with greater efficacy in patients with a CNV in the CNTN4 gene compared to its effect across all patients with ADHD.

We claim:

1. A method of treating attention deficit hyperactivity disorder (ADHD) in a subject comprising administering fasoracetam to the subject who has at least one copy number variation (CNV) in a subset of mGluR network genes selected from CNTN4, GRM8, MC4R, CTNNA2, SNCA, ADRA2A, GRM5, and CA8, wherein the fasoracetam is administered at a dose of 50-400 mg and wherein the dose is administered once, twice, or three times daily.

2. The method of claim 1, wherein fasoracetam is administered to the subject in an amount effective to result in a clinical general impression improvement (CGI-I) score of 1 or 2 after at least four weeks of treatment and/or an improvement of at least 25% in an ADHD rating scale score after at least four weeks of treatment.

3. The method of claim 1, wherein the CNV is in CNTN4.

4. The method of claim 1, wherein the subject is a pediatric or adolescent subject.

5. The method of claim 1, wherein the subject is an adult.

6. The method of claim 1, wherein the fasoracetam is fasoracetam monohydrate.

7. The method of claim 1, wherein the fasoracetam is administered at a dose of 100 mg, 200 mg, 300 mg, or 400 mg twice daily.

8. The method of claim 1, wherein the fasoracetam is further administered in combination with at least one of the following:
   (i) a stimulant;
   (ii) a nonstimulant;
   (iii) an anxiolytic;
   (iv) an anti-psychotic; or
   (v) a beta blocker.

9. The method of claim 1, wherein the fasoracetam is further administered in combination with non-pharmaceutical therapy selected from vagus nerve stimulation, repetitive transcranial magnetic stimulation, magnetic seizure therapy, and deep brain stimulation.

10. The method of claim 1, wherein the fasoracetam is administered as a monotherapy.

11. The method of claim 10, wherein the fasoracetam is administered after washout of other ADHD medications.

12. The method of claim 1, wherein a decrease in the dosage of other ADHD medications is made after the fasoracetam is administered.

13. The method of claim 1, wherein at least one of the following applies:
   (i) the subject has symptoms of anger control issues wherein administration of fasoracetam increases anger control in the subject;
   (ii) the subject has disruptive behavior wherein administration of fasoracetam reduces disruptive behavior in the subject;
   (iii) the subject has risk taking behaviors wherein administration of fasoracetam
   (iv) the subject has difficulty completing work wherein administration of fasoracetam improves the ability of the subject to complete work; or
   (v) the subject has inappropriate movements or sounds/noise making wherein administration of fasoracetam reduces inappropriate movements or sounds/noise making in the subject.

14. The method of claim 1, wherein the CNV is detected by a genetic test comprising:
    analyzing a nucleic acid from a sample obtained from the subject for a genetic alteration in at least one mGluR network gene selected from CNTN4, GRM8, MC4R, CTNNA2, SNCA, ADRA2A, GRM5, and CA8, and
    wherein the method comprises obtaining results of the genetic test prior to initial administration of the fasoracetam.

15. The method of claim 1, wherein the CNV is a duplication.

16. The method of claim 1, wherein the CNV is a deletion.

17. The method of claim 2, wherein the fasoracetam is further administered in combination with at least one of the following:
    (i) stimulant;
    (ii) a nonstimulant;
    (iii) an anxiolytic;
    (iv) an anti-psychotic; or
    (v) a beta blocker.

18. The method of claim 2, wherein the fasoracetam is further administered in combination with a non-pharmaceutical therapy selected from the group consisting of vagus nerve stimulation, repetitive transcranial magnetic stimulation, magnetic seizure therapy, and deep brain stimulation.

19. The method of claim 14, wherein the nucleic acid is isolated from the sample.

20. The method of claim 14, wherein the nucleic acid is amplified by PCR.

21. The method of claim 14, wherein the nucleic acid is both isolated from the sample and amplified.

* * * * *